(12) United States Patent
Pilkington et al.

(10) Patent No.: US 7,619,068 B2
(45) Date of Patent: Nov. 17, 2009

(54) OVR110 ANTIBODY COMPOSITIONS AND METHODS OF USE

(75) Inventors: Glenn Pilkington, Rye (AU); Gilbert-Andre Keller, Belmont, CA (US); Wenlu Li, South San Francisco, CA (US); Laura Corral, Jamaica Plain, MA (US); Iris Simon, Amsterdam (NL); Jackie Papkoff, San Francisco, CA (US)

(73) Assignee: diaDexus, Inc., South San Francisco, CA (US)

( * ) Notice: Subject to any disclaimer, the term of this patent is extended or adjusted under 35 U.S.C. 154(b) by 0 days.

(21) Appl. No.: 10/557,331

(22) PCT Filed: May 10, 2004

(86) PCT No.: PCT/US2004/014490

§ 371 (c)(1),
(2), (4) Date: Nov. 29, 2006

(87) PCT Pub. No.: WO2004/101756

PCT Pub. Date: Nov. 25, 2004

(65) Prior Publication Data

US 2007/0178101 A1    Aug. 2, 2007

Related U.S. Application Data

(60) Provisional application No. 60/469,555, filed on May 9, 2003, provisional application No. 60/552,959, filed on Mar. 12, 2004, provisional application No. 60/556,464, filed on Mar. 25, 2004.

(51) Int. Cl.
| | |
|---|---|
| C07K 16/00 | (2006.01) |
| C12P 21/08 | (2006.01) |
| C07K 17/00 | (2006.01) |
| C07K 17/14 | (2006.01) |
| A61K 39/395 | (2006.01) |
| A61K 39/00 | (2006.01) |
| G01N 33/53 | (2006.01) |
| G01N 33/567 | (2006.01) |
| G01N 33/574 | (2006.01) |

(52) U.S. Cl. ............ 530/387.1; 530/388.1; 530/388.85; 530/391.1; 424/130.1; 424/138.1; 424/141.1; 424/155.1; 424/178.1; 435/7.1; 435/7.2; 435/7.23

(58) Field of Classification Search ........................ None
See application file for complete search history.

(56) References Cited

U.S. PATENT DOCUMENTS

| 2002/0004587 A1 | 1/2002 | Miller et al. ............. 530/388.8 |
| 2003/0087250 A1 * | 5/2003 | Monahan et al. ............... 435/6 |

FOREIGN PATENT DOCUMENTS

| WO | WO 99/63088 | | 12/1999 |
| WO | WO 00/12758 | | 3/2000 |
| WO | WO/00/12758 | * | 3/2000 |
| WO | WO 00/36107 | | 6/2000 |
| WO | WO 02/06317 A2 | | 1/2002 |

OTHER PUBLICATIONS

Yang, Green, Pinz-Sweeney, Briones, Burton, and Barbas. CDR walking mutagenesis for the affinity maturation of a potent human anti-HIV-1 antibody into the picomolar range. Journal of Molecular Biology, 1995. vol. 254, pp. 392-403.*

* cited by examiner

*Primary Examiner*—David J. Blanchard
*Assistant Examiner*—Anne M. Gussow
(74) *Attorney, Agent, or Firm*—Licata & Tyrrel P.C.; Keith R. McCollum

(57) ABSTRACT

The invention provides isolated anti-ovarian, pancreatic, lung or breast cancer antigen (Ovr110) antibodies that internalize upon binding to Ovr110 on a mammalian in vivo. The invention also encompasses compositions comprising an anti-Ovr110 antibody and a carrier. These compositions can be provided in an article of manufacture or a kit. Another aspect of the invention is an isolated nucleic acid encoding an anti-Ovr110 antibody, as well as an expression vector comprising the isolated nucleic acid. Also provided are cells that produce the anti-Ovr110 antibodies. The invention encompasses a method of producing the anti-Ovr110 antibodies. Other aspects of the invention are a method of killing an Ovr110-expressing cancer cell, comprising contacting the cancer cell with an anti-Ovr110 antibody and a method of alleviating or treating an Ovr110-expressing cancer in a mammal, comprising administering a therapeutically effective amount of the anti-Ovr110 antibody to the mammal.

148 Claims, 20 Drawing Sheets

FIGURE 1: Results of FACS Analysis of Ovr110 Transfected Mouse LMTK Cells
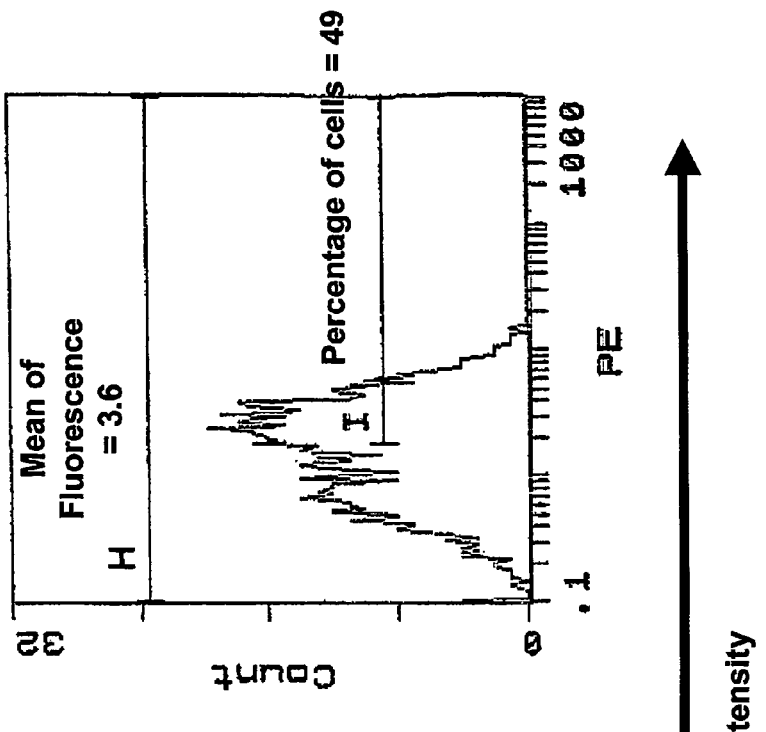
Fig 1B. MAb A7.1 & Donkey Anti-Mouse Ig-PE
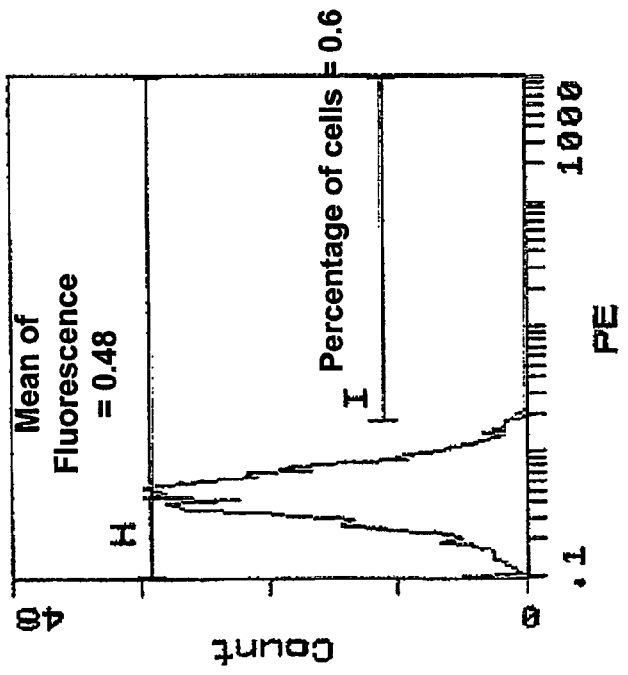
Fig 1A. Donkey Anti-Mouse Ig-PE Immunofluorescence with Ovr110-A57.1 in live ovarian and breast cancer cells Ovr110-A57.1 binding and internalization in live ovarian and breast cancer cells

FIGURE 4:
Immunohistochemistry with Ovr110-A57.1 in ovarian serous adenocarcinoma
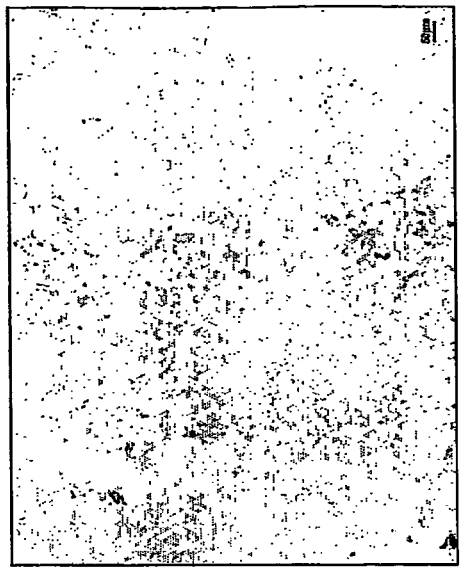
Fig 4C.
Fig 4B.
Fig 4A.

FIGURE 5:
Immunohistochemistry with Ovr110-A57.1 in breast infiltrating ductal adenocarcinoma
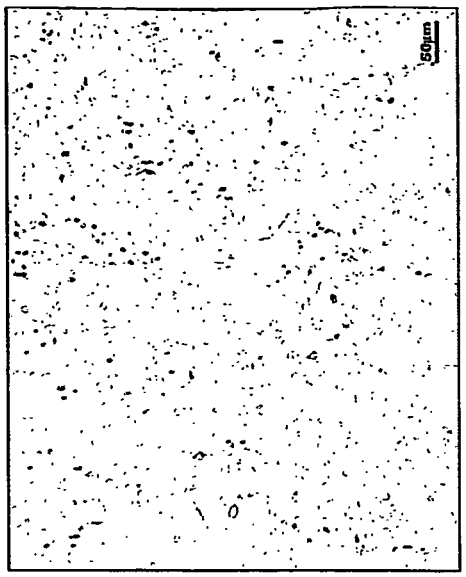
Fig 5C.
Fig 5B.
Fig 5A.

FIGURE 6:
Immunohistochemistry with Ovr110-A57.1 in pancreas adenocarcinoma
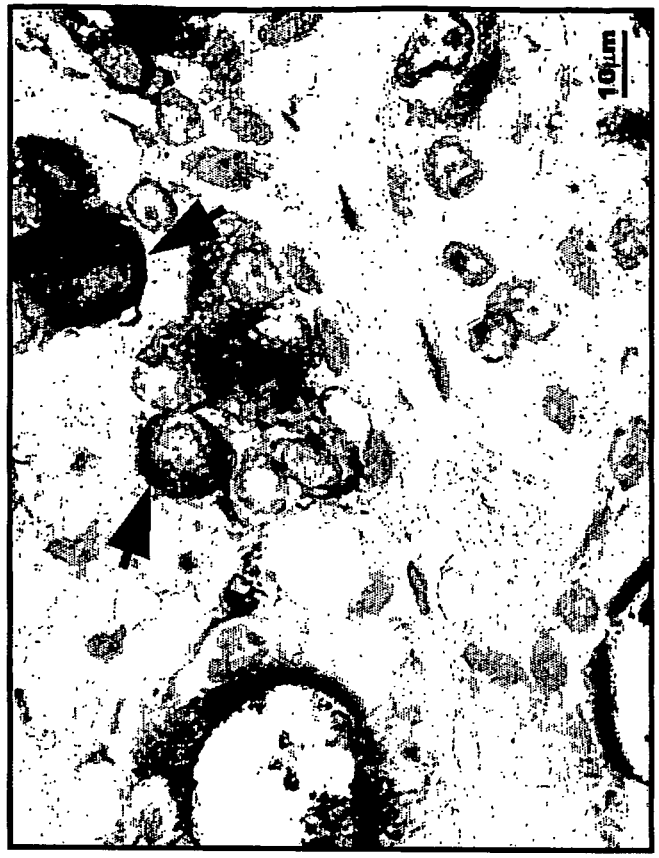
Fig 6B.
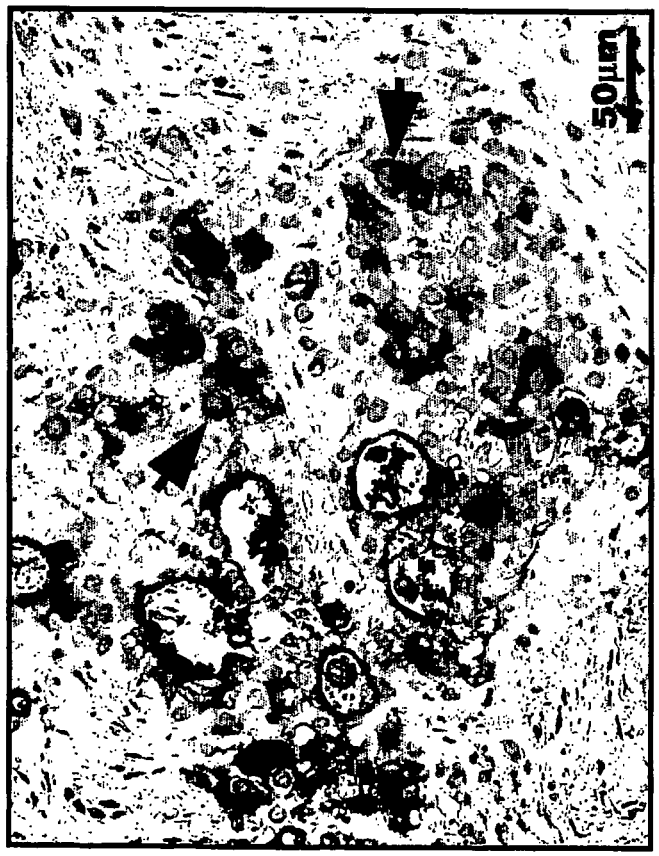
Fig 6A.

Figure 7A-7F: Expression of B7 Family Members on Day 3 PHA Stimulated T-CELLS CD3 FITC GATED

CD80 (B7.1)

CD86 (B7.2)

Ovr110 (A57.1)

CD71 (Transferrin)

CD25 (IL-2R)

2° Ab alone

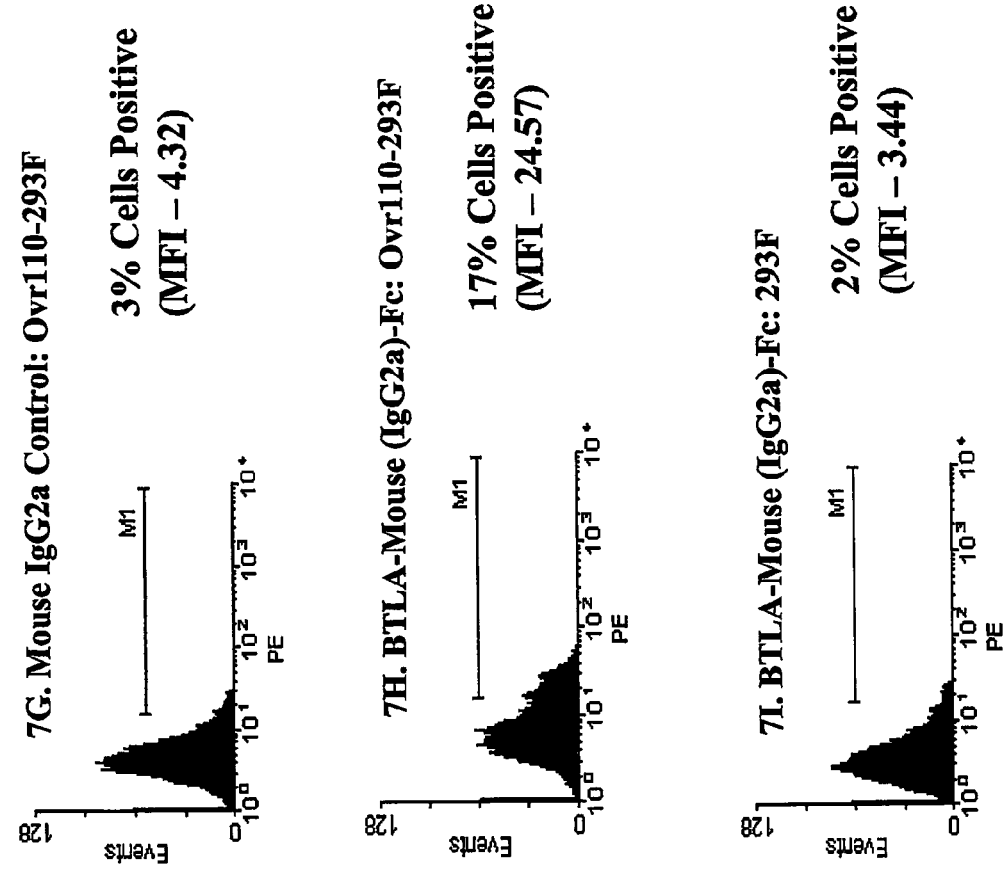
Figure 7G, 7H, 7I: Binding of BTLA-Fc Fusion Protein to Ovr110-293F Cells

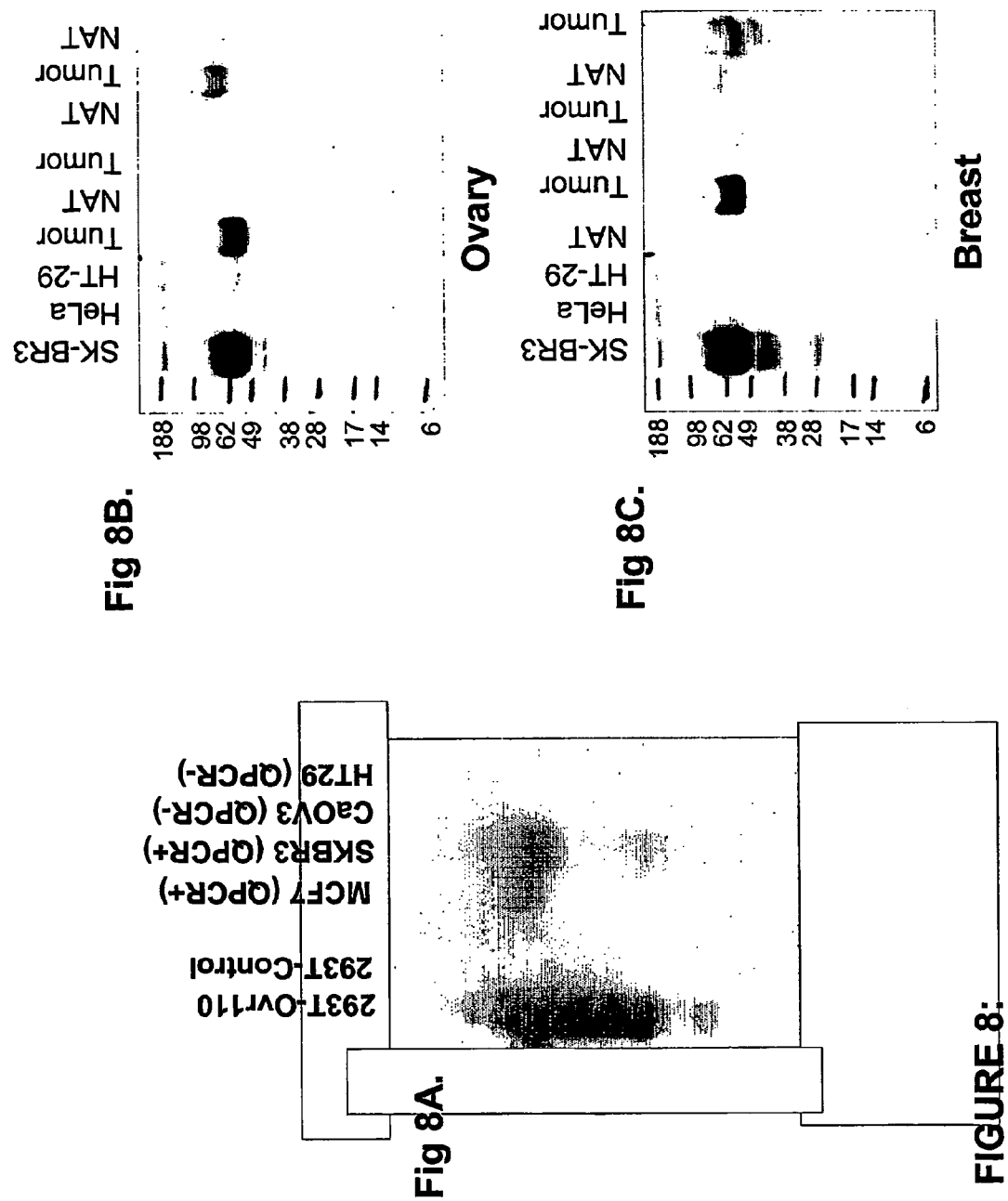
FIGURE 8: Western Blot Detection of Ovr110 Protein with mAb A57.1 in Cell Lines and Human Tumor Tissues Ovr110 Protein is not Detected in Extracts of Major Organs

FIGURE 10: Specific Knockdown of Ovr110 mRNA in SKBR3 Breast Cancer Cells

Ovr110 Q-PCR Primers
$\Delta CT = 1.5$
Ovr110 Knockdown 65%

GAPDH Q-PCR Primers
$\Delta CT = 0$
GAPDH Knockdown 0%

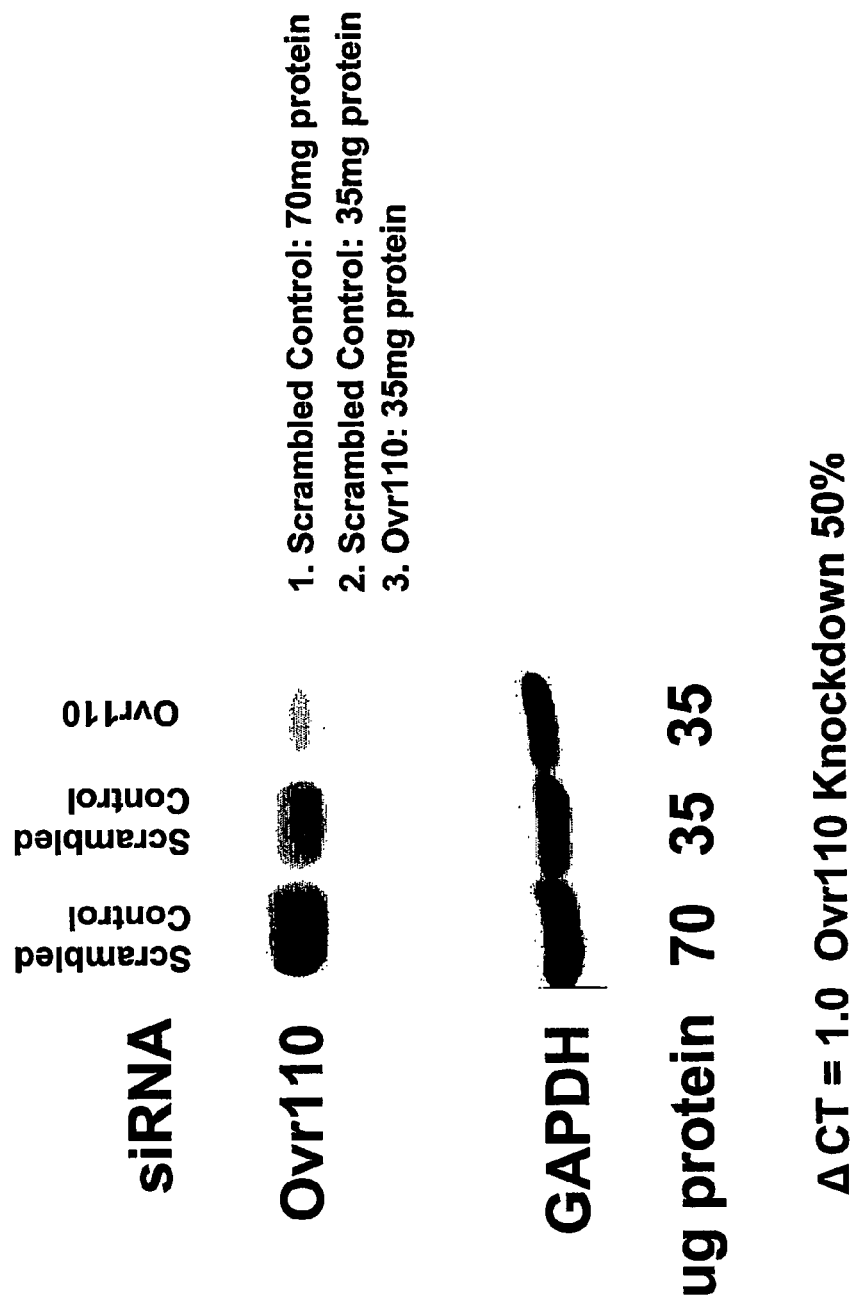
FIGURE 11: Down-Regulation of Ovr110 Protein by siRNA in SKBR3 Cells

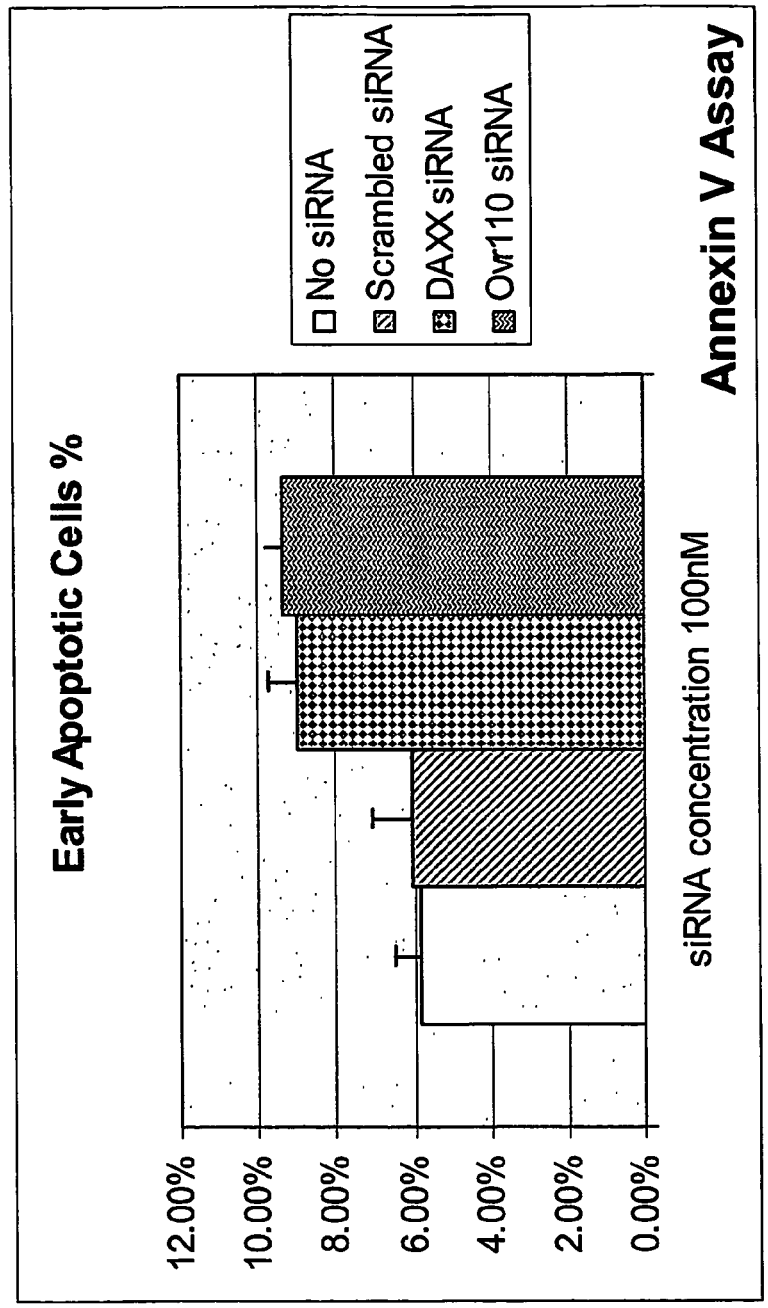
FIGURE 12: Knockdown of Ovr110 mRNA Induces Apoptosis in SKBR3 Cells

FIGURE 13: Knockdown of Ovr110 mRNA Induces Caspase Activity in SKBR3 Cells

ΔCT = 1.3 Ovr110 Knockdown 66%
ΔCT = 1.2 DAXX Knockdown 60%

DAXX: positive control
Scrambled: negative control

Overexpression of Ovr110 Enhances Tumor Xenograft Growth

FIGURE 15:
Overexpression of Ovr110 Protects from Apoptosis
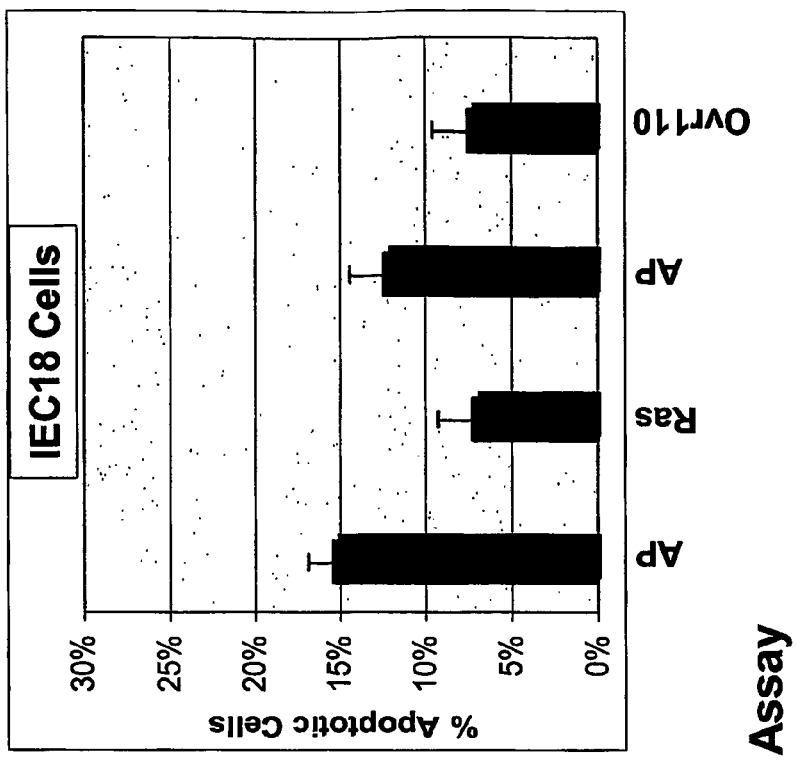
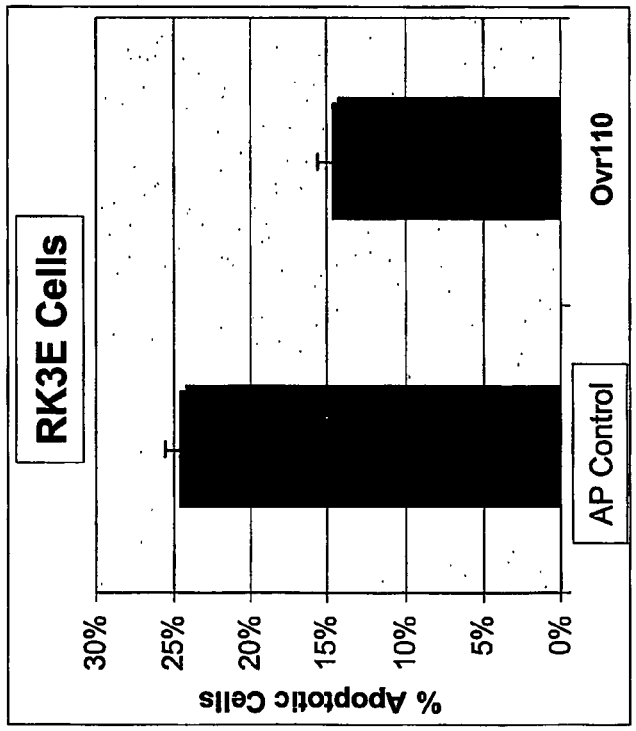
Anoikis Assay
(FBS-free Media)

FIGURE 16: Ovr110: Epitope-Map

Ovr110 detection in serum of healthy donors and cancer patients

FIGURE 19: Ovr110 ROC Curves in Ovarian Cancer

All Ovarian cancer
Area under the ROC curve = 0.78
Standard error = 0.020
95% Confidence interval = 0.745 to 0.811

Serous Ovarian Cancer
Area under the ROC curve = 0.8
Standard error = 0.023
95% Confidence interval = 0.770 to 0.838

SEQUENCE LISTING

```
<160> NUMBER OF SEQ ID NOS: 19

<210> SEQ ID NO 1
<211> LENGTH: 306
<212> TYPE: PRT
<213> ORGANISM: Artificial sequence
<220> FEATURE:
<223> OTHER INFORMATION: Synthetic

<400> SEQUENCE: 1

Met Leu Gln Asn Ser Ala Val Leu Leu Val Leu Val Ile Ser Ala Ser
1               5                   10                  15

Ala Thr Met Ala Ser Leu Gly Gln Ile Leu Phe Trp Ser Ile Ile Ser
            20                  25                  30

Ile Ile Ile Ile Leu Ala Gly Ala Ile Ala Leu Ile Ile Gly Phe Gly
        35                  40                  45

Ile Ser Gly Arg His Ser Ile Thr Val Thr Thr Val Ala Ser Ala Gly
    50                  55                  60

Asn Ile Gly Glu Asp Gly Ile Gln Ser Cys Thr Phe Glu Pro Asp Ile
65                  70                  75                  80

Lys Leu Ser Asp Ile Val Ile Gln Trp Leu Lys Glu Gly Val Leu Gly
                85                  90                  95

Leu Val His Glu Phe Lys Glu Gly Lys Asp Glu Leu Ser Glu Gln Asp
            100                 105                 110

Glu Met Phe Arg Gly Arg Thr Ala Val Phe Ala Asp Gln Val Ile Val
        115                 120                 125

Gly Asn Ala Ser Leu Arg Leu Lys Asn Val Gln Leu Thr Asp Ala Gly
    130                 135                 140

Thr Tyr Lys Cys Tyr Ile Ile Thr Ser Lys Gly Lys Gly Asn Ala Asn
145                 150                 155                 160

Leu Glu Tyr Lys Thr Gly Ala Phe Ser Met Pro Glu Val Asn Val Asp
                165                 170                 175

Tyr Asn Ala Ser Ser Glu Thr Leu Arg Cys Glu Ala Pro Arg Trp Phe
            180                 185                 190

Pro Gln Pro Thr Val Val Trp Ala Ser Gln Val Asp Gln Gly Ala Asn
        195                 200                 205

Phe Ser Glu Val Ser Asn Thr Ser Phe Glu Leu Asn Ser Glu Asn Val
```

```
            210                 215                 220
Thr Met Lys Val Val Ser Val Leu Tyr Asn Val Thr Ile Asn Asn Thr
225                 230                 235                 240

Tyr Ser Cys Met Ile Glu Asn Asp Ile Ala Lys Ala Thr Gly Asp Ile
                245                 250                 255

Lys Val Thr Glu Ser Glu Ile Lys Arg Arg Ser His Leu Gln Leu Leu
            260                 265                 270

Asn Ser Lys Ala Ser Leu Cys Val Ser Ser Phe Phe Ala Ile Ser Trp
        275                 280                 285

Ala Leu Leu Pro Leu Ser Pro Tyr Leu Met Leu Lys His His His His
290                 295                 300

His His
305

<210> SEQ ID NO 2
<211> LENGTH: 278
<212> TYPE: PRT
<213> ORGANISM: Artificial sequence
<220> FEATURE:
<223> OTHER INFORMATION: Synthetic

<400> SEQUENCE: 2

Met Leu Gln Asn Ser Ala Val Leu Leu Val Leu Val Ile Ser Ala Ser
1               5                   10                  15

Ala Thr Met Gly Ile Ser Gly Arg His Ser Ile Thr Val Thr Thr Val
            20                  25                  30

Ala Ser Ala Gly Asn Ile Gly Glu Asp Gly Ile Gln Ser Cys Thr Phe
        35                  40                  45

Glu Pro Asp Ile Lys Leu Ser Asp Ile Val Ile Gln Trp Leu Lys Glu
    50                  55                  60

Gly Val Leu Gly Leu Val His Glu Phe Lys Glu Gly Lys Asp Glu Leu
65                  70                  75                  80

Ser Glu Gln Asp Glu Met Phe Arg Gly Arg Thr Ala Val Phe Ala Asp
                85                  90                  95

Gln Val Ile Val Gly Asn Ala Ser Leu Arg Leu Lys Asn Val Gln Leu
            100                 105                 110

Thr Asp Ala Gly Thr Tyr Lys Cys Tyr Ile Ile Thr Ser Lys Gly Lys
        115                 120                 125

Gly Asn Ala Asn Leu Glu Tyr Lys Thr Gly Ala Phe Ser Met Pro Glu
    130                 135                 140

Val Asn Val Asp Tyr Asn Ala Ser Ser Glu Thr Leu Arg Cys Glu Ala
145                 150                 155                 160

Pro Arg Trp Phe Pro Gln Pro Thr Val Val Trp Ala Ser Gln Val Asp
                165                 170                 175

Gln Gly Ala Asn Phe Ser Glu Val Ser Asn Thr Ser Phe Glu Leu Asn
            180                 185                 190

Ser Glu Asn Val Thr Met Lys Val Ser Val Leu Tyr Asn Val Thr
        195                 200                 205

Ile Asn Asn Thr Tyr Ser Cys Met Ile Glu Asn Asp Ile Ala Lys Ala
    210                 215                 220

Thr Gly Asp Ile Lys Val Thr Glu Ser Glu Ile Lys Arg Arg Ser His
225                 230                 235                 240

Leu Gln Leu Leu Asn Ser Lys Ala Ser Leu Cys Val Ser Ser Phe Phe
                245                 250                 255

Ala Ile Ser Trp Ala Leu Leu Pro Leu Ser Pro Tyr Leu Met Leu Lys
```

His His His His His His
    275

<210> SEQ ID NO 3
<211> LENGTH: 30
<212> TYPE: DNA
<213> ORGANISM: Artificial sequence
<220> FEATURE:
<223> OTHER INFORMATION: Synthetic

<400> SEQUENCE: 3
ccaatgcatg gtatttcagg gagacactcc                                              30

<210> SEQ ID NO 4
<211> LENGTH: 30
<212> TYPE: DNA
<213> ORGANISM: Artificial sequence
<220> FEATURE:
<223> OTHER INFORMATION: Synthetic

<400> SEQUENCE: 4
cggctagctt ttagcatcag gtaagggctg                                              30

<210> SEQ ID NO 5
<211> LENGTH: 292
<212> TYPE: PRT
<213> ORGANISM: Artificial sequence
<220> FEATURE:
<223> OTHER INFORMATION: Synthetic

<400> SEQUENCE: 5

Met Leu Gln Asn Ser Ala Val Leu Leu Val Leu Val Ile Ser Ala Ser
 1               5                  10                  15

Ala Thr His Glu Ala Glu Gln Ser Arg Met His Gly Ile Ser Gly Arg
            20                  25                  30

His Ser Ile Thr Val Thr Thr Val Ala Ser Ala Gly Asn Ile Gly Glu
        35                  40                  45

Asp Gly Ile Leu Ser Cys Thr Phe Glu Pro Asp Ile Lys Leu Ser Asp
    50                  55                  60

Ile Val Ile Gln Trp Leu Lys Glu Gly Val Leu Gly Leu Val His Glu
65                  70                  75                  80

Phe Lys Glu Gly Lys Asp Glu Leu Ser Glu Gln Asp Glu Met Phe Arg
                85                  90                  95

Gly Arg Thr Ala Val Phe Ala Asp Gln Val Ile Val Gly Asn Ala Ser
            100                 105                 110

Leu Arg Leu Lys Asn Val Gln Leu Thr Asp Ala Gly Thr Tyr Lys Cys
        115                 120                 125

Tyr Ile Ile Thr Ser Lys Gly Lys Gly Asn Ala Asn Leu Glu Tyr Lys
    130                 135                 140

Thr Gly Ala Phe Ser Met Pro Glu Val Asn Val Asp Tyr Asn Ala Ser
145                 150                 155                 160

Ser Glu Thr Leu Arg Cys Glu Ala Pro Arg Trp Phe Pro Gln Pro Thr
                165                 170                 175

Val Val Trp Ala Ser Gln Val Asp Gln Gly Ala Asn Phe Ser Glu Val
            180                 185                 190

Ser Asn Thr Ser Phe Glu Leu Asn Ser Glu Asn Val Thr Met Lys Val
        195                 200                 205

Val Ser Val Leu Tyr Asn Val Thr Ile Asn Asn Thr Tyr Ser Cys Met

```
              210                 215                 220
Ile Glu Asn Asp Ile Ala Lys Ala Thr Gly Asp Ile Lys Val Thr Glu
225                 230                 235                 240

Ser Glu Ile Lys Arg Arg Ser His Leu Gln Leu Leu Asn Ser Lys Ala
            245                 250                 255

Ser Leu Cys Val Ser Ser Phe Phe Ala Ile Ser Trp Ala Leu Leu Pro
        260                 265                 270

Leu Ser Pro Tyr Leu Met Leu Lys Ala Ser His His His His His His
        275                 280                 285

His His His His
    290

<210> SEQ ID NO 6
<211> LENGTH: 33
<212> TYPE: DNA
<213> ORGANISM: Artificial sequence
<220> FEATURE:
<223> OTHER INFORMATION: Synthetic

<400> SEQUENCE: 6
ctttgtttaa acatgaagac attgcctgcc atg                           33

<210> SEQ ID NO 7
<211> LENGTH: 29
<212> TYPE: DNA
<213> ORGANISM: Artificial sequence
<220> FEATURE:
<223> OTHER INFORMATION: Synthetic

<400> SEQUENCE: 7
cggctagcac tcctcacaca tatggatgc                                29

<210> SEQ ID NO 8
<211> LENGTH: 29
<212> TYPE: DNA
<213> ORGANISM: Artificial sequence
<220> FEATURE:
<223> OTHER INFORMATION: Synthetic

<400> SEQUENCE: 8
cggctagcgg gtctgcttgc cacttcgtc                                29

<210> SEQ ID NO 9
<211> LENGTH: 289
<212> TYPE: PRT
<213> ORGANISM: Artificial sequence
<220> FEATURE:
<223> OTHER INFORMATION: Synthetic

<400> SEQUENCE: 9

Met Lys Thr Leu Pro Ala Met Leu Gly Thr Gly Lys Leu Phe Trp Val
1               5                   10                  15

Phe Phe Leu Ile Pro Tyr Leu Asp Ile Trp Asn Ile His Gly Lys Glu
            20                  25                  30

Ser Cys Asp Val Gln Leu Tyr Ile Lys Arg Gln Ser Glu His Ser Ile
        35                  40                  45

Leu Ala Gly Asp Pro Phe Glu Leu Glu Cys Pro Val Lys Tyr Cys Ala
    50                  55                  60

Asn Arg Pro His Val Thr Trp Cys Lys Leu Asn Gly Thr Thr Cys Val
65                  70                  75                  80

Lys Leu Glu Asp Arg Gln Thr Ser Trp Lys Glu Glu Lys Asn Ile Ser
```

```
                    85                  90                  95
Phe Phe Ile Leu His Phe Glu Pro Val Leu Pro Asn Asp Asn Gly Ser
                100                 105                 110
Tyr Arg Cys Ser Ala Asn Phe Gln Ser Asn Leu Ile Glu Ser His Ser
                115                 120                 125
Thr Thr Leu Tyr Val Thr Asp Val Lys Ser Ala Ser Glu Arg Pro Ser
                130                 135                 140
Lys Asp Glu Met Ala Ser Arg Pro Trp Leu Leu Tyr Ser Leu Leu Pro
145                 150                 155                 160
Leu Gly Gly Leu Pro Leu Leu Ile Thr Thr Cys Phe Cys Leu Phe Cys
                165                 170                 175
Cys Leu Arg Arg His Gln Gly Lys Gln Asn Glu Leu Ser Asp Thr Ala
                180                 185                 190
Gly Arg Glu Ile Asn Leu Val Asp Ala His Leu Lys Ser Glu Gln Thr
                195                 200                 205
Glu Ala Ser Thr Arg Gln Asn Ser Gln Val Leu Leu Ser Glu Thr Gly
                210                 215                 220
Ile Tyr Asp Asn Asp Pro Asp Leu Cys Phe Arg Met Gln Glu Gly Ser
225                 230                 235                 240
Glu Val Tyr Ser Asn Pro Cys Leu Glu Glu Asn Lys Pro Gly Ile Val
                245                 250                 255
Tyr Ala Ser Leu Asn His Ser Val Ile Gly Leu Asn Ser Arg Leu Ala
                260                 265                 270
Arg Asn Val Lys Glu Ala Pro Thr Glu Tyr Ala Ser Ile Cys Val Arg
                275                 280                 285
Ser

<210> SEQ ID NO 10
<211> LENGTH: 241
<212> TYPE: PRT
<213> ORGANISM: Artificial sequence
<220> FEATURE:
<223> OTHER INFORMATION: Synthetic

<400> SEQUENCE: 10

Met Lys Thr Leu Pro Ala Met Leu Gly Thr Gly Lys Leu Phe Trp Val
1               5                   10                  15
Phe Phe Leu Ile Pro Tyr Leu Asp Ile Trp Asn Ile His Gly Lys Glu
                20                  25                  30
Ser Cys Asp Val Gln Leu Tyr Ile Lys Arg Gln Ser Glu His Ser Ile
                35                  40                  45
Leu Ala Gly Asp Pro Phe Glu Leu Glu Cys Pro Val Lys Tyr Cys Ala
                50                  55                  60
Asn Arg Pro His Val Thr Trp Cys Lys Leu Asn Gly Thr Thr Cys Val
65                  70                  75                  80
Lys Leu Glu Asp Arg Gln Thr Ser Trp Lys Glu Lys Asn Ile Ser
                85                  90                  95
Phe Phe Ile Leu His Phe Glu Pro Val Leu Pro Asn Asp Asn Gly Ser
                100                 105                 110
Tyr Arg Cys Ser Ala Asn Phe Gln Ser Asn Leu Ile Glu Ser His Ser
                115                 120                 125
Thr Thr Leu Tyr Val Thr Gly Lys Gln Asn Glu Leu Ser Asp Thr Ala
                130                 135                 140
Gly Arg Glu Ile Asn Leu Val Asp Ala His Leu Lys Ser Glu Gln Thr
145                 150                 155                 160
```

```
Glu Ala Ser Thr Arg Gln Asn Ser Gln Val Leu Leu Ser Glu Thr Gly
                165                 170                 175

Ile Tyr Asp Asn Asp Pro Asp Leu Cys Phe Arg Met Gln Glu Gly Ser
            180                 185                 190

Glu Val Tyr Ser Asn Pro Cys Leu Glu Glu Asn Lys Pro Gly Ile Val
        195                 200                 205

Tyr Ala Ser Leu Asn His Ser Val Ile Gly Leu Asn Ser Arg Leu Ala
    210                 215                 220

Arg Asn Val Lys Glu Ala Pro Thr Glu Tyr Ala Ser Ile Cys Val Arg
225                 230                 235                 240

Ser
```

<210> SEQ ID NO 11
<211> LENGTH: 390
<212> TYPE: PRT
<213> ORGANISM: Artificial sequence
<220> FEATURE:
<223> OTHER INFORMATION: Synthetic

<400> SEQUENCE: 11

```
Met Lys Thr Leu Pro Ala Met Leu Gly Thr Gly Lys Leu Phe Trp Val
1               5                   10                  15

Phe Phe Leu Ile Pro Tyr Leu Asp Ile Trp Asn Ile His Gly Lys Glu
            20                  25                  30

Ser Cys Asp Val Gln Leu Tyr Ile Lys Arg Gln Ser Glu His Ser Ile
        35                  40                  45

Leu Ala Gly Asp Pro Phe Glu Leu Glu Cys Pro Val Lys Tyr Cys Ala
    50                  55                  60

Asn Arg Pro His Val Thr Trp Cys Lys Leu Asn Gly Thr Thr Cys Val
65                  70                  75                  80

Lys Leu Glu Asp Arg Gln Thr Ser Trp Lys Glu Glu Lys Asn Ile Ser
                85                  90                  95

Phe Phe Ile Leu His Phe Glu Pro Val Leu Pro Asn Asp Asn Gly Ser
            100                 105                 110

Tyr Arg Cys Ser Ala Asn Phe Gln Ser Asn Leu Ile Glu Ser His Ser
        115                 120                 125

Thr Thr Leu Tyr Val Thr Asp Val Lys Ser Ala Ser Glu Arg Pro Ser
    130                 135                 140

Lys Asp Glu Met Ala Ser Arg Pro Ala Ser Glu Asn Leu Tyr Phe Gln
145                 150                 155                 160

Gly Pro Arg Gly Pro Thr Ile Lys Pro Cys Pro Pro Cys Lys Cys Pro
                165                 170                 175

Ala Pro Asn Leu Leu Gly Gly Pro Ser Val Phe Ile Phe Pro Pro Lys
            180                 185                 190

Ile Lys Asp Val Leu Met Ile Ser Leu Ser Pro Ile Val Thr Cys Val
        195                 200                 205

Val Val Asp Val Ser Glu Asp Pro Asp Val Gln Ile Ser Trp Phe Val
    210                 215                 220

Asn Asn Val Glu Val His Thr Ala Gln Thr Gln Thr His Arg Glu Asp
225                 230                 235                 240

Tyr Asn Ser Thr Leu Arg Val Val Ser Ala Leu Pro Ile Gln His Gln
                245                 250                 255

Asp Trp Met Ser Gly Lys Glu Phe Lys Cys Lys Val Asn Asn Lys Asp
            260                 265                 270
```

```
Leu Pro Ala Pro Ile Glu Arg Thr Ile Ser Lys Pro Lys Gly Val Arg
            275                 280                 285

Ala Pro Gln Val Tyr Val Leu Pro Pro Glu Glu Glu Met Thr Lys
        290                 295                 300

Lys Gln Val Thr Leu Thr Cys Met Val Thr Asp Phe Met Pro Glu Asp
305                 310                 315                 320

Ile Tyr Val Glu Trp Thr Asn Asn Gly Lys Thr Glu Leu Asn Tyr Lys
                325                 330                 335

Asn Thr Glu Pro Val Leu Asp Ser Asp Gly Ser Tyr Phe Met Tyr Ser
            340                 345                 350

Lys Leu Arg Val Glu Lys Asn Trp Val Glu Arg Asn Ser Tyr Ser Cys
        355                 360                 365

Ser Val Val His Glu Gly Leu His Asn His Thr Thr Lys Ser Phe
370                 375                 380

Ser Arg Thr Pro Gly Lys
385                 390

<210> SEQ ID NO 12
<211> LENGTH: 614
<212> TYPE: PRT
<213> ORGANISM: Artificial sequence
<220> FEATURE:
<223> OTHER INFORMATION: Synthetic

<400> SEQUENCE: 12

Met Asn Arg Thr Trp Pro Arg Arg Ile Trp Gly Ser Ser Gln Asp Glu
1               5                   10                  15

Ala Glu Leu Ile Arg Glu Asp Ile Gln Gly Ala Leu His Asn Tyr Arg
                20                  25                  30

Ser Gly Arg Gly Glu Arg Arg Ala Ala Ala Leu Arg Ala Thr Gln Glu
            35                  40                  45

Glu Leu Gln Arg Asp Arg Ser Pro Ala Ala Glu Thr Pro Pro Leu Gln
        50                  55                  60

Arg Arg Pro Ser Val Arg Ala Val Ile Ser Thr Val Glu Arg Gly Ala
65                  70                  75                  80

Gly Arg Gly Arg Pro Gln Ala Lys Pro Ile Pro Glu Ala Glu Glu Ala
                85                  90                  95

Gln Arg Pro Glu Pro Val Gly Thr Ser Ser Asn Ala Asp Ser Ala Ser
            100                 105                 110

Pro Asp Leu Gly Pro Arg Gly Pro Asp Leu Val Val Leu Gln Ala Glu
        115                 120                 125

Arg Glu Val Asp Ile Leu Asn His Val Phe Asp Asp Val Glu Ser Phe
130                 135                 140

Val Ser Arg Leu Gln Lys Ser Ala Glu Ala Ala Arg Val Leu Glu His
145                 150                 155                 160

Arg Glu Arg Gly Arg Arg Ser Arg Arg Ala Ala Gly Glu Gly Leu
                165                 170                 175

Leu Thr Leu Arg Ala Lys Pro Pro Ser Glu Ala Glu Tyr Thr Asp Val
            180                 185                 190

Leu Gln Lys Ile Lys Tyr Ala Phe Ser Leu Leu Ala Arg Leu Arg Gly
        195                 200                 205

Asn Ile Ala Asp Pro Ser Ser Pro Glu Leu Leu His Phe Leu Phe Gly
210                 215                 220

Pro Leu Gln Met Ile Val Asn Thr Ser Gly Gly Pro Glu Phe Ala Ser
225                 230                 235                 240
```

-continued

```
Ser Val Arg Arg Pro His Leu Thr Ser Asp Ala Val Ala Leu Leu Arg
            245                 250                 255

Asp Asn Val Thr Pro Arg Glu Asn Glu Leu Trp Thr Ser Leu Gly Asp
            260                 265                 270

Ser Trp Thr Arg Pro Gly Leu Glu Leu Ser Pro Glu Glu Gly Pro Pro
            275                 280                 285

Tyr Arg Pro Glu Phe Phe Ser Gly Trp Glu Pro Pro Val Thr Asp Pro
            290                 295                 300

Gln Ser Arg Ala Trp Glu Asp Pro Val Glu Lys Gln Leu Gln His Glu
305                 310                 315                 320

Arg Arg Arg Arg Gln Gln Ser Ala Pro Gln Val Ala Val Asn Gly His
            325                 330                 335

Arg Asp Leu Glu Pro Glu Ser Glu Pro Gln Leu Glu Ser Glu Thr Ala
            340                 345                 350

Gly Lys Trp Val Leu Cys Asn Tyr Asp Phe Gln Ala Arg Asn Ser Ser
            355                 360                 365

Glu Leu Ser Val Lys Gln Arg Asp Val Leu Glu Val Leu Asp Asp Ser
        370                 375                 380

Arg Lys Trp Trp Lys Val Arg Asp Pro Ala Gly Gln Glu Gly Tyr Val
385                 390                 395                 400

Pro Tyr Asn Ile Leu Thr Pro Tyr Pro Gly Pro Arg Leu His His Ser
            405                 410                 415

Gln Ser Pro Ala Arg Ser Leu Asn Ser Thr Pro Pro Pro Pro Ala
            420                 425                 430

Pro Ala Pro Ala Pro Pro Ala Leu Ala Arg Pro Arg Trp Asp Arg
        435                 440                 445

Pro Arg Trp Asp Ser Cys Asp Ser Leu Asn Gly Leu Asp Pro Ser Glu
            450                 455                 460

Lys Glu Lys Phe Ser Gln Met Leu Ile Val Asn Glu Glu Leu Gln Ala
465                 470                 475                 480

Arg Leu Ala Gln Gly Arg Ser Gly Pro Ser Arg Ala Val Pro Gly Pro
            485                 490                 495

Arg Ala Pro Glu Pro Gln Leu Ser Pro Gly Ser Asp Ala Ser Glu Val
            500                 505                 510

Arg Ala Trp Leu Gln Ala Lys Gly Phe Ser Ser Gly Thr Val Asp Ala
            515                 520                 525

Leu Gly Val Leu Thr Gly Ala Gln Leu Phe Ser Leu Gln Lys Glu Glu
        530                 535                 540

Leu Arg Ala Val Ser Pro Glu Glu Gly Ala Arg Val Tyr Ser Gln Val
545                 550                 555                 560

Thr Val Gln Arg Ser Leu Leu Glu Asp Lys Glu Lys Val Ser Glu Leu
            565                 570                 575

Glu Ala Val Met Glu Lys Gln Lys Lys Val Glu Gly Glu Val Glu
            580                 585                 590

Met Glu Val Ile Asp Pro Ala Phe Leu Tyr Lys Val Val Arg Trp Ala
            595                 600                 605

His His His His His His
    610
```

<210> SEQ ID NO 13
<211> LENGTH: 309
<212> TYPE: PRT
<213> ORGANISM: Artificial sequence
<220> FEATURE:
<223> OTHER INFORMATION: Synthetic

<400> SEQUENCE: 13

```
Met Leu Gln Asn Ser Ala Val Leu Val Leu Val Ile Ser Ala Ser
1               5                   10                  15

Ala Thr Met Ala Ser Leu Gly Gln Ile Leu Phe Trp Ser Ile Ile Ser
            20                  25                  30

Ile Ile Ile Ile Leu Ala Gly Ala Ile Ala Leu Ile Ile Gly Phe Gly
        35                  40                  45

Ile Ser Gly Arg His Ser Ile Thr Val Thr Thr Val Ala Ser Ala Gly
    50                  55                  60

Asn Ile Gly Glu Asp Gly Ile Gln Ser Cys Thr Phe Glu Pro Asp Ile
65                  70                  75                  80

Lys Leu Ser Asp Ile Val Ile Gln Trp Leu Lys Glu Gly Val Leu Gly
                85                  90                  95

Leu Val His Glu Phe Lys Glu Gly Lys Asp Glu Leu Ser Glu Gln Asp
            100                 105                 110

Glu Met Phe Arg Gly Arg Thr Ala Val Phe Ala Asp Gln Val Ile Val
            115                 120                 125

Gly Asn Ala Ser Leu Arg Leu Lys Asn Val Gln Leu Thr Asp Ala Gly
130                 135                 140

Thr Tyr Lys Cys Tyr Ile Ile Thr Ser Lys Gly Lys Gly Asn Ala Asn
145                 150                 155                 160

Leu Glu Tyr Lys Thr Gly Ala Phe Ser Met Pro Glu Val Asn Val Asp
                165                 170                 175

Tyr Asn Ala Ser Ser Glu Thr Leu Arg Cys Glu Ala Pro Arg Trp Phe
            180                 185                 190

Pro Gln Pro Thr Val Val Trp Ala Ser Gln Val Asp Gln Gly Ala Asn
            195                 200                 205

Phe Ser Glu Val Ser Asn Thr Ser Phe Glu Leu Asn Ser Glu Asn Val
210                 215                 220

Thr Met Lys Val Val Ser Val Leu Tyr Asn Val Thr Ile Asn Asn Thr
225                 230                 235                 240

Tyr Ser Cys Met Ile Glu Asn Asp Ile Ala Lys Ala Thr Gly Asp Ile
                245                 250                 255

Lys Val Thr Glu Ser Glu Ile Lys Arg Arg Ser His Leu Gln Leu Leu
            260                 265                 270

Asn Ser Lys Ala Ser Leu Cys Val Ser Ser Phe Phe Ala Ile Ser Trp
            275                 280                 285

Ala Leu Leu Pro Leu Ser Pro Tyr Leu Met Leu Lys Tyr Pro Tyr Asp
    290                 295                 300

Val Pro Asp Tyr Ala
305
```

<210> SEQ ID NO 14
<211> LENGTH: 19
<212> TYPE: RNA
<213> ORGANISM: Artificial sequence
<220> FEATURE:
<223> OTHER INFORMATION: Synthetic

<400> SEQUENCE: 14
gguguuuuag gcuuggucc                                              19

<210> SEQ ID NO 15
<211> LENGTH: 19
<212> TYPE: RNA

-continued

```
<213> ORGANISM: Artificial sequence
<220> FEATURE:
<223> OTHER INFORMATION: Synthetic

<400> SEQUENCE: 15
cucacagaug cuggcaccu                                            19

<210> SEQ ID NO 16
<211> LENGTH: 19
<212> TYPE: RNA
<213> ORGANISM: Artificial sequence
<220> FEATURE:
<223> OTHER INFORMATION: Synthetic

<400> SEQUENCE: 16
gguugugucu gugcucuac                                            19

<210> SEQ ID NO 17
<211> LENGTH: 19
<212> TYPE: RNA
<213> ORGANISM: Artificial sequence
<220> FEATURE:
<223> OTHER INFORMATION: Synthetic

<400> SEQUENCE: 17
ccgugcuccu ggggcuggg                                            19

<210> SEQ ID NO 18
<211> LENGTH: 19
<212> TYPE: RNA
<213> ORGANISM: Artificial sequence
<220> FEATURE:
<223> OTHER INFORMATION: Synthetic

<400> SEQUENCE: 18
uucuccgaac gugucacgu                                            19

<210> SEQ ID NO 19
<211> LENGTH: 19
<212> TYPE: RNA
<213> ORGANISM: Artificial sequence
<220> FEATURE:
<223> OTHER INFORMATION: Synthetic

<400> SEQUENCE: 19
ggaguuggau cucucagaa                                            19
```

OVR110 ANTIBODY COMPOSITIONS AND METHODS OF USE

This patent application claims the benefit of priority from U.S. Provisional patent application Ser. No. 60/556,464, filed Mar. 25, 2004, U.S. Provisional patent application Ser. No. 60/552,959, filed Mar. 12, 2004 and U.S. Provisional patent application Ser. No. 60/469,555, filed May 9, 2003, each of which is herein incorporated by reference in its entirety.

FIELD OF THE INVENTION

The present invention relates to anti-Ovr110 antibody compositions and methods of killing Ovr110-expressing ovarian, pancreatic, lung or breast cancers cells.

BACKGROUND OF THE INVENTION

Cancer of the ovaries is the fourth-most common cause of cancer death in women in the United States, with more than 23,000 new cases and roughly 14,000 deaths predicted for the year 2001. Shridhar, V. et al., Cancer Res. 61(15): 5895-904 (2001); Memarzadeh, S. & Berek, J. S., J. Reprod. Med. 46(7): 621-29 (2001). The incidence of ovarian cancer is of serious concern worldwide, with an estimated 191,000 new cases predicted annually. Runnebaum, I. B. & Stickeler, E., J. Cancer Res. Clin. Oncol. 127(2): 73-79 (2001). Unfortunately, women with ovarian cancer are typically asymptomatic until the disease has metastasized. Because effective screening for ovarian cancer is not available, roughly 70% of women diagnosed have an advanced stage of the cancer with a five-year survival rate of ~25-30%. Memarzadeh, S. & Berek, J. S., supra; Nunns, D. et al., Obstet. Gynecol. Surv. 55(12): 746-51. Conversely, women diagnosed with early stage ovarian cancer enjoy considerably higher survival rates. Werness, B. A. & Eltabbakh, G. H., Int'l. J. Gynecol. Pathol. 20(1): 48-63 (2001). Although our understanding of the etiology of ovarian cancer is incomplete, the results of extensive research in this area point to a combination of age, genetics, reproductive, and dietary/environmental factors. Age is a key risk factor in the development of ovarian cancer: while the risk for developing ovarian cancer before the age of 30 is slim, the incidence of ovarian cancer rises linearly between ages 30 to 50, increasing at a slower rate thereafter, with the highest incidence being among septagenarian women. Jeanne M. Schilder et al., Heriditary Ovarian Cancer: Clinical Syndromes and Management, in *Ovarian Cancer* 182 (Stephen C. Rubin & Gregory P. Sutton eds., 2d ed. 2001).

With respect to genetic factors, a family history of ovarian cancer is the most significant risk factor in the development of the disease, with that risk depending on the number of affected family members, the degree of their relationship to the woman, and which particular first degree relatives are affected by the disease. Id. Mutations in several genes have been associated with ovarian cancer, including BRCA1 and BRCA2, both of which play a key role in the development of breast cancer, as well as hMSH2 and hMLH1, both of which are associated with hereditary non-polyposis colon cancer. Katherine Y. Look, Epidemiology, Etiology, and Screening of Ovarian Cancer, in *Ovarian Cancer* 169, 171-73 (Stephen C. Rubin & Gregory P. Sutton eds., 2d ed. 2001). BRCA1, located on chromosome 17, and BRCA2, located on chromosome 13, are tumor suppressor genes implicated in DNA repair; mutations in these genes are linked to roughly 10% of ovarian cancers. Id. at 171-72; Schilder et al., supra at 185-86. hMSH2 and hMLH1 are associated with DNA mismatch repair, and are located on chromosomes 2 and 3, respectively; it has been reported that roughly 3% of hereditary ovarian carcinomas are due to mutations in these genes. Look, supra at 173; Schilder et al., supra at 184, 188-89.

Reproductive factors have also been associated with an increased or reduced risk of ovarian cancer. Late menopause, nulliparity, and early age at menarche have all been linked with an elevated risk of ovarian cancer. Schilder et al., supra at 182. One theory hypothesizes that these factors increase the number of ovulatory cycles over the course of a woman's life, leading to "incessant ovulation," which is thought to be the primary cause of mutations to the ovarian epithelium. Id.; Laura J. Havrilesky & Andrew Berchuck, Molecular Alterations in Sporadic Ovarian Cancer, in *Ovarian Cancer* 25 (Stephen C. Rubin & Gregory P. Sutton eds., 2d ed. 2001). The mutations may be explained by the fact that ovulation results in the destruction and repair of that epithelium, necessitating increased cell division, thereby increasing the possibility that an undetected mutation will occur. Id. Support for this theory may be found in the fact pregnancy, lactation, and the use of oral contraceptives, all of which suppress ovulation, confer a protective effect with respect to developing ovarian cancer. Id.

Among dietary/environmental factors, there would appear to be an association between high intake of animal fat or red meat and ovarian cancer, while the antioxidant Vitamin A, which prevents free radical formation and also assists in maintaining normal cellular differentiation, may offer a protective effect Look, supra at 169. Reports have also associated asbestos and hydrous magnesium trisilicate (talc), the latter of which may be present in diaphragms and sanitary napkins. Id. at 169-70.

Current screening procedures for ovarian cancer, while of some utility, are quite limited in their diagnostic ability, a problem that is particularly acute at early stages of cancer progression when the disease is typically asymptomatic yet is most readily treated. Walter J. Burdette, *Cancer: Etiology, Diagnosis, and Treatment* 166 (1998); Memarzadeh & Berek, supra; Runnebaum & Stickeler, supra; Werness & Eltabbakh, supra. Commonly used screening tests include biannual rectovaginal pelvic examination, radioimmunoassay to detect the CA-125 serum tumor marker, and transvaginal ultrasonography. Burdette, supra at 166.

Pelvic examination has failed to yield adequate numbers of early diagnoses, and the other methods are not sufficiently accurate. Id. One study reported that only 15% of patients who suffered from ovarian cancer were diagnosed with the disease at the time of their pelvic examination. Look, supra at 174. Moreover, the CA-125 test is prone to giving false positives in pre-menopausal women and has been reported to be of low predictive value in post-menopausal women. Id. at 174-75. Although transvaginal ultrasonography is now the preferred procedure for screening for ovarian cancer, it is unable to distinguish reliably between benign and malignant tumors, and also cannot locate primary peritoneal malignancies or ovarian cancer if the ovary size is normal. Schilder et al., supra at 194-95. While genetic testing for mutations of the BRCA1, BRCA2, hMSH2, and hMLH1 genes is now available, these tests may be too costly for some patients and may also yield false negative or indeterminate results. Schilder et al., supra at 191-94.

Elevated serum CA125 levels have been associated with an increased incidence of ovarian cancer in a prospective cohort study. Jacobs, I. J., et al., Risk of diagnosis of ovarian cancer after raised serum CA 125 concentration: a prospective cohort study. Bmj, 1996. 313(7069): p. 1355-8. CA125 is a tumor-associated antigen that has been used clinically to monitor patients with epithelial ovarian carcinomas. About 9,320 postmenopausal women underwent an initial screen and an average of 2.8 yearly screens with the CA125 assay and were followed for an average of 6.8 years. Forty-nine cancers were identified. A serum CA125 concentration of at least 30 U/mL was associated with a relative risk of 35.9 (95% confidence interval (CI) 18.3-70.4) during the first year after the screen, and a relative risk of 14.3 (95% CI 8.5-24.4) during the 5 years after the screen. At a CA125 concentration of 100 U/mL, the relative risks were 204.8 and 74.5, respectively. Women with CA125 levels below 30 U/mL had risks of 0.13 and 0.54, respectively.

Other markers of interest are HE4 and mesothelin, see Urban et al. Ovarian cancer screening Hematol Oncol Clin North Am. 2003 August; 17(4):989-1005; Hellstrom et al. The HE4 (WFDC2) protein is a biomarker for ovarian carcinoma, Cancer Res. 2003 Jul. 1; 63(13):3695-700; Ordonez, Application of mesothelin immunostaining in tumor diagnosis, Am J Surg Pathol. 2003 November, 27(11):1418-28.

The staging of ovarian cancer, which is accomplished through surgical exploration, is crucial in determining the course of treatment and management of the disease. *AJCC Cancer Staging Handbook* 187 (Irvin D. Fleming et al. eds., 5th ed. 1998); Burdette, supra at 170; Memarzadeh & Berek, supra; Shridhar et al., supra. Staging is performed by reference to the classification system developed by the International Federation of Gynecology and Obstetrics. David H. Moore, Primary Surgical Management of Early Epithelial Ovarian Carcinoma, in *Ovarian Cancer* 203 (Stephen C. Rubin & Gregory P. Sutton eds., 2d ed. 2001); Fleming et al. eds., supra at 188. Stage I ovarian cancer is characterized by tumor growth that is limited to the ovaries and is comprised of three substages. Id. In substage IA, tumor growth is limited to one ovary, there is no tumor on the external surface of the ovary, the ovarian capsule is intact, and no malignant cells are present in ascites or peritoneal washings. Id. Substage IB is identical to A1, except that tumor growth is limited to both ovaries. Id. Substage IC refers to the presence of tumor growth limited to one or both ovaries, and also includes one or more of the following characteristics: capsule rupture, tumor growth on the surface of one or both ovaries, and malignant cells present in ascites or peritoneal washings. Id.

Stage II ovarian cancer refers to tumor growth involving one or both ovaries, along with pelvic extension. Id. Substage IIA involves extension and/or implants on the uterus and/or fallopian tubes, with no malignant cells in the ascites or peritoneal washings, while substage IIB involves extension into other pelvic organs and tissues, again with no malignant cells in the ascites or peritoneal washings. Id. Substage IIC involves pelvic extension as in IIA or IIB, but with malignant cells in the ascites or peritoneal washings. Id.

Stage III ovarian cancer involves tumor growth in one or both ovaries, with peritoneal metastasis beyond the pelvis confirmed by microscope and/or metastasis in the regional lymph nodes. Id. Substage IIIA is characterized by microscopic peritoneal metastasis outside the pelvis, with substage IIIB involving macroscopic peritoneal metastasis outside the pelvis 2 cm or less in greatest dimension. Id. Substage IIIC is identical to IIIB, except that the metastasis is greater than 2 cm in greatest dimension and may include regional lymph node metastasis. Id. Lastly, Stage IV refers to the presence distant metastasis, excluding peritoneal metastasis. Id.

While surgical staging is currently the benchmark for assessing the management and treatment of ovarian cancer, it suffers from considerable drawbacks, including the invasiveness of the procedure, the potential for complications, as well as the potential for inaccuracy. Moore, supra at 206-208, 213. In view of these limitations, attention has turned to developing alternative staging methodologies through understanding differential gene expression in various stages of ovarian cancer and by obtaining various biomarkers to help better assess the progression of the disease. Vartiainen, J. et al., Int'l J. Cancer, 95(5): 313-16 (2001); Shridhar et al. supra; Baekelandt, M. et al., J. Clin. Oncol. 18(22): 3775-81.

The treatment of ovarian cancer typically involves a multiprong attack, with surgical intervention serving as the foundation of treatment. Dennis S. Chi & William J. Hoskins, Primary Surgical Management of Advanced Epithelial Ovarian Cancer, in *Ovarian Cancer* 241 (Stephen C. Rubin & Gregory P. Sutton eds., 2d ed. 2001). For example, in the case of epithelial ovarian cancer, which accounts for ~90% of cases of ovarian cancer, treatment typically consists of: (1) cytoreductive surgery, including total abdominal hysterectomy, bilateral salpingo-oophorectomy, omentectomy, and lymphadenectomy, followed by (2) adjuvant chemotherapy with paclitaxel and either cisplatin or carboplatin. Eltabbakh, G. H. & Awtrey, C. S., Expert Op. Pharmacother. 2(10): 109-24. Despite a clinical response rate of 80% to the adjuvant therapy, most patients experience tumor recurrence within three years of treatment Id. Certain patients may undergo a second cytoreductive surgery and/or second-line chemotherapy. Memarzadeh & Berek, supra.

From the foregoing, it is clear that procedures used for detecting, diagnosing, monitoring, staging, prognosticating, and preventing the recurrence of ovarian cancer are of critical importance to the outcome of the patient. Moreover, current procedures, while helpful in each of these analyses, are limited by their specificity, sensitivity, invasiveness, and/or their cost. As such, highly specific and sensitive procedures that would operate by way of detecting novel markers in cells, tissues, or bodily fluids, with minimal invasiveness and at a reasonable cost, would be highly desirable.

Breast cancer, also referred to as mammary tumor cancer, is the second most common cancer among women, accounting for a third of the cancers diagnosed in the United States. One in nine women will develop breast cancer in her lifetime and about 192,000 new cases of breast cancer are diagnosed annually with about 42,000 deaths. Bevers, Primary Prevention of Breast Cancer, in *Breast Cancer* 20-54 (Kelly K Hunt et al., ed., 2001); Kochanek et al., 49 Nat'l. Vital Statistics Reports 1, 14 (2001). Breast cancer is extremely rare in women younger than 20 and is very rare in women under 30. The incidence of breast cancer rises with age and becomes significant by age 50. White Non-Hispanic women have the highest incidence rate for breast cancer and Korean women have the lowest. Increased prevalence of the genetic mutations BRCA1 and BRCA2 that promote breast and other cancers are found in Ashkenazi Jews. African American women have the highest mortality rate for breast cancer among these same groups (31 per 100,000), while Chinese women have the lowest at 11 per 100,000. Although men can get breast cancer, this is extremely rare. (American Cancer Society Website: cancer with the extension .org of the world wide web). With the exception of those cases with associated genetic factors, precise causes of breast cancer are not known.

In the treatment of breast cancer, there is considerable emphasis on detection and risk assessment because early and accurate staging of breast cancer has a significant impact on survival. For example, breast cancer detected at an early stage (stage T0, discussed below) has a five-year survival rate of 92%. Conversely, if the cancer is not detected until a late stage (i.e., stage T4 (V)), the five-year survival rate is reduced to 13%. *AJCC Cancer Staging Handbook* pp. 164-65 (Irvin D. Fleming et al. eds., 5th ed. 1998). Some detection techniques, such as mammography and biopsy, involve increased discomfort, expense, and/or radiation, and are only prescribed only to patients with an increased risk of breast cancer.

Current methods for predicting or detecting breast cancer risk are not optimal. One method for predicting the relative risk of breast cancer is by examining a patient's risk factors and pursuing aggressive diagnostic and treatment regiments for high risk patients. A patient's risk of breast cancer has been positively associated with increasing age, nulliparity, family history of breast cancer, personal history of breast cancer, early menarche, late menopause, late age of first full term pregnancy, prior proliferative breast disease, irradiation of the breast at an early age and a personal history of malignancy. Lifestyle factors such as fat consumption, alcohol consumption, education, and socioeconomic status have also been associated with an increased incidence of breast cancer although a direct cause and effect relationship has not been established. While these risk factors are statistically significant, their weak association with breast cancer limited their usefulness. Most women who develop breast cancer have none of the risk factors listed above, other than the risk that comes with growing older. NIH Publication No. 00-1556 (2000).

Current screening methods for detecting cancer, such as breast self exam, ultrasound, and mammography have drawbacks that reduce their effectiveness or prevent their widespread adoption. Breast self exams, while useful, are unreliable for the detection of breast cancer in the initial stages where the tumor is small and difficult to detect by palpation. Ultrasound measurements require skilled operators at an increased expense. Mammography, while sensitive, is subject to over diagnosis in the detection of lesions that have questionable malignant potential. There is also the fear of the radiation used in mammography because prior chest radiation is a factor associated with an increase incidence of breast cancer.

At this time, there are no adequate methods of breast cancer prevention. The current methods of breast cancer prevention involve prophylactic mastectomy (mastectomy performed before cancer diagnosis) and chemoprevention (chemotherapy before cancer diagnosis), which are drastic measures that limit their adoption even among women with, increased risk of breast cancer. Bevers, supra.

A number of genetic markers have been associated with breast cancer. Examples of these markers include carcinoembryonic antigen (CEA) (Mughal et al., JAMA 249:1881 (1983)), MUC-1 (Frische and Liu, J. Clin. Ligand 22:320 (2000)), HER-2/neu (Haris et al., Proc. Am. Soc. Clin. Oncology 15:A96 (1996)), uPA, PAI-1, LPA, LPC, RAK and BRCA (Esteva and Fritsche, Serum and Tissue Markers for Breast Cancer, in *Breast Cancer*, 286-308 (2001)). These markers have problems with limited sensitivity, low correlation, and false negatives, which limit their use for initial diagnosis. For example, while the BRCA1 gene mutation is useful as an indicator of an increased risk for breast cancer, it has limited use in cancer diagnosis because only 6.2% of breast cancers are BRCA1 positive. Malone et al., JAMA 279:922 (1998). See also, Mewman et al., JAMA 279:915 (1998) (correlation of only 3.3%).

There are four primary classifications of breast cancer varying by the site of origin and the extent of disease development.

I. Ductal carcinoma in situ (DCIS): Malignant transformation of ductal epithelial cells that remain in their normal position. DCIS is a purely localized disease, incapable of metastasis.

II. Invasive ductal carcinoma (IDC): Malignancy of the ductal epithelial cells breaking through the basal membrane and into the supporting tissue of the breast. IDC may eventually spread else where in the body.

III. Lobular carcinoma in situ (LCIS): Malignancy arising in a single lobule of the breast that fail to extend through the lobule wall, it generally remains localized.

IV. Infiltrating lobular carcinoma (ILC): Malignancy arising in a single lobule of the breast and invading directly through the lobule wall into adjacent tissues. By virtue of its invasion beyond the lobule wall, ILC may penetrate lymphatics and blood vessels and spread to distant sites.

For purpose of determining prognosis and treatment, these four breast cancer types have been staged according to the size of the primary tumor (T), the involvement of lymph nodes (N), and the presence of metastasis (M). Although DCIS by definition represents localized stage I disease, the other forms of breast cancer may range from stage II to stage IV. There are additional prognostic factors that further serve to guide surgical and medical intervention. The most common ones are total number of lymph nodes involved, ER (estrogen receptor) status, Her2/neu receptor status and histologic grades.

Breast cancers are diagnosed into the appropriate stage categories recognizing that different treatments are more effective for different stages of cancer. Stage TX indicates that primary tumor cannot be assessed (i.e., tumor was removed or breast tissue was removed). Stage T0 is characterized by abnormalities such as hyperplasia but with no evidence of primary tumor. Stage Tis is characterized by carcinoma in situ, intraductal carcinoma, lobular carcinoma in situ, or Paget's disease of the nipple with no tumor. Stage T1 (I) is characterized as having a tumor of 2 cm or less in the greatest dimension. Within stage T1, Tmic indicates microinvasion of 0.1 cm or less, T1a indicates a tumor of between 0.1 to 0.5 cm, T1b indicates a tumor of between 0.5 to 1 cm, and T1c indicates tumors of between 1 cm to 2 cm. Stage T2 (II) is characterized by tumors from 2 cm to 5 cm in the greatest dimension. Tumors greater than 5 cm in size are classified as stage T3 (III). Stage T4 (IV) indicates a tumor of any size with extension to the chest wall or skin. Within stage T4, T4a indicates extension of the tumor to the chess wall, T4b indicates edema or ulceration of the skin of the breast or satellite skin nodules confined to the same breast, T4c indicates a combination of T4a and T4b, and T4d indicates inflammatory carcinoma. *AJCC Cancer Staging Handbook* pp. 159-70 (Irvin D. Fleming et al. eds., 5$^{th}$ ed. 1998). In addition to standard staging, breast tumors may be classified according to their estrogen receptor and progesterone receptor protein status. Fisher et al., Breast Cancer Research and Treatment 7:147 (1986). Additional pathological status, such as HER2/neu status may also be useful. Thor et al., J. Nat'l. Cancer Inst. 90:1346 (1998); Paik et al., J. Nat'l. Cancer Inst. 90:1361 (1998); Hutchins et al., Proc. Am. Soc. Clin. Oncology 17:A2 (1998); and Simpson et al., J. Clin. Oncology 18:2059 (2000).

In addition to the staging of the primary tumor, breast cancer metastasizes to regional lymph nodes may be staged. Stage NX indicates that the lymph nodes cannot be assessed (e.g., previously removed). Stage N0 indicates no regional lymph node metastasis. Stage N1 indicates metastasis to movable ipsilateral axillary lymph nodes. Stage N2 indicates metastasis to ipsilateral axillary lymph nodes fixed to one another or to other structures. Stage N3 indicates metastasis to ipsilateral internal mammary lymph nodes. Id.

Stage determination has potential prognostic value and provides criteria for designing optimal therapy. Simpson et al., J. Clin. Oncology 18:2059 (2000). Generally, pathological staging of breast cancer is preferable to clinical staging because the former gives a more accurate prognosis. However, clinical staging would be preferred if it were as accurate as pathological staging because it does not depend on an invasive procedure to obtain tissue for pathological evaluation. Staging of breast cancer would be improved by detecting new markers in cells, tissues, or bodily fluids that could differentiate between different stages of invasion. Progress in this field will allow more rapid and reliable method for treating breast cancer patients.

Treatment of breast cancer is generally decided after an accurate staging of the primary tumor. Primary treatment options include breast conserving therapy (lumpectomy, breast irradiation, and surgical staging of the axilla), and modified radical mastectomy. Additional treatments include chemotherapy, regional irradiation, and, in extreme cases, terminating estrogen production by ovarian ablation.

Until recently, the customary treatment for all breast cancer was mastectomy. Fonseca et al., Annals of Internal Medicine 127:1013 (1997). However, recent data indicate that less radical procedures may be equally effective, in terms of survival, for early stage breast cancer. Fisher et al., J. of Clinical Oncology 16:441 (1998). The treatment options for a patient with early stage breast cancer (i.e., stage Tis) may be breast-sparing surgery followed by localized radiation therapy at the breast. Alternatively, mastectomy optionally coupled with radiation or breast reconstruction may be employed. These treatment methods are equally effective in the early stages of breast cancer.

Patients with stage I and stage II breast cancer require surgery with chemotherapy and/or hormonal therapy. Surgery is of limited use in Stage III and stage IV patients. Thus, these patients are better candidates for chemotherapy and radiation therapy with surgery limited to biopsy to permit initial staging or subsequent restaging because cancer is rarely curative at this stage of the disease. *AJCC Cancer Staging Handbook* 84, ¶. 164-65 (Irvin D. Fleming et al. eds., 5$^{th}$ ed. 1998).

In an effort to provide more treatment options to patients, efforts are underway to define an earlier stage of breast cancer with low recurrence that could be treated with lumpectomy without postoperative radiation treatment. While a number of attempts have been made to classify early stage breast cancer, no consensus recommendation on postoperative radiation treatment has been obtained from these studies. Page et al., Cancer 75:1219 (1995); Fisher et al., Cancer 75:1223 (1995); Silverstein et al., Cancer 77:2267 (1996).

As discussed above, each of the methods for diagnosing and staging ovarian, pancreatic, lung or breast cancer is limited by the technology employed. Accordingly, there is need for sensitive molecular and cellular markers for the detection of ovarian, pancreatic, lung or breast cancer. There is a need for molecular markers for the accurate staging, including clinical and pathological staging, of ovarian, pancreatic, lung or breast cancers to optimize treatment methods. Finally, there is a need for sensitive molecular and cellular markers to monitor the progress of cancer treatments, including markers that can detect recurrence of ovarian, pancreatic, lung or breast cancers following remission.

The present invention provides alternative methods of treating ovarian, pancreatic, lung or breast cancer that overcome the limitations of conventional therapeutic methods as well as offer additional advantages that will be apparent from the detailed description below.

SUMMARY OF THE INVENTION

This invention is directed to an isolated Ovr110 antibody that binds to Ovr110 on a mammalian cell in vivo. The invention is further directed to an isolated Ovr110 antibody that internalizes upon binding to Ovr110 on a mammalian cell in vivo. The antibody may be a monoclonal antibody. Alternatively, the antibody is an antibody fragment or a chimeric or a humanized antibody. The monoclonal antibody may be produced by a hybridoma selected from the group of hybridomas deposited under American Type Culture Collection accession number PTA-5180, PTA-5855, PTA-5856 and PTA-5884.

The antibody may compete for binding to the same epitope as the epitope bound by the monoclonal antibody produced by a hybridoma selected from the group of hybridomas deposited under the American Type Culture Collection accession number PTA-5180, PTA-5855, PTA-5856 and PTA-5884.

The invention is also directed to conjugated antibodies. They may be conjugated to a growth inhibitory agent or a cytotoxic agent. The cytotoxic agent may be selected from the group consisting of toxins, antibiotics, radioactive isotopes and nucleolytic enzymes and toxins. Examples of toxins include, but are not limited to, maytansin, maytansinoids, saporin, gelonin, ricin or calicheamicin.

The mammalian cell may be a cancer cell. Preferably, the anti-Ovr110 monoclonal antibody inhibits the growth of Ovr110-expressing cancer cells in vivo.

The antibody may be produced in bacteria. Alternatively, the antibody may be a humanized form of an anti-Ovr110 antibody produced by a hybridoma selected from the group of hybridomas having ATCC accession number PTA-5180, PTA-5855, PTA-5856 and PTA-5884.

Preferably, the cancer is selected from the group consisting of ovarian, pancreatic, lung and breast cancer. The invention is also directed to a method of producing the antibodies comprising culturing an appropriate cell and recovering the antibody from the cell culture.

The invention is also directed to compositions comprising the antibodies and a carrier. The antibody may be conjugated to a cytotoxic agent. The cytotoxic agent may be a radioactive isotope or other chemotherapeutic agent.

The invention is also directed to a method of killing an Ovr110-expressing cancer cell, comprising contacting the cancer cell with the antibodies of this invention, thereby killing the cancer cell. The cancer cell may be selected from the group consisting of ovarian, pancreatic, lung and breast cancer cell.

The ovarian, or breast cancer may be ovarian serous adenocarcinoma or breast infiltrating ductal carcinoma or metastatic cancer. The breast cancer may be HER-2 negative breast cancer. The invention is also directed to a method of alleviating an Ovr110-expressing cancer in a mammal, comprising administering a therapeutically effective amount of the antibodies to the mammal.

In addition, the invention is directed to an article of manufacture comprising a container and a composition contained therein, wherein the composition comprises an antibody as described herein. The article of manufacture may also comprise an additional component, e.g., a package insert indicating that the composition can be used to treat ovarian, pancreatic, lung or breast cancer.

BRIEF DESCRIPTION OF TH FIGURES

FIGS. 1A an B show the results of FACS Analysis of Ovr110 Transfected Mouse LMTK Cells. FIG. 1A shows results for FACS Analysis with Donkey Anti-Mouse Ig-PE and FIG. 1B shows results for FACS Analysis with MAb A7.1 and Donkey Anti-Mouse Ig-PE.

FIGS. 2A, 2B and 2C show immunofluorescence with Ovr110-A57.1 in live ovarian and breast cancer cells. FIG. 2A shows immunofluorescence with Ovr110-A57.1 in live OVCAR-3 cells. FIG. 2B shows immunofluorescence with Ovr110-A57.1 in live SKBr-3 cells. FIG. 2C shows immunofluorescence with Ovr110-A57.1 in live CaOV-3 cells.

FIGS. 3A, 3B and 3C show Ovr110-A57.1 binding and internalization in live ovarian and breast cancer cells. FIG. 3A shows Ovr110-A57.1 binding and internalization in SKOV-3 cells. FIG. 3B shows Ovr110-A57.1 binding and internalization in SKBr-3 cells. FIG. 3C shows Ovr110-A57.1 binding and internalization in CaOV-3 cells.

FIGS. 4A, 4B and 4C show immunohistochemistry with Ovr110-A57.1 in ovarian serous adenocarcinoma. FIG. 4A and FIG. 4B show that the epithelial cells of the tumor displayed a strong membranous staining (arrows) with less intense cytoplasmic staining and no background staining in the stroma. FIG. 4C shows lack of specific labeling in a control experiment in which the primary antibody was replaced with a mouse IgG fraction.

FIGS. 5A, 5B and 5C show immunohistochemistry with Ovr110-A57.1 in breast infiltrating ductal Adenocarcinoma. FIGS. 5A and 5B show labeling was restricted to the cell surface of the epithelial cells of the tumors (arrows). FIG. 5C shows the absence of specific labeling in a control experiment in which the primary antibody was replaced with a mouse IgG fraction.

FIGS. 6A and 6B show immunohistochemistry with Ovr110-A57.1 in pancreas adenocarcinoma at low and high magnification.

FIG. 7: A-F show expression of B7 family members on day 3 in PHA stimulated T-CELLS CD3 FITC gated, and; G-I show binding of BTLA-Fc fusion protein to Ovr110-293F cells.

FIG. 8 A-C show Western blot detection of Ovr110 protein with mAb A57.1 in cell lines and human tumor tissues.

FIG. 10A shows knockdown with GAPDH Q-PCR primers and FIG. 10B shows knockdown with Ovr110 Q-PCR Primers.

FIG. 11 shows down-regulation of Ovr110 protein by siRNA in SKBR3 cells.

FIG. 12 shows that knockdown of Ovr110 mRNA induces apoptosis in SKBR3 cells.

FIG. 13A shows results from the caspase activity assay while FIG. 13B shows results from quantitative PCR.

FIGS. 15A and 15B show that overexpression of Ovr110 protects from apoptosis in RK3E cells (FIG. 15A) and IEC18 cells (FIG. 15B).

DETAILED DESCRIPTION OF THE INVENTION

Definitions and General Techniques

Figure 2:
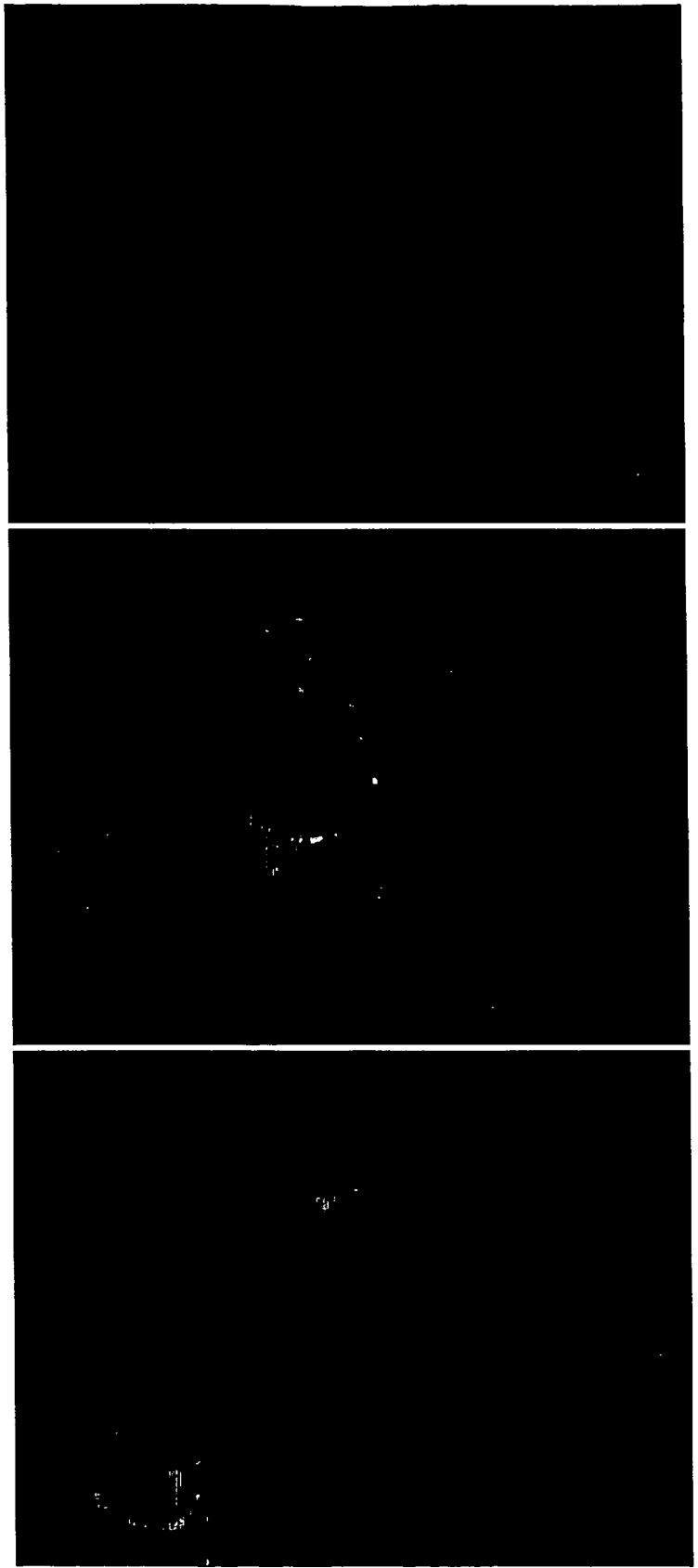

Human "Ovr110" as used herein, refers to a protein of 282 amino acids that is expressed on the cell surface as glycoprotein, whose nucleotide and amino acid sequence sequences are as disclosed in e.g., WO 00/12758, Cancer specific gene (CSG) Ovr110; WO 99/63088, Membrane-bound protein PRO1291; WO00/36107, Human ovarian carcinoma antigen; WO 02/02624-A2 Human B7-like protein (B7-L), the disclosures of which are hereby expressly incorporated by reference. The amino acids 30-282 are presumably on the cell surface. Ovr110 as used herein includes allelic variants and conservative substitution mutants of the protein, which have Ovr110 biological activity.

Recently, a series of three independent publications have identified Ovr110 in mouse and human as new member of the T-cell B7 family of co-stimulatory molecules, an important class of molecules that very tightly regulate the activation/inhibition of T-cell function. Prasad et al., B7S1, a novel B7 family member that negatively regulates T cell activation, Immunity 18:863-73 (2003); Sica et al., B7-H4, a molecule of the B7 family, negatively regulates T cell immunity, Immunity 18:849-61 (2003); and Zang et al., B7x: a widely expressed B7 family member that inhibits T cell activation, Proc. Natl. Acad. Sci. USA 100:10388-92 (2003). The predicted amino acid sequence of the mouse gene for B7S1 (Prasad 2003) was highly homologous to our previously identified Ovr110 molecule, and the predicted sequence of the human B7-H4/B7x (Sica 2003; Zang 2003) molecules were identical to Ovr110. Indirect immunofluorescent analysis by flow cytometry further confirmed the binding of our Ovr110 monoclonal antibodies to activated T-lymphocyte populations, as described by these authors.

Our findings that Ovr110 is apparently restricted to the more aggressive ovarian and breast cancers make this cell surface antigen an attractive target for immunotherapy of these and possibly other tumor types.

The term "antibody" (Ab) as used herein includes monoclonal antibodies, polyclonal antibodies, multispecific antibodies (e.g. bispecific antibodies), and antibody fragments, so long as they exhibit the desired biological activity. The term "immunoglobulin" (Ig) is used interchangeably with "antibody" herein.

An "isolated antibody" is one that has been identified and separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. Preferably, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or non-reducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The basic 4-chain antibody unit is a heterotetrameric glycoprotein composed of two identical light (L) chains and two identical heavy (H) chains (an IgM antibody consists of 5 of the basic heterotetramer unit along with an additional polypeptide called J chain, and therefore contain 10 antigen binding sites, while secreted IgA antibodies can polymerize to form polyvalent assemblages comprising 2-5 of the basic 4-chain units along with J chain). In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain (VH) followed by three constant domains (CH) for each of the α and γ chains and four CH domains for lambda and kappa isotypes. Each 6 L chain has at the N-terminus, a variable domain (VL) followed by a constant domain (CL) at its other end.

The VL is aligned with the VH and the CL is aligned with the first constant domain of the heavy chain (CHI).

Particular amino acid residues are believed to form an interface between the light chain and heavy chain variable domains. The pairing of a VH and VL together forms a single antigen-binding site. For the structure and properties of the different classes of antibodies, see, e.g., Basic and Clinical Immunology, 8th edition, Daniel P. Stites, Abba I. Teff and Tristram G. Parslow (eds.), Appleton & Lange, Norwalk, Conn., 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated α, δ, ε, γ and μ, respectively. The γ and α classes are further divided into subclasses on the basis of relatively minor differences in $C_H$ sequence and function, e.g., humans express the following subclasses: IgG1, IgG2, IgG3, IgG4, IgA1, and IgA2.

The term "variable" refers to the fact that certain segments of the variable domains differ extensively in sequence among antibodies. The V domain mediates antigen binding and defines specificity of a particular antibody for its particular antigen. However, the variability is not evenly distributed across the 1-10-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a P-sheet configuration, connected by three hypervariable regions, which form loops connecting, and in some cases forming part of, the P-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g. around about residues 24-34 (LI), 5056 (L2) and 89-97 (L3) in the VL, and around about 1-35 (HI), 50-65 (H2) and 95-102 (113) in the VH; Kabat et al., Sequences of Proteins of Immunological Interest, 5th Ed. Public Health Service, National Institutes of Health, Bethesda, Md. (1991)) and/or those residues from a "hypervariable loop" (e.g. residues 26-32 (LI), 50-52 (L2) and 91-96 (U) in the VL, and 26-32 (HI), 53-55 (1-12) and 96-101 (H3) in the VH; Chothia and Lesk J. Mol. Biol. 196: 901-917 (1987)).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations, which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816, 567). The "monoclonal antibodies" may also be isolated from phage antibody libraries using the techniques described in Clackson et al., Nature, 352:624-628 (1991) and Marks et al., J. Mol. Biol., 222:581-597 (1991), for example.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., Proc. Natl. Acad. Sci. USA, 81:6851-6855 (1984)). Chimeric antibodies of interest herein include "primatized" antibodies comprising variable domain antigen-binding sequences derived from a non-human primate (e.g. Old World Monkey, Ape etc), and human constant region sequences.

An "intact" antibody is one that comprises an antigen-binding site as well as a CL and at least heavy chain constant domains, CHI, CH2 and CH3. The constant domains may be native sequence constant domains (e.g. human native sequence constant domains) or amino acid sequence variant thereof. Preferably, the intact antibody has one or more effector functions.

An "antibody fragment" comprises a portion of an intact antibody, preferably the antigen binding or variable region of the intact antibody. Examples of antibody fragments include Fab, Fab', F(ab')2, and Fv fragments; diabodies; linear antibodies (see U.S. Pat. No. 5,641,870, Example 2; Zapata et al., Protein Eng. 8(10): 1057-1062 [1995]); single-chain antibody molecules; and multispecific antibodies formed from antibody fragments. Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain (VH), and the first constant domain of one heavy chain (CHI). Each Fab fragment is monovalent with respect to antigen binding, i.e., it has a single antigen-binding site. Pepsin treatment of an antibody yields a single large F(ab')2 fragment which roughly corresponds to two disulfide linked Fab fragments having divalent antigen-binding activity and is still capable of cross-linking antigen. Fab' fragments differ from Fab fragments by having additional few residues at the carboxy terminus of the CHI domain including one or more cysteines from the antibody hinge region. Fab'-SH is the designation herein for Fab' in which the cysteine residue(s) of the constant domains bear a free thiol group. F(ab')2 antibody fragments originally were produced as pairs of 8 Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the VH and VL domains which enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994); Borrebaeck 1995, infra.

The term "diabodies" refers to small antibody fragments prepared by constructing sFv fragments (see preceding paragraph) with short linkers (about 5-10 residues) between the VH and VL domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the VH and VL domains of the two antibodies are present on different polypeptide chains. Diabodies are described more fully in, for example, EP 404,097; WO 93/11161; and Hollinger et al., Proc. Natl. Acad. Sci. USA, 90:6444-6448 (1993).

A "native sequence" polypeptide is one which has the same amino acid sequence as a polypeptide (e.g., antibody) derived from nature. Such native sequence polypeptides can be isolated from nature or can be produced by recombinant or synthetic means. Thus, a native sequence polypeptide can have the amino acid sequence of a naturally occurring human polypeptide, murine polypeptide, or polypeptide from any other mammalian species.

The term "amino acid sequence variant" refers to a polypeptide that has amino acid sequences that differ to some extent from a native sequence polypeptide. Ordinarily, amino acid sequence variants of Ovr110 will possess at least about 70% homology with the native sequence Ovr110, preferably, at least about 80%, more preferably at least about 85%, even more preferably at least about 90% homology, and most preferably at least 95%. The amino acid sequence variants can possess substitutions, deletions, and/or insertions at certain positions within the amino acid sequence of the native amino acid sequence.

The phrase "functional fragment or analog" of an antibody is a compound having qualitative biological activity in common with a full-length antibody. For example, a functional fragment or analog of an anti-IgE antibody is one which can bind to an IgE immunoglobulin in such a manner so as to prevent or substantially reduce the ability of such molecule from having the ability to bind to the high affinity receptor, FcεRI.

"Homology" is defined as the percentage of residues in the amino acid sequence variant that are identical after aligning the sequences and introducing gaps, if necessary, to achieve the maximum percent homology. Methods and computer programs for the alignment are well known in the art. Sequence similarity may be measured by any common sequence analysis algorithm, such as GAP or BESTFIT or other variation Smith-Waterman alignment. See, T. F. Smith and M. S. Waterman, J. Mol. Biol. 147:195-197 (1981) and W. R. Pearson, Genomics 11:635-650 (1991).

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332: 323-329 (1988); and Presta, Curr. Op. Struct. Biol. 2:593-596 (1992).

As used herein, an anti-Ovr110 antibody that "internalizes" is one that is taken up by (i.e., enters) the cell upon binding to Ovr110 on a mammalian cell (i.e. cell surface Ovr110). The internalizing antibody will of course include antibody fragments, human or humanized antibody and antibody conjugate. For therapeutic applications, internalization in vivo is contemplated. The number of antibody molecules internalized will be sufficient or adequate to kill an Ovr110- expressing cell, especially an Ovr110-expressing cancer cell. Depending on the potency of the antibody or antibody conjugate, in some instances, the uptake of a single antibody molecule into the cell is sufficient to kill the target cell to which the antibody binds. For example, certain toxins are highly potent in killing such that internalization of one molecule of the toxin conjugated to the antibody is sufficient to kill the tumor cell.

Whether an anti-Ovr110 antibody internalizes upon binding Ovr110 on a mammalian cell can be determined by various assays including those described in the experimental examples below. For example, to test internalization in vivo, the test antibody is labeled and introduced into an animal known to have Ovr110 expressed on the surface of certain cells. The antibody can be radiolabeled or labeled with fluorescent or gold particles, for instance. Animals suitable for this assay include a mammal such as a NCR nude mouse that contains a human Ovr110-expressing tumor transplant or xenograft, or a mouse into which cells transfected with human Ovr110 have been introduced, or a transgenic mouse expressing the human Ovr110 transgene. Appropriate controls include animals that did not receive the test antibody or that received an unrelated antibody, and animals that received an antibody to another antigen on the cells of interest, which antibody is known to be internalized upon binding to the antigen. The antibody can be administered to the animal, e.g., by intravenous injection. At suitable time intervals, tissue sections of the animal can be prepared using known methods or as described in the experimental examples below, and analyzed by light microscopy or electron microscopy, for internalization as well as the location of the internalized antibody in the cell. For internalization in vitro, the cells can be incubated in tissue culture dishes in the presence or absence of the relevant antibodies added to the culture media and processed for microscopic analysis at desired time points. The presence of an internalized, labeled antibody in the cells can be directly visualized by microscopy or by autoradiography if radiolabeled antibody is used. Alternatively, in a quantitative biochemical assay, a population of cells comprising Ovr110-expressing cells are contacted in vitro or in vivo with a radiolabeled test antibody and the cells (if contacted in vivo, cells are then isolated after a suitable amount of time) are treated with a protease or subjected to an acid wash to remove uninternalized antibody on the cell surface. The cells are ground up and the amount of protease resistant, radioactive counts per minute (cpm) associated with each batch of cells is measured by passing the homogenate through a scintillation counter. Based on the known specific activity of the radiolabeled antibody, the number of antibody molecules internalized per cell can be deduced from the scintillation counts of the ground-up cells. Cells are "contacted" with antibody in vitro preferably in solution form such as by adding the cells to the cell culture media in the culture dish or flask and mixing the antibody well with the media to ensure uniform exposure of the cells to the antibody. Instead of adding to the culture media, the cells can be contacted with the test antibody in an isotonic solution such as PBS in a test tube for the desired time period. In vivo, the cells are contacted with antibody by any suitable method of administering the test antibody such as the methods of administration described below when administered to a patient.

The faster the rate of internalization of the antibody upon binding to the Ovr110-expressing cell in vivo, the faster the desired killing or growth inhibitory effect on the target Ovr110-expressing cell can be achieved, e.g., by a cytotoxic immunoconjugate. Preferably, the kinetics of internalization of the anti-Ovr110 antibodies are such that they favor rapid killing of the Ovr110-expressing target cell. Therefore, it is desirable that the anti-Ovr110 antibody exhibit a rapid rate of internalization preferably, within 24 hours from administration of the antibody in vivo, more preferably within about 12 hours, even more preferably within about 30 minutes to 1 hour, and most preferably, within about 30 minutes. The present invention provides antibodies that internalize as fast as about 15 minutes from the time of introducing the anti-Ovr110 antibody in vivo. The antibody will preferably be internalized into the cell within a few hours upon binding to Ovr110 on the cell surface, preferably within 1 hour, even more preferably within 15-30 minutes.

To determine if a test antibody can compete for binding to the same epitope as the epitope bound by the anti-Ovr110 antibodies of the present invention including the antibodies produced by the hybridomas deposited with the ATCC, a cross-blocking assay e.g., a competitive ELISA assay can be performed. In an exemplary competitive ELISA assay, Ovr110-coated wells of a microtiter plate, or Ovr110-coated sepharose beads, are pre-incubated with or without candidate competing antibody and then a biotin-labeled anti-Ovr110 antibody of the invention is added. The amount of labeled anti-Ovr110 antibody bound to the Ovr110 antigen in the wells or on the beads is measured using avidin-peroxidase conjugate and appropriate substrate.

Alternatively, the anti-Ovr110 antibody can be labeled, e.g., with a radioactive or fluorescent label or some other detectable and measurable label. The amount of labeled anti-Ovr110 antibody that binds to the antigen will have an inverse correlation to the ability of the candidate competing antibody (test antibody) to compete for binding to the same epitope on the antigen, i.e., the greater the affinity of the test antibody for the same epitope, the less labeled anti-Ovr-110 antibody will be bound to the antigen-coated wells. A candidate competing antibody is considered an antibody that binds substantially to the same epitope or that competes for binding to the same epitope as an anti-Ovr110 antibody of the invention if the candidate competing antibody can block binding of the anti-Ovr110 antibody by at least 20%, preferably by at least 20-50%, even more preferably, by at least 50% as compared to a control performed in parallel in the absence of the candidate competing antibody (but may be in the presence of a known noncompeting antibody). It will be understood that variations of this assay can be performed to arrive at the same quantitative value.

An antibody having a "biological characteristic" of a designated antibody, such as any of the monoclonal antibodies Ovr110.A7.1, Ovr110.A10.1, Ovr110.A13.1, Ovr110.A31.1, Ovr110.A57.1, Ovr110.A72.1 (previously identified as Ovr110 A22.1), Ovr110.A77.1, Ovr110.A87.1, Ovr110.A89, Ovr110.A 99.1, Ovr110.A102.1, Ovr110.A107, Ovr110.C1, Ovr110.C2, Ovr110.C3.2, Ovr110.C4, Ovr110.C5.1., Ovr110.C5.3, Ovr110.C6.3, Ovr110.C7.1, Ovr110.C8, Ovr110.C9.1, Ovr110.C10.1, Ovr110.C11.1, Ovr110.C12.1, Ovr110.C13, Ovr110.C14, Ovr110.C15, Ovr110.C16.1 and Ovr110.C17.1, is one which possesses one or more of the biological characteristics of that antibody which distinguish it from other antibodies that bind to the same antigen, Ovr110.A7.1, Ovr110.A10.1, Ovr110.A13.1, Ovr110.A31.1, Ovr110.A57.1, Ovr110.A72.1 (previously identified as Ovr110 A22.1), Ovr110.A77.1, Ovr110.A87.1, Ovr110.A89, Ovr110.A 99.1, Ovr110.A102.1, Ovr110.A107, Ovr110.C1, Ovr110.C2, Ovr110.C3.2, Ovr110.C4, Ovr110.C5.1., Ovr110.C5.3, Ovr110.C6.3, Ovr110.C7.1, Ovr110.C8, Ovr110.C9.1, Ovr110.C10.1, Ovr110.C11.1, Ovr110.C12.1, Ovr110.C13, Ovr110.C14, Ovr110.C15, Ovr110.C16.1 and Ovr110.C17.1 will bind the same epitope as that bound by Ovr110.A7.1, Ovr110.A10.1, Ovr110.A13.1, Ovr110.A31.1, Ovr110.A57.1, Ovr110.A72.1 (previously identified as Ovr110.A22.1), Ovr110.A77.1, Ovr110.A87.1, Ovr110.A89, Ovr110.A 99.1, Ovr110.A102.1, Ovr110.A107, Ovr110.C1, Ovr110.C2, Ovr110.C3.2, Ovr110.C4, Ovr110.C5.1., Ovr110.C5.3, Ovr110.C6.3, Ovr110.C7.1, Ovr110.C8, Ovr110.C9.1, Ovr110.C10.1, Ovr110.C11.1, Ovr110.C12.1, Ovr110.C13, Ovr110.C14, Ovr110.C15, Ovr110.C16.1 and Ovr110.C17.1 (e.g. which competes for binding or blocks binding of monoclonal antibody Ovr110.A7.1, Ovr110.A10.1, Ovr110.A13.1, Ovr110.A31.1, Ovr110.A57.1, Ovr110.A72.1 (previously identified as Ovr110.A22.1), Ovr110.A77.1, Ovr110.A87.1, Ovr110.A89, Ovr110.A 99.1, Ovr110.A102.1, Ovr110.A107, Ovr110.C1, Ovr110.C2, Ovr110.C3.2, Ovr110.C4, Ovr110.C5.1., Ovr110.C5.3, Ovr110.C6.3, Ovr110.C7.1, Ovr110.C8, Ovr110.C9.1, Ovr110.C10.1, Ovr110.C11.1, Ovr110.C12.1, Ovr110.C13, Ovr110.C14, Ovr110.C15, Ovr110.C16.1 and Ovr110.C17.1 to Ovr110), be able to target an Ovr110-expressing tumor cell in vivo and will internalize upon binding to Ovr110 on a mammalian cell in vivo. Likewise, an antibody with the biological characteristic of the Ovr110.A7.1, Ovr110.A10.1, Ovr110.A13.1, Ovr110.A31.1, Ovr110.A57.1, Ovr110.A72.1 (previously identified as Ovr110.A22.1), Ovr110.A77.1, Ovr110.A87.1, Ovr110.A89, Ovr110.A 99.1, Ovr110.A102.1, Ovr110.A107, Ovr110.C1, Ovr110.C2, Ovr110.C3.2, Ovr110.C4, Ovr110.C5.1., Ovr110.C5.3, Ovr110.C6.3, Ovr110.C7.1, Ovr110.C8, Ovr110.C9.1, Ovr110.C10.1, Ovr110.C11.1, Ovr110.C12.1, Ovr110.C13, Ovr110.C14, Ovr110.C15, Ovr110.C16.1 and Ovr110.C17.1 antibody will have the same epitope binding, targeting, internalizing, tumor growth inhibitory and cytotoxic properties of the antibody.

The term "antagonist" antibody is used in the broadest sense, and includes an antibody that partially or fully blocks, inhibits, or neutralizes a biological activity of a native Ovr110 protein disclosed herein. Methods for identifying antagonists of an Ovr110 polypeptide may comprise contacting an Ovr110 polypeptide or a cell expressing Ovr110 on the cell surface, with a candidate antagonist antibody and measuring a detectable change in one or more biological activities normally associated with the Ovr110 polypeptide.

An "antibody that inhibits the growth of tumor cells expressing Ovr110" or a "growth inhibitory" antibody is one which binds to and results in measurable growth inhibition of cancer cells expressing or overexpressing Ovr110. Preferred growth inhibitory anti-Ovr110 antibodies inhibit growth of Ovr110-expressing tumor cells e.g., ovarian, pancreatic, lung or breast cancer cells) by greater than 20%, preferably from about 20% to about 50%, and even more preferably, by greater than 50% (e.g. from about 50% to about 100%) as compared to the appropriate control, the control typically being tumor cells not treated with the antibody being tested. Growth inhibition can be measured at an antibody concentration of about 0.1 to 30 pg/ml or about 0.5 nM to 200 nM in cell culture, where the growth inhibition is determined 1-10 days after exposure of the tumor cells to the antibody. Growth inhibition of tumor cells in vivo can be determined in various ways such as is described in the Experimental Examples section below. The antibody is growth inhibitory in vivo if administration of the anti-Ovr110 antibody at about 1 pg/kg to about 100 mg/kg body weight results in reduction in tumor size or tumor cell proliferation within about 5 days to 3 months from the first administration of the antibody, preferably within about 5 to 30 days.

An antibody which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). The cell is usually one which overexpresses Ovr110. Preferably the cell is a tumor cell, e.g. an ovarian, pancreatic, lung or breast cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. Preferably, the antibody which induces apoptosis is one which results in about 2 to 50 fold, preferably about 5 to 50 fold, and most preferably about 10 to 50 fold, induction of annexin binding relative to untreated cells in an annexin binding assay.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g. B cell receptor); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g. Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. PNAS (USA) 95:652-656 (1998).

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRI1B contains an immunoreceptor tyrosine-based inhibition motif (ITIM) in its cytoplasmic domain. (see review M. in Daeron, Annu. Rev. Immunol. 15:203-234 (1997)). FcRs are reviewed in Ravetch and Kinet, Annu. Rev. Immunol 9:457-92 (1991); Capel et al., Immunomethods 4:25-34 (1994); and de Haas et al., J. Lab. Clin. Med. 126.330-41 (1995). Other FcRs, including those to be identified in the future, are encompassed by the term "FcR" herein. The term also includes the neonatal receptor, FcRn, which is responsible for the transfer, of maternal IgGs to the fetus (Guyer et al., J. Immunol. 117:587 (1976) and Kim et al., J. Immunol. 24:249 (1994)).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source, e.g. from blood.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g. as described in Gazzano-Santoro et al., J. Immunol. Methods 202:163 (1996) may be performed.

The terms "cancer" and "cancerous" refer to or describe the physiological condition in mammals that is typically characterized by unregulated cell growth. Examples of cancer include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, multiple myeloma and B-cell lymphoma, brain, as well as head and neck cancer, and associated metastases.

A "Ovr110-expressing cell" is a cell which expresses endogenous or transfected Ovr110 on the cell surface. A "Ovr110-expressing cancer" is a cancer comprising cells that have Ovr110 protein present on the cell surface. A "Ovr110-expressing cancer" produces sufficient levels of Ovr110 on the surface of cells thereof, such that an anti-Ovr110 antibody can bind thereto and have a therapeutic effect with respect to the cancer. A cancer which "overexpresses" Ovr110 is one which has significantly higher levels of Ovr110 at the cell surface thereof, compared to a noncancerous cell of the same tissue type. Such overexpression may be caused by gene amplification or by increased transcription or translation. Ovr110 overexpression may be determined in a diagnostic or prognostic assay by evaluating increased levels of the Ovr110 protein present on the surface of a cell (e.g. via an immunohistochemistry assay; FACS analysis). Alternatively, or additionally, one may measure levels of Ovr110-encoding nucleic acid or mRNA in the cell, e.g. via fluorescent in situ hybridization; (FISH; see WO98/45479 published October, 1998), Southern blotting, Northern blotting, or polymerase chain reaction (PCR) techniques, such as real time quantitative PCR (RT-PCR). One may also study Ovr110 overexpression by measuring shed antigen in a biological fluid such as serum, e.g., using antibody-based assays (see also, e.g., U.S. Pat. No. 4,933,294 issued Jun. 12, 1990; WO91/05264 published Apr. 18, 1991; U.S. Pat. No. 5,401,638 issued Mar. 28, 1995; and Sias et al. J. Immunol. Methods 132: 73-80 (1990)). Aside from the above assays, various in vivo assays are available to the skilled practitioner. For example, one may expose cells within the body of the patient to an antibody which is optionally labeled with a detectable label, e.g. a radioactive isotope, and binding of the antibody to cells in the patient can be evaluated, e.g. by external scanning for radioactivity or by analyzing a biopsy taken from a patient previously exposed to the antibody. An Ovr110-expressing cancer includes ovarian, pancreatic, lung or breast cancer.

A "mammal" for purposes of treating a cancer or alleviating the symptoms of cancer, refers to any mammal, including-humans, domestic and farm animals, and zoo, sports, or pet animals, such as dogs, cats, cattle, horses, sheep, pigs, goats, rabbits, etc. Preferably, the mammal is human.

"Treating" or "treatment" or "alleviation" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented. A subject or mammal is successfully "treated" for an Ovr110-expressing cancer if, after receiving a therapeutic amount of an anti-Ovr110 antibody according to the methods of the present invention, the patient shows observable and/or measurable reduction in or absence of one or more of the following: reduction in the number of cancer cells or absence of the cancer cells; reduction in the tumor size; inhibition (i.e., slow to some extent and preferably stop) of cancer cell infiltration into peripheral organs including the spread of cancer into soft tissue and bone; inhibition (i.e., slow to some extent and preferably stop) of tumor metastasis; inhibition, to some extent, of tumor growth; and/or relief to some extent, one or more of the symptoms associated with the specific cancer; reduced morbidity and mortality, and improvement in quality of life issues. To the extent the anti-Ovr110 antibody may prevent growth and/or kill existing cancer cells, it may be cytostatic and/or cytotoxic. Reduction of these signs or symptoms may also be felt by the patient.

The above parameters for assessing successful treatment and improvement in the disease are readily measurable by routine procedures familiar to a physician. For cancer therapy, efficacy can be measured, for example, by assessing the time to disease progression (TTP) and/or determining the response rate (RR).

The term "therapeutically effective amount" refers to an amount of an antibody or a drug effective to "treat" a disease or disorder in a subject or mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. See preceding definition of "treating". To the extent the drug may prevent growth and/or kill existing cancer cells, it may be cytostatic and/or cytotoxic.

"Chronic" administration refers to administration of the agent(s) in a continuous mode as opposed to an acute mode, so as to maintain the initial therapeutic effect (activity) for an extended period of time.

"Intermittent" administration is treatment that is not consecutively done without interruption, but rather is cyclic in nature.

Administration "in combination with" one or more further therapeutic agents includes simultaneous (concurrent) and consecutive administration in any order.

"Carriers" as used herein include pharmaceutically acceptable carriers, excipients, or stabilizers which are nontoxic to the cell or mammal being exposed thereto at the dosages and concentrations employed.

Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$, and radioactive isotopes of Lu), chemotherapeutic agents e.g. methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial fungal, plant or animal origin, including fragments and/or variants thereof, e.g., gelonin, ricin, saporin, and the various antitumor or anticancer agents disclosed below. Other cytotoxic agents are described below. A tumoricidal agent causes destruction of tumor cells.

A "growth inhibitory agent" when used herein refers to a compound or composition which inhibits growth of a cell, especially an Ovr110-expressing cancer cell, either in vitro or in vivo. Thus, the growth inhibitory agent may be one which significantly reduces the percentage of Ovr110-expressing cells in S phase. Examples of growth inhibitory agents include agents that block cell cycle progression (at a place other than S phase), such as agents that induce GI arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest GI also spill over into S-phase arrest, for example, DNA alkylating agents such as tamoxifen, prednisone, dacarbazine, mechlorethamine, cisplatin, methotrexate, 5-fluorouracil, and ara-C. Further information can be found in The Molecular Basis of Cancer, Mendelsohn and Israel, eds., Chapter 1, entitled "Cell cycle regulation, oncogenes, and antineoplastic drugs" by Murakami et al. (W B Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

"Label" as used herein refers to a detectable compound or composition which is conjugated directly or indirectly to the antibody so as to generate a "labeled" antibody. The label may be detectable by itself (e.g. radioisotope labels or fluorescent labels) or, in the case of an enzymatic label, may catalyze chemical alteration of a substrate compound or composition which is detectable.

The term "epitope tagged" used herein refers to a chimeric polypeptide comprising an anti-Ovr110 antibody polypeptide fused to a "tag polypeptide". The tag polypeptide has enough residues to provide an epitope against which an antibody can be made, yet is short enough such that it does not interfere with activity of the Ig polypeptide to which it is fused. The tag polypeptide is also preferably fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

A "small molecule" is defined herein to have a molecular weight below about 500 Daltons.

The term "package insert" is used to refer to instructions customarily included in commercial packages of therapeutic products, that contain information about the indications, usage, dosage, administration, contraindications and/or warnings concerning the use of such therapeutic products.

An "isolated nucleic acid molecule" is a nucleic acid molecule, e.g., an RNA, DNA, or a mixed polymer, which is substantially separated from other genome DNA sequences as well as proteins or complexes such as ribosomes and polymerases, which naturally accompany a native sequence. The term embraces a nucleic acid molecule which has been removed from its naturally occurring environment, and includes recombinant or cloned DNA isolates and chemically synthesized analogues or analogues biologically synthesized by heterologous systems. A substantially pure nucleic acid molecule includes isolated forms of the nucleic acid molecule.

"Vector" includes shuttle and expression vectors and includes, e.g., a plasmid, cosmid, or phagemid. Typically, a plasmid construct will also include an origin of replication (e.g., the ColE1 origin of replication) and a selectable marker (e.g., ampicillin or tetracycline resistance), for replication and selection, respectively, of the plasmids in bacteria. An "expression vector" refers to a vector that contains the necessary control sequences or regulatory elements for expression of the antibodies including antibody fragment of the invention, in prokaryotic, e.g., bacterial, or eukaryotic cells. Suitable vectors are disclosed below.

The cell that produces an anti-Ovr110 antibody of the invention will include the parent hybridoma cell e.g., the hybridomas that are deposited with the ATCC, as well as bacterial and eukaryotic host cells into which nucleic acid encoding the antibodies have been introduced. Suitable host cells are disclosed below.

RNA interference refers to the process of sequence-specific post transcriptional gene silencing in animals mediated by short interfering RNAs (siRNA) (Fire et al., 1998, Nature, 391, 806). The corresponding process in plants is commonly referred to as post transcriptional gene silencing or RNA silencing and is also referred to as quelling in fungi. The process of post transcriptional gene silencing is thought to be an evolutionarily conserved cellular defense mechanism used to prevent the expression of foreign genes which is commonly shared by diverse flora and phyla (Fire et al., 1999, Trends Genet., 15, 358). Such protection from foreign gene expression may have evolved in response to the production of double stranded RNAs (dsRNA) derived from viral infection or the random integration of transposon elements into a host genome via a cellular response that specifically destroys homologous single stranded RNA or viral genomic RNA. The presence of dsRNA in cells triggers the RNAi response though a mechanism that has yet to be fully characterized. This mechanism appears to be different from the interferon response that results from dsRNA mediated activation of protein kinase PKR and 2',5'-oligoadenylate synthetase resulting in non-specific cleavage of mRNA by ribonuclease L.

The presence of long dsRNAs in cells stimulates the activity of a ribonuclease III enzyme referred to as dicer. Dicer is involved in the processing of the dsRNA into short pieces of dsRNA known as short interfering RNAs (siRNA) (Berstein et al., 2001, Nature, 409, 363). Short interfering RNAs derived from dicer activity are typically about 21-23 nucleotides in length and comprise about 19 base pair duplexes. Dicer has also been implicated in the excision of 21 and 22 nucleotide small temporal RNAs (stRNA) from precursor RNA of conserved structure that are implicated in translational control (Hutvagner et al., 2001, Science, 293, 834). The RNAi response also features an endonuclease complex containing a siRNA, commonly referred to as an RNA-induced silencing complex (RISC), which mediates cleavage of single stranded RNA having sequence complementary to the antisense strand of the siRNA duplex. Cleavage of the target RNA takes place in the middle of the region complementary to the antisense strand of the siRNA duplex (Elbashir et al., 2001, Genes Dev., 15, 188).

Short interfering RNA mediated RNAi has been studied in a variety of systems. Fire et al., 1998, Nature, 391, 806, were the first to observe RNAi in *C. Elegans*. Wianny and Goetz, 1999, Nature Cell Biol., 2, 70, describe RNAi mediated by dsRNA in mouse embryos. Hammond et al., 2000, Nature, 404, 293, describe RNAi in *Drosophila* cells transfected with dsRNA. Elbashir et al., 2001, Nature, 411, 494, describe RNAi induced by introduction of duplexes of synthetic 21-nucleotide RNAs in cultured mammalian cells including human embryonic kidney and HeLa cells. Recent work in *Drosophila* embryonic lysates (Elbashir et al., 2001, EMBO J., 20, 6877) has revealed certain requirements for siRNA length, structure, chemical composition, and sequence that are essential to mediate efficient RNAi activity. These studies have shown that 21 nucleotide siRNA duplexes are most active when containing two nucleotide 3'-overhangs. Furthermore, complete substitution of one or both siRNA strands with 2'-deoxy (2'-H) or 2'-O-methyl nucleotides abolishes RNAi activity, whereas substitution of the 3'-terminal siRNA overhang nucleotides with deoxy nucleotides (2'-H) was shown to be tolerated. Single mismatch sequences in the center of the siRNA duplex were also shown to abolish RNAi activity. In addition, these studies also indicate that the position of the cleavage site in the target RNA is defined by the 5'-end of the siRNA guide sequence rather than the 3'-end (Elbashir et al., 2001, EMBO J., 20, 6877). Other studies have indicated that a 5'-phosphate on the target-complementary strand of a siRNA duplex is required for siRNA activity and that ATP is utilized to maintain the 5'-phosphate moiety on the siRNA (Nykanen et al., 2001, Cell, 107, 309).

Studies have shown that replacing the 3'-overhanging segments of a 21-mer siRNA duplex having 2 nucleotide 3' overhangs with deoxyribonucleotides does not have an adverse effect on RNAi activity. Replacing up to 4 nucleotides on each end of the siRNA with deoxyribonucleotides has been reported to be well tolerated whereas complete substitution with deoxyribonucleotides results in no RNAi activity (Elbashir et al., 2001, EMBO J., 20, 6877). In addition, Elbashir et al., supra, also report that substitution of siRNA with 2'-O-methyl nucleotides completely abolishes RNAi activity. Li et al., International PCT Publication No. WO 00/44914, and Beach et al., International PCT Publication No. WO 01/68836 both suggest that siRNA "may include modifications to either the phosphate-sugar back bone or the nucleoside to include at least one of a nitrogen or sulfur heteroatom", however neither application teaches to what extent these modifications are tolerated in siRNA molecules nor provide any examples of such modified siRNA. Kreutzer and Limmer, Canadian Patent Application No. 2,359,180, also describe certain chemical modifications for use in dsRNA constructs in order to counteract activation of double stranded-RNA-dependent protein kinase PKR, specifically 2'-amino or 2'-O-methyl nucleotides, and nucleotides containing a 2'-O or 4'-C methylene bridge. However, Kreutzer and Limmer similarly fail to show to what extent these modifications are tolerated in siRNA molecules nor do they provide any examples of such modified siRNA.

Parrish et al., 2000, Molecular Cell, 6, 1977-1087, tested certain chemical modifications targeting the unc-22 gene in *C. elegans* using long (>25 nt) siRNA transcripts. The authors describe the introduction of thiophosphate residues into these siRNA transcripts by incorporating thiophosphate nucleotide analogs with T7 and T3 RNA polymerase and observed that "RNAs with two (phosphorothioate) modified bases also had substantial decreases in effectiveness as RNAi triggers (data not shown); (phosphorothioate) modification of more than two residues greatly destabilized the RNAs in vitro and we were not able to assay interference activities." Id. at 1081. The authors also tested certain modifications at the 2'-position of the nucleotide sugar in the long siRNA transcripts and observed that substituting deoxynucleotides for ribonucleotides "produced a substantial decrease in interference activity", especially in the case of Uridine to Thymidine and/or Cytidine to deoxy-Cytidine substitutions. Id. In addition, the authors tested certain base modifications, including substituting 4-thiouracil, 5-bromouracil, 5-iodouracil, 3-(aminoallyl) uracil for uracil, and inosine for guanosine in sense and antisense strands of the siRNA, and found that whereas 4-thiouracil and 5-bromouracil were all well tolerated, inosine "produced a substantial decrease in interference activity" when incorporated in either strand. Incorporation of 5-iodouracil and 3-(aminoallyl)uracil in the antisense strand resulted in substantial decrease in RNAi activity as well.

Beach et al., International PCT Publication No. WO 01/68836, describes specific methods for attenuating gene expression using endogenously derived dsRNA. Tuschl et al., International PCT Publication No. WO 01/75164, describes a *Drosophila* in vitro RNAi system and the use of specific siRNA molecules for certain functional genomic and certain therapeutic applications; although Tuschl, 2001, Chem. Biochem., 2, 239-245, doubts that RNAi can be used to cure genetic diseases or viral infection due "to the danger of activating interferon response". Li et al., International PCT Publication No. WO 00/44914, describes the use of specific dsRNAs for use in attenuating the expression of certain target genes. Zernicka-Goetz et al., International PCT Publication No. WO 01/36646, describes certain methods for inhibiting the expression of particular genes in mammalian cells using certain dsRNA molecules. Fire et al., International PCT Publication No. WO 99/32619, describes particular methods for introducing certain dsRNA molecules into cells for use in inhibiting gene expression. Plaetinck et al., International PCT Publication No. WO 00/01846, describes certain methods for identifying specific genes responsible for conferring a particular phenotype in a cell using specific dsRNA molecules. Mello et al., International PCT Publication No. WO 01/29058, describes the identification of specific genes involved in dsRNA mediated RNAi. Deschamps Depaillette et al., International PCT Publication No. WO 99/07409, describes specific compositions consisting of particular dsRNA molecules combined with certain anti-viral agents. Driscoll et al., International PCT Publication No. WO 01/49844, describes specific DNA constructs for use in facilitating gene silencing in targeted organisms. Parrish et al., 2000, Molecular Cell, 6, 1977-1087, describes specific chemically modified siRNA constructs targeting the unc-22 gene of C. elegans. Tuschl et al., International PCT Publication No. WO 02/44321, describe certain synthetic siRNA constructs.

Compositions and Methods of the Invention

The invention provides anti-Ovr110 antibodies. Preferably, the anti-Ovr110 antibodies internalize upon binding to cell surface Ovr110 on a mammalian cell. The anti-Ovr110 antibodies may also destroy or lead to the destruction of tumor cells bearing Ovr110.

It was not apparent that Ovr110 was internalization-competent. In addition the ability of an antibody to internalize depends on several factors including the affinity, avidity, and isotype of the antibody, and the epitope that it binds. We have demonstrated herein that the cell surface Ovr110 is internalization competent upon binding by the anti-Ovr110 antibodies of the invention. Additionally, it was demonstrated that the anti-Ovr110 antibodies of the present invention can specifically target Ovr110-expressing tumor cells in vivo and inhibit or kill these cells. These in vivo tumor targeting, internalization and growth inhibitory properties of the anti-Ovr110 antibodies make these antibodies very suitable for therapeutic uses, e.g., in the treatment of various cancers including ovarian, pancreatic, lung or breast cancer. Internalization of the anti-Ovr110 antibody is preferred, e.g., if the antibody or antibody conjugate has an intracellular site of action and if the cytotoxic agent conjugated to the antibody does not readily cross the plasma membrane (e.g., the toxin calicheamicin). Internalization is not necessary if the antibodies or the agent conjugated to the antibodies do not have intracellular sites of action, e.g., if the antibody can kill the tumor cell by ADCC or some other mechanism.

The anti-Ovr110 antibodies of the invention also have various non-therapeutic applications. The anti-Ovr110 antibodies of the present invention can be useful for diagnosis and staging of Ovr110-expressing cancers (e.g., in radioimaging). They may be used alone or in combination with other ovarian cancer markers, including, but not limited to, CA125, HE4 and mesothelin. The antibodies are also useful for purification or immunoprecipitation of Ovr110 from cells, for detection and quantitation of Ovr110 in vitro, e.g. in an ELISA or a Western blot, to kill and eliminate Ovr110-expressing cells from a population of mixed cells as a step in the purification of other cells. The internalizing anti-Ovr110 antibodies of the invention can be in the different forms encompassed by the definition of "antibody" herein. Thus, the antibodies include full length or intact antibody, antibody fragments, native sequence antibody or amino acid variants, humanized, chimeric or fusion antibodies, immunoconjugates, and functional fragments thereof. In fusion antibodies, an antibody sequence is fused to a heterologous polypeptide sequence. The antibodies can be modified in the Fc region to provide desired effector functions. As discussed in more detail in the sections below, with the appropriate Fc regions, the naked antibody bound on the cell surface can induce cytotoxicity, e.g., via antibody-dependent cellular cytotoxicity (ADCC) or by recruiting complement in complement dependent cytotoxicity, or some other mechanism. Alternatively, where it is desirable to eliminate or reduce effector function, so as to minimize side effects or therapeutic complications, certain other Fc regions may be used.

The antibody may compete for binding, or binds substantially to, the same epitope bound by the antibodies of the invention. Antibodies having the biological characteristics of the present anti-Ovr110 antibodies of the invention are also contemplated, e.g., an anti-Ovr110 antibody which has the biological characteristics of a monoclonal antibody produced by the hybridomas accorded ATCC accession numbers PTA-5180, PTA-5855, PTA-5856 and PTA-5884, specifically including the in vivo tumor targeting, internalization and any cell proliferation inhibition or cytotoxic characteristics. Specifically provided are anti-Ovr110 antibodies that bind to an epitope present in amino acids 30-40, 40-50, 50-60, 60-70, 70-80, 80-90, 90-100, 100-110, 110-120, 120-130, 130-140, 140-150, 150-160, 160-170, 170-180, 180-190, 190-200, 200-210, 210-220, 220-230, 230-240, 240-250, 250-260, 260-270, 270-282 of human Ovr110.

Methods of producing the above antibodies are described in detail below.

The present anti-Ovr110 antibodies are useful for treating an Ovr110-expressing cancer or alleviating one or more symptoms of the cancer in a mammal. Such a cancer includes ovarian, pancreatic, lung or breast cancer, cancer of the urinary tract, lung cancer, breast cancer, colon cancer, pancreatic cancer, and ovarian cancer, more specifically, prostate adenocarcinoma, renal cell carcinomas, colorectal adenocarcinomas, lung adenocarcinomas, lung squamous cell carcinomas, and pleural mesothelioma. The cancers encompass metastatic cancers of any of the preceding, e.g., ovarian, pancreatic, lung or breast cancer metastases. The antibody is able to bind to at least a portion of the cancer cells that express Ovr110 in the mammal and preferably is one that does not induce or that minimizes HAMA response. Preferably, the antibody is effective to destroy or kill Ovr110-expressing tumor cells or inhibit the growth of such tumor cells, in vitro or in vivo, upon binding to Ovr110 on the cell. Such an antibody includes a naked anti-Ovr110 antibody (not conjugated to any agent). Naked anti-Ovr110 antibodies having tumor growth inhibition properties in vivo include the antibodies described in the Experimental Examples below. Naked antibodies that have cytotoxic or cell growth inhibition properties can be further conjugated with a cytotoxic agent to render them even more potent in tumor cell destruction. Cytotoxic properties can be conferred to an anti-Ovr110 antibody by, e.g., conjugating the antibody with a cytotoxic agent, to form an immunoconjugate as described below. The cytotoxic agent or a growth inhibitory agent is preferably a small molecule. Toxins such as maytansin, maytansinoids, saporin, gelonin, ricin or calicheamicin and analogs or derivatives thereof, are preferable.

The invention provides a composition comprising an anti-Ovr110 antibody of the invention, and a carrier. For the purposes of treating cancer, compositions can be administered to the patient in need of such treatment, wherein the composition can comprise one or more anti-Ovr110 antibodies present as an immunoconjugate or as the naked antibody. Further, the compositions can comprise these antibodies in combination with other therapeutic agents such as cytotoxic or growth inhibitory agents, including chemotherapeutic agents. The invention also provides formulations comprising an anti-Ovr110 antibody of the invention, and a carrier. The formulation may be a therapeutic formulation comprising a pharmaceutically acceptable carrier.

Another aspect of the invention is isolated nucleic acids encoding the internalizing anti-Ovr110 antibodies. Nucleic acids encoding both the H and L chains and especially the hypervariable region residues, chains which encode the native sequence antibody as well as variants, modifications and humanized versions of the antibody, are encompassed.

The invention also provides methods useful for treating an Ovr110-expressing cancer or alleviating one or more symptoms of the cancer in a mammal, comprising administering a therapeutically effective amount of an internalizing anti-Ovr110 antibody to the mammal. The antibody therapeutic compositions can be administered short term (acute) or chronic, or intermittent as directed by physician. Also provided are methods of inhibiting the growth of, and killing an Ovr110 expressing cell. Finally, the invention also provides kits and articles of manufacture comprising at least one antibody of this invention, preferably at least one internalizing anti-Ovr110 antibody of this invention. Kits containing anti-Ovr110 antibodies find use in detecting Ovr-110 expression, or in therapeutic or diagnostic assays, e.g., for Ovr110 cell killing assays or for purification and/or immunoprecipitation of Ovr110 from cells. For example, for isolation and purification of Ovr110, the kit can contain an anti-Ovr110 antibody coupled to a solid support, e.g., a tissue culture plate or beads (e.g., sepharose beads). Kits can be provided which contain antibodies for detection and quantitation of Ovr110 in vitro, e.g. in an ELISA or a Western blot. Such antibody useful for detection may be provided with a label such as a fluorescent or radiolabel.

Production of Anti-Ovr110 Antibodies

The following describes exemplary techniques for the production of the antibodies useful in the present invention. Some of these techniques are described further in Example 1. The Ovr110 antigen to be used for production of antibodies may be, e.g., the full length polypeptide or a portion thereof including a soluble form of Ovr110 lacking the membrane spanning sequence, or synthetic peptides to selected portions of the protein.

Alternatively, cells expressing Ovr110 at their cell surface (e.g. CHO or NIH-3T3 cells transformed to overexpress Ovr110; ovarian, pancreatic, lung, breast or other Ovr110-expressing tumor cell line), or membranes prepared from such cells can be used to generate antibodies. The nucleotide and amino acid sequences of human and murine Ovr110 are available as provided above. Ovr110 can be produced recombinantly in and isolated from, prokaryotic cells, e.g., bacterial cells, or eukaryotic cells using standard recombinant DNA methodology. Ovr110 can be expressed as a tagged (e.g., epitope tag) or other fusion protein to facilitate its isolation as well as its identification in various assays.

Antibodies or binding proteins that bind to various tags and fusion sequences are available as elaborated below. Other forms of Ovr110 useful for generating antibodies will be apparent to those skilled in the art.

Tags

Various tag polypeptides and their respective antibodies are well known in the art. Examples include poly-histidine (poly-his) or poly-histidine-glycine (poly-his-gly) tags; the flu HA tag polypeptide and its antibody 12CA5 (Field et al., Mol. Cell. Biol., 8:2159-2165 (1988)); the c-myc tag and the 8F9, 3C7, 6E10, G4, B7 and 9E10 antibodies thereto (Evan et al., Molecular and Cellular Biology, 5:3610-3616 (1985)); and the Herpes Simplex virus glycoprotein D (gD) tag and its antibody (Paborsky et al., Protein Engineering, 3(6):547-553 (1990)). The FLAG-peptide (Hopp et al., BioTechnology, 6:1204-1210 (1988)) is recognized by an anti-FLAG M2 monoclonal antibody (Eastman Kodak Co., New Haven, Conn.). Purification of a protein containing the FLAG peptide can be performed by immunoaffinity chromatography using an affinity matrix comprising the anti-FLAG M2 monoclonal antibody covalently attached to agarose (Eastman Kodak Co., New Haven, Conn.). Other tag polypeptides include the KT3 epitope peptide [Martin et al., Science, 255:192-194 (1992)]; an α-tubulin epitope peptide (Skinner et al., J. Biol. Chenz., 266:15163-15166 (1991)); and the T7 gene protein peptide tag (Lutz-Freyermuth et al., Proc. Natl. Acad. Sci. USA, 87:6393-6397 (1990)).

Polyclonal Antibodies

Polyclonal antibodies are preferably raised in animals, preferably non-human animals, by multiple subcutaneous (sc) or intraperitoneal (ip) injections of the relevant antigen and an adjuvant. It may be useful to conjugate the relevant antigen (especially when synthetic peptides are used) to a protein that is immunogenic in the species to be immunized. For example, the antigen can be conjugated to keyhole limpet hemocyanin (KLH), serum, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, $SOCl_2$, or $R^1$ N=C=NR, where R and $R^1$ are different alkyl groups. Conjugates also can be made in recombinant cell culture as protein fusions.

Animals are immunized against the antigen, immunogenic conjugates, or derivatives by combining, e.g., 5-100 pg of the protein or conjugate (for rabbits or mice, respectively) with 3 volumes of Freund's complete adjuvant and injecting the solution intradermally at multiple sites. One month later, the animals are boosted with ⅕ to 1⁄10 the original amount of peptide or conjugate in Freund's complete adjuvant by subcutaneous injection at multiple sites. Seven to 14 days later, the animals are bled and the serum is assayed for antibody titer. Animals are boosted until the titer plateaus. Also, aggregating agents such as alum are suitably used to enhance the immune response.

Monoclonal Antibodies

Monoclonal antibodies may be made using the hybridoma method first described by Kohler et al., Nature, 256:495 (1975), or may be made by recombinant DNA methods (U.S. Pat. No. 4,816,567). In the hybridoma method, a mouse or other appropriate host animal, such as a hamster, is immunized as described above to elicit lymphocytes that produce or are capable of producing antibodies that will specifically bind to the protein used for immunization. Alternatively, lymphocytes may be immunized in vitro. After immunization, lymphocytes are isolated and then fused with a "fusion partner", e.g., a myeloma cell line using a suitable fusing agent, such as polyethylene glycol, to form a hybridoma cell (Goding, Monoclonal Antibodies. Principles and Practice, pp 103 (Academic Press, 1986)).

The hybridoma cells thus prepared are seeded and grown in a suitable culture medium which medium preferably contains one or more substances that inhibit the growth or survival of the unfused, fusion partner, e.g, the parental myeloma cells. For example, if the parental myeloma cells lack the enzyme hypoxanthine guanine phosphoribosyl transferase (HGPRT or HPRT), the selective culture medium for the hybridomas typically will include hypoxanthine, aminopterin, and thymidine (HAT medium), which substances prevent the growth of HGPRT-deficient cells.

Preferred fusion partner myeloma cells are those that fuse efficiently, support stable high-level production of antibody by the selected antibody-producing cells, and are sensitive to a selective medium that selects against the unfused parental cells. Preferred myeloma cell lines are murine myeloma lines, such as those derived from MOPC-21 and MPC-11 mouse tumors available from the Salk Institute Cell Distribution Center, San Diego, Calif. USA, and SP-2 and derivatives e.g., X63-Ag8-653 cells available from the American Type Culture Collection, Rockville, Md. USA. Human myeloma and mouse-human heteromyeloma cell lines also have been described for the production of human monoclonal antibodies (Kozbor, J. Immunol., 133:3001 (1984); and Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The binding affinity of the monoclonal antibody can, for example, be determined by the Scatchard analysis described in Munson et al., Anal. Biochem., 107:220 (1980). Once hybridoma cells that produce antibodies of the desired specificity, affinity, and/or activity are identified, the clones may be subcloned by limiting dilution procedures and grown by standard methods (Goding, Monoclonal Antibodies: Principles and Practice, pp 103 (Academic Press, 1986)). Suitable culture media for this purpose include, for example, D-MEM or RPMI-1640 medium. In addition, the hybridoma cells may be grown in vivo as ascites tumors in an animal e.g, by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-Sepharose) or ion-exchange chromatography, hydroxylapatite chromatography, gel electrophoresis, dialysis, etc.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transformed or transfected into prokaryotic or eukaryotic host cells such as, e.g., E coli cells, simian COS cells, Chinese Hamster Ovary (CHO) cells, or myeloma cells, that do not otherwise produce antibody protein, to obtain the synthesis of monoclonal antibodies in the recombinant host cells. Review articles on recombinant expression in bacteria of DNA encoding the antibody include Skerra et al., Curr. Opinion in Immunol., 5:256-262 (1993) and Phickthun, Immunol. Revs., 130:151-188 (1992).

Further, the monoclonal antibodies or antibody fragments can be isolated from antibody phage libraries generated using the techniques described in McCafferty et al., Nature, 348: 552-554 (1990). Clackson et al., Nature, 352:624-628 (1991) and Marks et al., J. Mol. Biol., 222:581-597 (1991) describe the isolation of murine and human antibodies, respectively, using phage libraries. Subsequent publications describe the production of high affinity (nM range) human antibodies by chain shuffling (Marks et al., Bio/Technology, 10:779-783 (1992)), as well as combinatorial infection and in vivo recombination as a strategy for constructing very large phage libraries (Waterhouse et al., Nuc. Acids. Res., 21:2265-2266 (1993)). Thus, these techniques are viable alternatives to traditional monoclonal antibody hybridoma techniques for isolation of monoclonal antibodies.

The DNA that encodes the antibody may be modified to produce chimeric or fusion antibody polypeptides, for example, by substituting human heavy chain and light chain constant domain (CH and CL) sequences for the homologous murine sequences (U.S. Pat. No. 4,816,567; and Morrison, et al., Proc. Natl. Acad. Sci. USA, 81:6851 (1984)), or by fusing the immunoglobulin coding sequence with all or part of the coding sequence for a non-immunoglobulin polypeptide (heterologous polypeptide). The nonimmunoglobulin polypeptide sequences can substitute for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

Humanized Antibodies

Methods for humanizing non-human antibodies have been described in the art. Preferably, a humanized antibody has one or more amino acid residues introduced into it from a source which is nonhuman. These non-human amino acid residues are often referred to as "import" residues, which are typically taken from an "import" variable domain. Humanization can be essentially performed following the method of Winter and co-workers (Jones et al., Nature, 321:522-525 (1986); Reichmann et al., Nature, 332:323-327 (1988); Verhoeyen et al., Science, 239:1534-1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity and HAMA response (human anti-mouse antibody) when the antibody is intended for human therapeutic use. According to the so-called "best-fit" method, the sequence of the variable domain of a rodent antibody is screened against the entire library of known human variable domain sequences. The human V domain sequence which is closest to that of the rodent is identified and the human framework region (FR) within it accepted for the humanized antibody (Sims et al., J. Immunol., 151:2296 (1993); Chothia et al., J. Mol. Biol., 196:901 (1987)). Another method uses a particular framework region derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol., 151:2623 (1993)).

It is further important that antibodies be humanized with retention of high binding affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art.

Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Various forms of a humanized anti-Ovr110 antibody are contemplated. For example, the humanized antibody may be an antibody fragment, such as a Fab, which is optionally conjugated with one or more cytotoxic agent(s) in order to generate an immunoconjugate. Alternatively, the humanized antibody may be an intact antibody, such as an intact IgG1 antibody.

Human Antibodies

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggemann et al., Year in Immuno., 7:33 (1993); U.S. Pat. Nos. 5,545,806, 5,569,825, 5,591,669 (all of GenPharm); 5,545,807; and Alternatively, phage display technology (McCafferty et al., Nature 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, Kevin S. and Chiswell, David J., Current Opinion in Structural Biology 3:564-571 (1993). Several sources of V-gene segments can be used for phage display. Clackson et al., Nature, 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222:581-597 (1991), or Griffith et al., EMBO J. 12:725-734 (1993). See, also, U.S. Pat. Nos. 5,565,332 and 5,573,905. As discussed above, human antibodies may also be generated by in vitro activated B cells (see U.S. Pat. Nos. 5,567,610 and 5,229,275).

Antibody Fragments

In certain circumstances there are advantages of using antibody fragments, rather than whole antibodies. The smaller size of the fragments allows for rapid clearance, and may lead to improved access to solid tumors. Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from E coli, thus allowing the facile production of large amounts of these fragments. Antibody fragments can be isolated from the antibody phage libraries discussed above. Alternatively, Fab'-SH fragments can be directly recovered from E. coli and chemically coupled to form F(ab)2 fragments (Carter et al., Bio/Technology 10: 163-167 (1992)). According to another approach, F(ab)2 fragments can be isolated directly from recombinant host cell culture. Fab and F(ab)2 fragment with increased in vivo half-life comprising a salvage receptor binding epitope residues are described in U.S. Pat. No. 5,869,046. Other techniques for the production of antibody fragments will be apparent to the skilled practitioner. The antibody of choice may also be a single chain Fv fragment (scFv). See WO 93/16185; U.S. Pat. Nos. 5,571,894; and 5,587,458. Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. See Antibody Engineering, ed. Borrebaeck, supra. The antibody fragment may also be a "linear antibody", e.g., as described in U.S. Pat. No. 5,641,870 for example. Such linear antibody fragments may be monospecific or bispecific.

Bispecific Antibodies

Bispecific antibodies are antibodies that have binding specificities for at least two different epitopes. Exemplary bispecific antibodies may bind to two different epitopes of the Ovr110 protein. Other such antibodies may combine an Ovr110 binding site with a binding site for another protein. Alternatively, an anti-Ovr110.Arm may be combined with an arm which binds to a triggering molecule on a leukocyte such as a Tcell receptor molecule (e.g. C133), or Fc receptors for IgG (FcγR), such as FcγRI (CD64), FcγRII (CD32) and FcγRIII (CD16), so as to focus and localize cellular defense mechanisms to the Ovr110-expressing cell. Bispecific antibodies may also be used to localize cytotoxic agents to cells which express Ovr110. These antibodies possess an Ovr110-binding arm and an arm which binds the cytotoxic agent (e.g. saporin, anti-interferon-α, vinca alkaloid, ricin A chain, methotrexate or radioactive isotope hapten). Bispecific antibodies can be prepared as full length antibodies or antibody fragments (e.g. F(ab)2 bispecific antibodies). WO 96/16673 describes a bispecific anti-ErbB2/anti-FcγRIII antibody and U.S. Pat. No. 5,837,234 discloses a bispecific anti-ErbB2/anti-FcγRI antibody. A bispecific anti-ErbB2/Fcα antibody is shown in WO98/02463. U.S. Pat. No. 5,821,337 teaches a bispecific anti-ErbB2/anti-CD3 antibody.

Methods for making bispecific antibodies are known in the art. Traditional production of full length bispecific antibodies is based on the co-expression of two immunoglobulin heavy chain-light chain pairs, where the two chains have different specificities (Millstein et al., Nature, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., EMBO J., 10:3655-3659 (1991).

According to a different approach, antibody variable domains with the desired binding specificities (antibody-antigen combining sites) are fused to immunoglobulin constant domain sequences. Preferably, the fusion is with an Ig heavy chain constant domain, comprising at least part of the hinge, $C_H2$, and $C_H3$ regions. It is preferred to have the first heavy-chain constant region (CHI) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant affect on the yield of the desired chain combination.

Preferably, the bispecific antibodies in this approach are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology, 121:210 (1986).

According to another approach described in U.S. Pat. No. 5,731,168, the interface between a pair of antibody molecules can be engineered to maximize the percentage of heterodimers which are recovered from recombinant cell culture. The preferred interface comprises at least a part of the CH3 domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676, 980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science, 229: 81 (1985) describe a procedure wherein intact antibodies are proteolytically cleaved to generate F(ab')2 fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from E. coli, which can be chemically coupled to form bispecific antibodies. Shalaby et al., J. Exp. Med., 175: 217-225 (1992) describe the production of a fully humanized bispecific antibody F(ab')2 molecule. Each Fab' fragment was separately secreted from E. coli and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol., 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers.

The "diabody" technology described by Hollinger et al., Proc. Natl. Acad. Sci. USA, 90:6444-6448 (1993) has provided an alternative mechanism for making bispecific antibody fragments. The fragments comprise a VH connected to a VL by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruber et al., J. Immunol., 152:5368 (1994).

Antibodies with more than two valencies are contemplated. For example, trispecific antibodies can be prepared. Tutt et al. J. Immunol. 147: 60 (1991).

Multivalent Antibodies

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1(X1n-VD2-(X2)n-Fc, wherein VD1 is a first variable domain, VD2 is a second variable domain, Fc is one polypeptide chain of an Fc region, XI and X2 represent an amino acid or polypeptide, and n is 0 or 1. For instance, the polypeptide chain(s) may comprise: VH-CHI-flexible linker-VH-CHI-Fc region chain; or VH-CHI-VH-CHI-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

Other Amino Acid Sequence Modifications

Amino acid sequence modification(s) of the anti-Ovr110 antibodies described herein are contemplated. For example, it may be desirable to improve the binding affinity and/or other biological properties of the antibody. Amino acid sequence variants of the anti-Ovr110 antibody are prepared by introducing appropriate nucleotide changes into the anti-Ovr110 antibody nucleic acid, or by peptide synthesis.

Such modifications include, for example, deletions from, and/or insertions into, and/or substitutions of, residues within the amino acid sequences of the anti-Ovr110 antibody. Any combination of deletion, insertion, and substitution is made to arrive at the final construct, provided that the final construct possesses the desired characteristics. The amino acid changes also may alter post-translational processes of the anti-Ovr110 antibody, such as changing the number or position of glycosylation sites.

A useful method for identification of certain residues or regions of the anti-Ovr110 antibody that are preferred locations for mutagenesis is called "alanine scanning mutagenesis" as described by Cunningham and Wells in Science, 244:1081-1085 (1989). Here, a residue or group of target residues within the anti-Ovr110 antibody are identified (e.g., charged residues such as arg, asp, his, lys, and glu) and replaced by a neutral or negatively charged amino acid (most preferably alanine or polyalanine) to affect the interaction of the amino acids with Ovr110 antigen.

Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at a target codon or region and the expressed anti-Ovr110 antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an anti-Ovr110 antibody with an N-terminal methionyl residue or the antibody fused to a cytotoxic polypeptide. Other insertional variants of the anti-Ovr110 antibody molecule include the fusion to the N- or C-terminus of the anti-Ovr110 antibody to an enzyme (e.g. for ADEPT) or a fusion to a polypeptide which increases the serum half-life of the antibody.

Another type of variant is an amino acid substitution variant. These variants have at least one amino acid residue in the anti-Ovr110 antibody molecule replaced by a different residue. The sites of greatest interest for substitutional mutagenesis include the hypervariable regions, but FR alterations are also contemplated. Conservative substitutions are shown in Table I under the heading of "preferred substitutions". If such substitutions result in a change in biological activity, then more substantial changes, denominated "exemplary substitutions" in Table 1, or as further described below in reference to amino acid classes, may be introduced and the products screened for a desired characteristic.

TABLE I

Amino Acid Substitutions

| Original | Exemplary Substitutions | Preferred Substitutions |
|---|---|---|
| Ala (A) | val; leu; ile | Val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; | leu |
| Leu (L) | norleucine; ile; val; met; ala; | ile |
| Lys (K) | arg; gin; asn | arg |
| Met (M) | leu; phe; ile | leu |
| Phe (F) | leu; val; ile; ala; tyr | tyr |
| Pro (P) | ala | ala |
| Ser (S) | thr | thr |
| Thr (T) | ser | ser |
| Trp (W) | tyr; phe | tyr |
| Tyr (Y) | trp; phe; thr; ser | Phe |
| Val (V) | ile; leu; met; phe; ala; | leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile; (2) neutral hydrophilic: cys, ser, thr, (3) acidic: asp, glu; (4) basic: asn, gin, his, lys, arg; (5) residues that influence chain orientation: gly, pro; and (6) aromatic: trp, tyr, phe.

Non-conservative substitutions will entail exchanging a member of one of these classes for another class. Any cysteine residue not involved in maintaining the proper conformation of the anti-Ovr110 antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

A particularly preferred type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g. 6-7 sites) are mutated to generate all possible amino acid substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and human Ovr110. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of the anti-Ovr110 antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared nucleic acid molecule encoding a variant or a non-variant version of the anti-Ovr110 antibody.

It may be desirable to modify the antibody of the invention with respect to effector function, e.g. so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp Med. 176:1191-1195 (1992) and Shopes, B. J. Immunol. 148:2918-2922 (1992). Homodimeric antibodies with enhanced anti-tumor activity may also be prepared using heterobifunctional cross-linkers as described in Wolff et al. Cancer Research 53:2560-2565 (1993). Alternatively, an antibody can be engineered which has dual Fc regions and may thereby have enhanced complement lysis and ADCC capabilities. See Stevenson et al. Anti-Cancer Drug Design 3:219-230 (1989).

To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of the antibody.

Screening for Antibodies with the Desired Properties

Techniques for generating antibodies have been described above. One may further select antibodies with certain biological characteristics, as desired.

The growth inhibitory effects of an anti-Ovr110 antibody of the invention may be assessed by methods known in the art, e.g., using cells which express Ovr110 either endogenously or following transfection with the Ovr110 gene. For example, the tumor cell lines and Ovr110-transfected cells provided in Example 1 below may be treated with an anti-Ovr110 monoclonal antibody of the invention at various concentrations for a few days (e.g., 2-7) days and stained with crystal violet or MTT or analyzed by some other colorimetric assay. Another method of measuring proliferation would be by comparing $^3$H-thymidine uptake by the cells treated in the presence or absence an anti-Ovr110 antibody of the invention. After antibody treatment, the cells are harvested and the amount of radioactivity incorporated into the DNA quantitated in a scintillation counter. Appropriated positive controls include treatment of a selected cell line with a growth inhibitory antibody known to inhibit growth of that cell line. Growth inhibition of tumor cells in vivo can be determined in various ways such as is described in the Experimental Examples section below. Preferably, the tumor cell is one that over-expresses Ovr110. Preferably, the anti-Ovr110 antibody will inhibit cell proliferation of an Ovr110-expressing tumor cell in vitro or in vivo by about 25-100% compared to the untreated tumor cell, more preferably, by about 30-100%, and even more preferably by about 50-100% or 70-100%, at an antibody concentration of about 0.5 to 30 µg/ml. Growth inhibition can be measured at an antibody concentration of about 0.5 to 30 µg/ml or about 0.5 nM to 200 nM in cell culture, where the growth inhibition is determined 1-10 days after exposure of the tumor cells to the antibody. The antibody is growth inhibitory in vivo if administration of the anti-Ovr110 antibody at about 1 µg/kg to about 100 mg/kg body weight results in reduction in tumor size or tumor cell proliferation within about 5 days to 3 months from the first administration of the antibody, preferably within about 5 to 30 days.

To select for antibodies which induce cell death, loss of membrane integrity as indicated by, e.g., propidium iodide (PI), trypan blue or 7AAD uptake may be assessed relative to a control. A PI uptake assay can be performed in the absence of complement and immune effector cells. Ovr110-expressing tumor cells are incubated with medium alone or medium containing of the appropriate monoclonal antibody at e.g., about 10 µg/ml. The cells are incubated for a 3 day time period. Following each treatment, cells are washed and aliquoted into 35 mm strainer-capped 12×75 tubes (1 ml per tube, 3 tubes per treatment group) for removal of cell clumps. Tubes then receive PI (10 µg/ml). Samples may be analyzed using a FACSCAN™ flow cytometer and FACSCON-VERT™ CellQuest software (Becton Dickinson). Those antibodies which induce statistically significant levels of cell death as determined by PI uptake may be selected as cell death-inducing antibodies.

To screen for antibodies which bind to an epitope on Ovr110 bound by an antibody of interest, e.g., the Ovr110 antibodies of this invention, a routine cross-blocking assay such as that describe in *Antibodies, A Laboratory Manual*, Cold Spring Harbor Laboratory, Ed Harlow and David Lane (1988), can be performed. This assay can be used to determine if a test antibody binds the same site or epitope as an anti-Ovr110 antibody of the invention. Alternatively, or additionally, epitope mapping can be performed by methods known in the art. For example, the antibody sequence can be mutagenized such as by alanine scanning, to identify contact residues. The mutant antibody is initially tested for binding with polyclonal antibody to ensure proper folding. In a different method, peptides corresponding to different regions of Ovr110 can be used in competition assays with the test antibodies or with a test antibody and an antibody with a characterized or known epitope.

For example, a method to screen for antibodies that bind to an epitope which is bound by an antibody this invention may comprise combining an Ovr110-containing sample with a test antibody and an antibody of this invention to form a mixture, the level of Ovr110 antibody bound to Ovr110 in the mixture is then determined and compared to the level of Ovr110 antibody bound in the mixture to a control mixture, wherein the level of Ovr110 antibody binding to Ovr110 in the mixture as compared to the control is indicative of the test antibody's binding to an epitope that is bound by the anti-Ovr110 antibody of this invention. The level of Ovr110 antibody bound to Ovr110 is determined by ELISA. The control may be a positive or negative control or both. For example, the control may be a mixture of Ovr110, Ovr110 antibody of this invention and an antibody known to bind the epitope bound by the Ovr110 antibody of this invention. The anti-Ovr110 antibody labeled with a label such as those disclosed herein. The Ovr110 may be bound to a solid support, e.g., a tissue culture plate or to beads, e.g., sepharose beads.

Immunoconjugates

The invention also pertains to therapy with immunoconjugates comprising an antibody conjugated to an anti-cancer agent such as a cytotoxic agent or a growth inhibitory agent.

Chemotherapeutic agents useful in the generation of such immunoconjugates have been described above. Conjugates of an antibody and one or more small molecule toxins, such as a calicheamicin, maytansinoids, a trichothene, and CC1065, and the derivatives of these toxins that have toxin activity, are also contemplated herein.

Maytansine and Maytansinoids

Preferably, an anti-Ovr110 antibody (full length or fragments) of the invention is conjugated to one or more maytansinoid molecules.

Maytansinoids are mitotic inhibitors which act by inhibiting tubulin polymerization. Maytansine was first isolated from the cast African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533, the disclosures of which are hereby expressly incorporated by reference.

Maytansinoid-Antibody Conjugates

In an attempt to improve their therapeutic index, maytansine and maytansinoids have been conjugated to antibodies specifically binding to tumor cell antigens. Immunoconjugates containing maytansinoids and their therapeutic use are disclosed, for example, in U.S. Pat. Nos. 5,208,020, 5,416,064 and European Patent EP 0 425 235 B1, the disclosures of which are hereby expressly incorporated by reference. Liu et al., Proc. Natl. Acad. Sci. USA 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al. Cancer Research 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA. 1-maytansonoid conjugate was tested in vitro on the human breast cancer cell line SK-BR-3, which expresses 3×10 5 HER-2 surface antigens per cell. The drug conjugate achieved a degree of cytotoxicity similar to the free maytansonid drug, which could be increased by increasing the number of maytansinoid molecules per antibody molecule. The A7-maytansinoid conjugate showed low systemic cytotoxicity in mice.

Anti-Ovr110 Antibody-Maytansinoid Conjugates (Immunoconjugates)

Anti-Ovr110 antibody-maytansinoid conjugates are prepared by chemically linking an anti-Ovr110 antibody to a maytansinoid molecule without significantly diminishing the biological activity of either the antibody or the maytansinoid molecule. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B 1, and Chari et al. Cancer Research 52: 127-131 (1992). The linking groups include disulfide groups, thioether groups, acid labile groups, photolabile groups, peptidase labile groups, or esterase labile groups, as disclosed in the above-identified patents, disulfide and thioether groups being preferred. Conjugates of the antibody and maytansinoid may be made using a variety of bifunctional protein coupling agents such as N-succinimidyl (2-pyridyidithio) propionate (SPDP), succinimidyl-(N-maleimidomethyl) cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as his (p-azidobenzoyl) hexanediamine), bis-diazonium derivatives (such as bis-(diazoniumbenzoyl)-ethylenediamine), diisocyanates (such as toluene 2,6diisocyanate), and bis-active fluorine compounds (such as 1,5-difluoro-2,4-dinitrobenzene). Particularly preferred coupling agents include N-succinimidyl (2-pyridyldithio) propionate (SPDP) (Carlsson et al., Biochem. J. 173:723-737 [1978]) and N-succinimidyl (2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. Preferably, the linkage is formed at the C-3 position of maytansinol or a maytansinol analogue.

Calicheamicin

Another immunoconjugate of interest comprises an anti-Ovr110 antibody conjugated to one or more calicheamicin molecules. The calicheamicin family of antibiotics are capable of producing double-stranded DNA breaks at subpicomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, $\gamma_1^I$, $\alpha_2^I$, $\alpha_3^I$, N-acetyl-$\gamma_1^I$, PSAG and $\theta_1^I$, (Hinman et al. Cancer Research 53: 3336 (1993), Lode et al. Cancer Research 5 8: 2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Other Cytotoxic Agents

Other antitumor agents that can be conjugated to the anti-Ovr110 antibodies of the invention include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296). Enzymatically active toxins and fragments thereof which can be used include diphtheria A chain, 1 5 nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993. The present invention further contemplates an immunoconjugate formed between an antibody and a compound with nucleolytic activity (e.g. a ribonuclease or a DNA endonuclease such as a deoxyribonuclease; DNase).

For selective destruction of the tumor, the antibody may comprise a highly radioactive atom. A variety of radioactive isotopes are available for the production of radioconjugated anti-Ovr110 antibodies. Examples include $At^{211}$, $I^{131}$, $I^{125}$, $In^{111}$, $Y^{90}$, $Re^{186}$, $Re^{188}$, $Sm^{153}$, $Bi^{212}$, $P^{32}$, and radioactive isotopes of Lu. When the conjugate is used for diagnosis, it may comprise a radioactive atom for scintigraphic studies, for example $Tc^{99M}$ or $I^{123}$, or a spin label for nuclear magnetic resonance (NMR) imaging (also known as magnetic resonance imaging, mri), such as iodine-123, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $Tc^{99M}$, $I^{123}$, $In^{111}$, $Re^{186}$, $Re^{188}$, can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate iodine "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl (2-pyridyldithio) propionate (SPDP), succinimidyl (N-maleimidomethyl) cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6diisocyanate), and bis-active fluorine compounds (such as 1,5-difluoro-2,4-dinitrobenzene). For example, a ricin immunotoxin can be prepared as described in Vitetta et al. Science 238: 1098 (1987). Carbon labeled 1-isothiocyanatobenzyl methyldiethylene triaminepentaacetic acid (MX-DTPA) is an exemplary chelating agent for conjugation of radionucleotide to the antibody. See WO 94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al. Cancer Research 52: 127-131 (1992); U.S. Pat. No. 5,208, 020) may be used.

Alternatively, a fusion protein comprising the anti-Ovr110 antibody and cytotoxic agent may be made, e.g. by recombinant techniques or peptide synthesis. The length of DNA may comprise respective regions encoding the two portions of the conjugate either adjacent one another or separated by a region encoding a linker peptide which does not destroy the desired properties of the conjugate.

In addition, the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionucleotide).

Antibody Dependent Enzyme Mediated Prodrug Therapy (ADEPT)

The antibodies of the present invention may also be used in ADEPT by conjugating the antibody to a prodrug-activating enzyme which converts a prodrug (e.g. a peptidyl chemotherapeutic agent, see WO81/01145) to an active anti-cancer drug. See, for example, WO 88/07378 and U.S. Pat. No. 4,975,278.

The enzyme component of the immunoconjugate useful for ADEPT includes any enzyme capable of acting on a prodrug in such a way so as to covert it into its more active, cytotoxic form. Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as O-galactosidase and neuraminidase useful for converting glycosylated prodrugs into free drugs; P-lactamase useful for converting drugs derivatized with P-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, Nature 328: 457-458 (1987)). Antibody-abzyme conjugates can be prepared as described herein for delivery of the abzyme to a tumor cell population. The enzymes of this invention can be covalently bound to the anti-Ovr110 antibodies by techniques well known in the art such as the use of the heterobifunctional crosslinking reagents discussed above.

Alternatively, fusion proteins comprising at least the antigen binding region of an antibody of the invention linked to at least a functionally active portion of an enzyme of the invention can be constructed using recombinant DNA techniques well known in the art (see, e.g., Neuberger et al., Nature, 312: 604-608 (1984).

Other Antibody Modifications

Other modifications of the antibody are contemplated herein. For example, the antibody may be linked to one of a variety of nonproteinaceous polymers, e.g., polyethylene glycol, polypropylene glycol, polyoxyalkylenes, or copolymers of polyethylene glycol and polypropylene glycol. The antibody also may be entrapped in microcapsules prepared, for example, by coacervation techniques or by interfacial polymerization (for example, hydroxymethylcellulose or gelatin-microcapsules and poly(methylmethacylate) microcapsules, respectively), in colloidal drug delivery systems (for example, liposomes, albumin microspheres, microemulsions, nano-particles and nanocapsules), or in macroemulsions. Such techniques are disclosed in Remington's Pharmaceutical Sciences, 16th edition, Oslo, A., Ed., (1980).

The anti-Ovr110 antibodies disclosed herein may also be formulated as immunoliposomes. A "liposome" is a small vesicle composed of various types of lipids, phospholipids and/or surfactant which is useful for delivery of a drug to a mammal. The components of the liposome are commonly arranged in a bilayer formation, similar to the lipid arrangement of biological membranes. Liposomes containing the antibody are prepared by methods known in the art, such as described in Epstein et al., Proc. Natl. Acad. Sci. USA, 82:3688 (1985); Hwang et al., Proc. Natl. Acad. Sci. USA, 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extuded through filters of defined pore size to yield liposomes with the desired diameter. Fab' fragments of the antibody of the present invention can be conjugated to the liposomes as described in Martin et al. J. Biol. Chem. 257: 286-288 (1982) via a disulfide interchange reaction. A chemotherapeutic agent is optionally contained within the liposome. See Gabizon et al. J. National Cancer Inst. 81(19)1484 (1989).

Vectors, Host Cells, and Recombinant Methods

The invention also provides isolated nucleic acid molecule encoding the humanized anti-Ovr110 antibody, vectors and host cells comprising the nucleic acid, and recombinant techniques for the production of the antibody. For recombinant production of the antibody, the nucleic acid molecule encoding it is isolated and inserted into a replicable vector for further cloning (amplification of the DNA) or inserted into a vector in operable linkage with a promoter for expression. DNA encoding the monoclonal antibody is readily isolated and sequenced using conventional procedures (e.g., by using oligonucleotide probes that are capable of binding specifically to nucleic acid molecules encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

Signal Sequence Component

The anti-Ovr110 antibody of this invention may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells that do not recognize and process the native anti-Ovr110 antibody signal sequence, the signal sequence is substituted by a prokaryotic signal sequence selected, for example, from the group of the alkaline phosphatase, penicillinase, 1pp, or heat-stable enterotoxin II leaders. For yeast secretion the native signal sequence may be substituted by, e.g., the yeast invertase leader, oc factor leader (including *Saccharomyces* and *Kluyveromyces* cc-factor leaders), or acid phosphatase leader, the *C albicans* glucoamylase leader, or the signal described in WO 90/13646. In mammalian cell expression, mammalian signal sequences as well as viral secretory leaders, for example, the herpes simplex gD signal, are available. The DNA for such precursor region is ligated in reading frame to DNA encoding the anti-Ovr110 antibody.

Origin of Replication

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2 μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*. One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the anti-Ovr110 antibody nucleic acid, such as DHFR, thymidine kinase, metallothionein-I and -11, preferably primate metallothionein genes, adenosine deaminase, ornithine decarboxylase, etc. For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., ATCC CRL-9096).

Alternatively, host cells particularly wild-type hosts that contain endogenous DHFR) transformed or co-transformed with DNA sequences encoding anti-Ovr110 antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., Nature, 282:39 (1979)). The trp1 gene provides a selection marker for a mutant strain of yeast lacking the ability to grow in tryptophan, for example, ATCC No. 44076 or PEP4 Jones, Genetics, 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 pm circular plasmid pKDI can be used for transformation of *Kluyveromyces* yeasts. Alternatively, an expression system for large-scale production of recombinant calf chymosin was reported for *K. lactis*. Van den Berg, Bio/Technology, 8:135 (1990). Stable multi-copy expression vectors for secretion of mature recombinant human serum albumin by industrial strains of *Kluyveromyces* have also been disclosed. Fleer et al., Bio/Technology, 9:968-975 (1991).

Promoter Component

Expression and cloning vectors usually contain a promoter that is recognized by the host organism and is operably linked to the anti-Ovr110 antibody nucleic acid. Promoters suitable for use with prokaryotic hosts include the phoA promoter, P-lactamase and lactose promoter systems, alkaline phosphatase promoter, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the anti-Ovr110 antibody.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors. Examples of suitable promoter sequences for use with yeast hosts include the promoters for 3-phosphoglycerate kinase or other glycolytic enzymes, such as enolase, glyceraldehyde phosphate dehydrogenase, hexokinase, pyruvate decarboxylase, phosphofructokinase, glucose phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde phosphate dehydrogenase, and enzymes responsible for maltose and galactose utilization. Suitable vectors and promoters for use in yeast expression are further described in EP 73,657. Yeast enhancers also are advantageously used with yeast promoters.

Anti-Ovr110 antibody transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian, Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment A system for expressing DNA in mammalian hosts using the bovine papilloma virus as a vector is disclosed in U.S. Pat. No. 4,419, 446. A modification of this system is described in U.S. Pat. No. 4,601,978. See also Reyes et al., Nature 297:598-601 (1982) on expression of human P-interferon cDNA in mouse cells under the control of a thymidine kinase promoter from herpes simplex virus. Alternatively, the Rous Sarcoma Virus long terminal repeat can be used as the promoter.

Enhancer Element Component

Transcription of a DNA encoding the anti-Ovr110 antibody of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the anti-Ovr110 antibody-encoding sequence, but is preferably located at a site 5' from the promoter.

Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3' untranslated regions of eukaryotic or viral DNAs or cDNAs. These regions contain nucleotide segments transcribed as polyadenylated fragments in the untranslated portion of the mRNA encoding anti-Ovr110 antibody. One useful transcription termination component is the bovine growth hormone polyadenylation region. See WO 94/11026 and the expression vector disclosed therein.

Selection and Transformation of Host Cells

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as *Bacilli* such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W31 10 (ATCC 27,325) are suitable. These examples are illustrative rather than limiting.

Full length antibody, antibody fragments, and antibody fusion proteins can be produced in bacteria, in particular when glycosylation and Fc effector function are not needed, such as when the therapeutic antibody is conjugated to a cytotoxic agent (e.g., a toxin) and the immunoconjugate by itself shows effectiveness in tumor cell destruction. Full length antibodies have greater half life in circulation. Production in *E. coli* is faster and more cost efficient. For expression of antibody fragments and polypeptides in bacteria, see, e.g., U.S. Pat. No. 5,648,237 (Carter et. al.), U.S. Pat. No. 5,789, 199 (Joly et al.), and U.S. Pat. No. 5,840,523 (Simmons et al.) which describes translation initiation region (TIR) and signal sequences for optimizing expression and secretion, these patents incorporated herein by reference. After expression, the antibody is isolated from the *E. coli* cell paste in a soluble fraction and can be purified through, e.g., a protein A or G column depending on the isotype. Final purification can be carried out similar to the process for purifying antibody expressed e.g., in CHO cells.

In addition to prokaryotes, eukaryotic microbes such as filamentous fungi or yeast are suitable cloning or expression hosts for anti-Ovr110 antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183, 070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated anti-Ovr110 antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, *Arabidopsis* and tobacco can also be utilized as hosts.

Cloning and expression vectors useful in the production of proteins in plant cell culture are known to those of skill in the art. See e.g. Hiatt et al., Nature (1989) 342: 76-78, Owen et al. (1992) Bio/Technology 10: 790-794, Artsaenko et al. (1995) The Plant J 8: 745-750, and Fecker et al. (1996) Plant Mol Biol 32: 979-986.

However, interest has been greatest in vertebrate cells, and propagation of vertebrate cells in culture (tissue culture) has become a routine procedure. Examples of useful mammalian host cell lines are monkey kidney CVI line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/–DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CVI ATCC CCL 70); African green monkey kidney cells (VERO-76, ATCC CRL1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, 1413 8065); mouse mammary tumor (MMT 060562, ATCC CCL5 1); TRI cells (Mather et al., Annals N.Y. Acad. Sci. 383:44-68 (1982)); MRC 5 cells; FS4 cells; and a human hepatoma line (Hep G2).

Host cells are transformed with the above-described expression or cloning vectors for anti-Ovr110 antibody production and cultured in conventional nutrient media modified as appropriate for inducing promoters, selecting transformants, or amplifying the genes encoding the desired sequences.

Culturing Host Cells

The host cells used to produce the anti-Ovr110 antibody of this invention may be cultured in a variety of media. Commercially available media such as Ham's FIO (Sigma), Minimal Essential Medium (MEM)(Sigma), RPMI-1640 (Sigma), and Dulbecco's Modified Eagle's Medium (DMEM)(Sigma) are suitable for culturing the host cells. In addition, any of the media described in Ham et al., Meth. Enz. 58:44 (1979), Barnes et al., Anal. Biochem. 102:255 (1980), U.S. Pat. No. 4,767,704; 4,657,866; 4,927,762; 4,560,655; or 5,122,469; WO 90/03430; WO 87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Purification of Anti-Ovr110 Antibody

When using recombinant techniques, the antibody can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., Bio/Technology 10: 163-167 (1992) describe a procedure for isolating antibodies which are secreted to the periplasmic space of *E coli*. Briefly, cell paste is thawed in the presence of sodium acetate (pH 3.5), EDTA, and phenylmethylsulfonylfluoride (PMSF) over about 30 min. Cell debris can be removed by centrifugation.

Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., J. Immunol. Meth. 62:1-13 (1983)). Protein G is recommended for all mouse isotypes and for human γ3 (Guss et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SIDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Pharmaceutical Formulations

Pharmaceutical formulations of the antibodies used in accordance with the present invention are prepared for storage by mixing an antibody having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as acetate, Tris, phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol, and mcresol); low molecular weight (less than about 10 residues) polypeptides; proteins, such as serum albumin, gelatin, or immunoglobulins; hydrophilic polymers such as polyvinylpyllolidone; amino acids such as glycine, glutamine, asparagine, histidine, arginine, or lysine; monosaccharides, disaccharides, and other carbohydrates including glucose, mannose, or dextrins; chelating agents such as EDTA; tonicifiers such as trehalose and sodium chloride; sugars such as sucrose, mannitol, trehalose or sorbitol; surfactant such as polysorbate; salt-forming counter-ions such as sodium; metal complexes (e.g. Zn-protein complexes); and/or non-ionic surfactants such as TWEEN™, PLURONICS™ or polyethylene glycol (PEG).

The antibody preferably comprises the antibody at a concentration of between 5-200 mg/ml, preferably between 10-100 mg/ml.

The formulation herein may also contain more than one active compound as necessary for the particular indication being treated, preferably those with complementary activities that do not adversely affect each other. For example, in addition to the anti-Ovr110 antibody which internalizes, it may be desirable to include in the one formulation, an additional antibody, e.g. a second anti-Ovr110 antibody which binds a different epitope on Ovr110, or an antibody to some other target such as a growth factor that affects the growth of the particular cancer. Alternatively, or additionally, the composition may further comprise a chemotherapeutic agent, cytotoxic agent, cytokine, growth inhibitory agent, anti-hormonal agent, and/or cardioprotectant. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatinmicrocapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semi-permeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−) hydroxybutyric acid.

The formulations to be used for in vivo administration must be sterile. This is readily accomplished by filtration through sterile filtration membranes.

Methods and Treatment Using Anti-Ovr110 Antibodies

According to the present invention, the anti-Ovr110 antibody that internalizes upon binding Ovr110 on a cell surface is used to treat a subject in need thereof having a cancer characterized by Ovr110-expressing cancer cells, in particular, ovarian, pancreatic, lung or breast cancer, such as ovarian serous adenocarcinoma or breast infiltrating ductal carcinoma cancer, and associated metastases.

The cancer will generally comprise Ovr110-expressing cells, such that the anti-Ovr110 antibody is able to bind thereto. While the cancer may be characterized by overexpression of the Ovr110 molecule, the present application further provides a method for treating cancer which is not considered to be an Ovr110-overexpressing cancer.

This invention also relates to methods for detecting cells which overexpress Ovr110 and to diagnostic kits useful in detecting cells expressing Ovr110 or in detecting Ovr110 in serum from a patient. The methods may comprise combining a cell-containing test sample with an antibody of this invention, assaying the test sample for antibody binding to cells in the test sample and comparing the level of antibody binding in the test sample to the level of antibody binding in a control sample of cells. A suitable control is, e.g., a sample of normal cells of the same type as the test sample or a cell sample known to be free of Ovr110 overexpressing cells. A level of Ovr110 binding higher than that of such a control sample would be indicative of the test sample containing cells that overexpress Ovr110. Alternatively the control may be a sample of cells known to contain cells that overexpress Ovr110. In such a case, a level of Ovr110 antibody binding in the test sample that is similar to, or in excess of, that of the control sample would be indicative of the test sample containing cells that overexpress Ovr110.

Ovr110 overexpression may be detected with a various diagnostic assays. For example, over expression of Ovr110 may be assayed by immunohistochemistry (IHC). Parrafin embedded tissue sections from a tumor biopsy may be subjected to the IHC assay and accorded an Ovr110 protein staining intensity criteria as follows.

Score 0 no staining is observed or membrane staining is observed in less than 10% of tumor cells.

Score 1+ a faint/barely perceptible membrane staining is detected in more than 10% of the tumor cells. The cells are only stained in part of their membrane.

Score 2+ a weak to moderate complete membrane staining is observed in more than 10% of the tumor cells.

Score 3+ a moderate to strong complete membrane staining is observed in more than 10% of the tumor cells.

Those tumors with 0 or 1+ scores for Ovr110 expression may be characterized as not overexpressing Ovr110, whereas those tumors with 2+ or 3+ scores may be characterized as overexpressing Ovr110.

Alternatively, or additionally, FISH assays such as the INFORM™ (sold by Ventana, Ariz.) or PATHVISION™ (VySiS, Ill.) may be carried out on formalin-fixed, paraffin-embedded tumor tissue to determine the extent (if any) of Ovr110 overexpression in the tumor. Ovr110 overexpression or amplification may be evaluated using an in vivo diagnostic assay, e.g. by administering a molecule (such as an antibody of this invention) which binds Ovr110 and which is labeled with a detectable label (e.g. a radioactive isotope or a fluorescent label) and externally scanning the patient for localization of the label.

A sample suspected of containing cells expressing or overexpressing Ovr110 is combined with the antibodies of this invention under conditions suitable for the specific binding of the antibodies to Ovr110. Binding and/or internalizing the Ovr110 antibodies of this invention is indicative of the cells expressing Ovr110. The level of binding may be determined and compared to a suitable control, wherein an elevated level of bound Ovr110 as compared to the control is indicative of Ovr110 overexpression. The sample suspected of containing cells overexpressing Ovr110 may be a cancer cell sample, particularly a sample of an ovarian cancer, e.g. ovarian serous adenocarcinoma, or a breast cancer, e.g., a breast infiltrating ductal carcinoma. A serum sample from a subject may also be assayed for levels of Ovr110 by combining a serum sample from a subject with an Ovr110 antibody of this invention, determining the level of Ovr110 bound to the antibody and comparing the level to a control, wherein an elevated level of Ovr110 in the serum of the patient as compared to a control is indicative of overexpression of Ovr110 by cells in the patient. The subject may have a cancer such as e.g., an ovarian cancer, e.g. ovarian serous adenocarcinoma, or a breast cancer, e.g., a breast infiltrating ductal carcinoma.

Currently, depending on the stage of the cancer, ovarian, pancreatic, lung or breast cancer treatment involves one or a combination of the following therapies: surgery to remove the cancerous tissue, radiation therapy, androgen deprivation (e.g., hormonal therapy), and chemotherapy. Anti-Ovr110 antibody therapy may be especially desirable in elderly patients who do not tolerate the toxicity and side effects of chemotherapy well, in meta static disease where radiation therapy has limited usefulness, and for the management of prostatic carcinoma that is resistant to androgen deprivation treatment. The tumor targeting and internalizing anti-Ovr110 antibodies of the invention are useful to alleviate Ovr110-expressing cancers, e.g., ovarian, pancreatic, lung or breast cancers upon initial diagnosis of the disease or during relapse. For therapeutic applications, the anti-Ovr110 antibody can be used alone, or in combination therapy with, e.g., hormones, antiangiogens, or radiolabelled compounds, or with surgery, cryotherapy, and/or radiotherapy, notably for ovarian, pancreatic, lung or breast cancers, also particularly where shed cells cannot be reached. Anti-Ovr110 antibody treatment can be administered in conjunction with other forms of conventional therapy, either consecutively with, pre- or post-conventional therapy, Chemotherapeutic drugs such as Taxotere® (docetaxel), Taxol® (palictaxel), estramustine and mitoxantrone are used in treating metastatic and hormone refractory ovarian, pancreatic, lung or breast cancer, in particular, in good risk patients. In the present method of the invention for treating or alleviating cancer, in particular, androgen independent and/or meta static ovarian, pancreatic, lung or breast cancer, the cancer patient can be administered anti-Ovr110 antibody in conduction with treatment with the one or more of the preceding chemotherapeutic agents. In particular, combination therapy with palictaxel and modified derivatives (see, e.g., EP0600517) is contemplated. The anti-Ovr110 antibody will be administered with a therapeutically effective dose of the chemotherapeutic agent. The anti-Ovr110 antibody may also be administered in conjunction with chemotherapy to enhance the activity and efficacy of the chemotherapeutic agent, e.g., paclitaxel. The Physicians' Desk Reference (PDR) discloses dosages of these agents that have been used in treatment of various cancers. The dosing regimen and dosages of these aforementioned chemotherapeutic drugs that are therapeutically effective will depend on the particular cancer being treated, the extent of the disease and other factors familiar to the physician of skill in the art and can be determined by the physician.

Particularly, an immunoconjugate comprising the anti-Ovr110 antibody conjugated with a cytotoxic agent may be administered to the patient. Preferably, the immunoconjugate bound to the Ovr110 protein is internalized by the cell, resulting in increased therapeutic efficacy of the immunoconjugate in killing the cancer cell to which it binds. Preferably, the cytotoxic agent targets or interferes with the nucleic acid in the cancer cell. Examples of such cytotoxic agents are described above and include maytansin, maytansinoids, saporin, gelonin, ricin, calicheamicin, ribonucleases and DNA endonucleases.

The anti-Ovr110 antibodies or immunoconjugates are administered to a human patient, in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. The antibodies or immunoconjugates may be injected directly into the tumor mass. Intravenous or subcutaneous administration of the antibody is preferred. Other therapeutic regimens may be combined with the administration of the anti-Ovr110 antibody.

The combined administration includes co-administration, using separate formulations or a single pharmaceutical formulation, and consecutive administration in either order, wherein preferably there is a time period while both (or all) active agents simultaneously exert their biological activities. Preferably such combined therapy results in a synergistic therapeutic effect.

It may also be desirable to combine administration of the anti-Ovr110 antibody or antibodies, with administration of an antibody directed against another tumor antigen associated with the particular cancer. As such, this invention is also directed to an antibody "cocktail" comprising one or more antibodies of this invention and at least one other antibody which binds another tumor antigen associated with the Ovr110-expressing tumor cells. The cocktail may also comprise antibodies that are directed to other epitopes of Ovr110. Preferably the other antibodies do not interfere with the binding and or internalization of the antibodies of this invention.

The antibody therapeutic treatment method of the present invention may involve the combined administration of an anti-Ovr110 antibody (or antibodies) and one or more chemotherapeutic agents or growth inhibitory agents, including co-administration of cocktails of different chemotherapeutic agents. Chemotherapeutic agents include, e.g., estramustine phosphate, prednimustine, cisplatin, 5-fluorouracil, melphalan, cyclophosphamide, hydroxyurea and hydroxyureataxanes (such as paclitaxel and doxetaxel) and/or anthracycline antibiotics. Preparation and dosing schedules for such chemotherapeutic agents may be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, Md. (1992).

The antibody may be combined with an anti-hormonal compound; e.g., an anti-estrogen compound such as tamoxifen; an anti-progesterone such as onapristone (see, EP 616 812); or an anti-androgen such as flutamide, in dosages known for such molecules. Where the cancer to be treated is androgen independent cancer, the patient may previously have been subjected to anti-androgen therapy and, after the cancer becomes androgen independent, the anti-Ovr110 antibody (and optionally other agents as described herein) may be administered to the patient.

Sometimes, it may be beneficial to also co-administer a cardioprotectant (to prevent or reduce myocardial dysfunction associated with the therapy) or one or more cytokines to the patient. In addition to the above therapeutic regimes, the patient may be subjected to surgical removal of cancer cells and/or radiation therapy, before, simultaneously with, or post antibody therapy. Suitable dosages for any of the above co-administered agents are those presently used and may be lowered due to the combined action (synergy) of the agent and anti-Ovr110 antibody.

For the prevention or treatment of disease, the dosage and mode of administration will be chosen by the physician according to known criteria. The appropriate dosage of antibody will depend on the type of disease to be treated, as defined above, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Preferably, the antibody is administered by intravenous infusion or by subcutaneous injections. Depending on the type and severity of the disease, about 1 pg/kg to about 50 mg/kg body weight (e.g. about 0.1-15 mg/kg/dose) of antibody can be an initial candidate dosage for administration to the patient, whether, for example, by one or more separate administrations, or by continuous infusion. A dosing regimen can comprise administering an initial loading dose of about 4 mg/kg, followed by a weekly maintenance dose of about 2 mg/kg of the anti-Ovr110 antibody. However, other dosage regimens may be useful. A typical daily dosage might range from about 1 pg/kg to 100 mg/kg or more, depending on the factors mentioned above. For repeated administrations over several days or longer, depending on the condition, the treatment is sustained until a desired suppression of disease symptoms occurs. The progress of this therapy can be readily monitored by conventional methods and assays and based on criteria known to the physician or other persons of skill in the art.

Aside from administration of the antibody protein to the patient, the present application contemplates administration of the antibody by gene therapy. Such administration of a nucleic acid molecule encoding the antibody is encompassed by the expression "administering a therapeutically effective amount of an antibody". See, for example, WO 96/07321 published Mar. 14, 1996 concerning the use of gene therapy to generate intracellular antibodies.

There are two major approaches to introducing the nucleic acid molecule (optionally contained in a vector) into the patient's cells; in vivo and ex vivo. For in vivo delivery the nucleic acid molecule is injected directly into the patient, usually at the site where the antibody is required. For ex vivo treatment, the patient's cells are removed, the nucleic acid molecule is introduced into these isolated cells and the modified cells are administered to the patient either directly or, for example, encapsulated within porous membranes which are implanted into the patient (see, e.g. U.S. Pat. Nos. 4,892,538 and 5,283,187). There are a variety of techniques available for introducing nucleic acid molecules into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a retroviral vector.

The currently preferred in vivo nucleic acid molecule transfer techniques include transfection with viral vectors (such as adenovirus, Herpes simplex I virus, or adeno-associated virus) and lipid-based systems (useful lipids for lipid-mediated transfer of the gene are DOTMA, DOPE and DC-Chol, for example). For review of the currently known gene marling and gene therapy protocols see Anderson et at., Science 256:808-813 (1992). See also WO 93/25673 and the references cited therein.

Articles of Manufacture and Kits

The invention also relates to an article of manufacture containing materials useful for the detection for Ovr110 overexpressing cells and/or the treatment of Ovr110 expressing cancer, in particular ovarian, pancreatic, lung or breast cancer. The article of manufacture comprises a container and a composition contained therein comprising an antibody of this invention. The composition may further comprise a carrier. The article of manufacture may also comprise a label or package insert on or associated with the container. Suitable containers include, for example, bottles, vials, syringes, etc. The containers may be formed from a variety of materials such as glass or plastic. The container holds a composition which is effective for detecting Ovr110 expressing cells and/or treating a cancer condition and may have a sterile access port (for example the container may be an intravenous solution bag or a vial having a stopper pierceable by a hypodermic injection needle). At least one active agent in the composition is an anti-Ovr110 antibody of the invention. The label or package insert indicates that the composition is used for detecting Ovr110 expressing cells and/or for treating ovarian, pancreatic, lung or breast cancer, or more specifically ovarian serous adenocarcinoma or breast infiltrating ductal carcinoma cancer, in a patient in need thereof. The label or package insert may further comprise instructions for administering the antibody composition to a cancer patient. Additionally, the article of manufacture may further comprise a second container comprising a substance which detects the antibody of this invention, e.g., a second antibody which binds to the antibodies of this invention. The substance may be labeled with a detectable label such as those disclosed herein. The second container may contain e.g., a pharmaceutically-acceptable buffer, such as bacteriostatic water for injection (BWFI), phosphate-buffered saline, Ringer's solution and dextrose solution. The article of manufacture may further include other materials desirable from a commercial and user standpoint, including other buffers, diluents, filters, needles, and syringes.

Kits are also provided that are useful for various purposes, e.g., for Ovr110 cell killing assays, for purification or immunoprecipitation of Ovr110 from cells or for detecting the presence of Ovr110 in a serum sample or detecting the presence of Ovr110-expressing cells in a cell sample. For isolation and purification of Ovr110, the kit can contain an anti-Ovr110 antibody coupled to a solid support, e.g., a tissue culture plate or beads (e.g., sepharose beads). Kits can be provided which contain the antibodies for detection and quantitation of Ovr110 in vitro, e.g. in an ELISA or a Western blot. As with the article of manufacture, the kit comprises a container and a composition contained therein comprising an antibody of this invention. The kit may further comprise a label or package insert on or associated with the container. The kits may comprise additional components, e.g., diluents and buffers, substances which bind to the antibodies of this invention, e.g., a second antibody which may comprise a label such as those disclosed herein, e.g., a radiolabel, fluorescent label, or enzyme, or the kit may also comprise control antibodies. The additional components may be within separate containers within the kit. The label or package insert may provide a description of the composition as well as instructions for the intended in vitro or diagnostic use.

EXAMPLES

Example 1

Production and Isolation of Monoclonal Antibody Producing Hybridomas

The following MAb/hybridomas of the present invention are described below:
Ovr110.A7.1, Ovr110.A10.1, Ovr110.A13.1, Ovr110.A31.1, Ovr110.A57.1, Ovr110.A72.1 (previously identified as Ovr110 A22.1), Ovr110.A77.1, Ovr110.A87.1, Ovr110.A89, Ovr110.A 99.1, Ovr110.A102.1, Ovr110.A107, Ovr110.C1, Ovr110.C2, Ovr110.C3.2, Ovr110.C4, Ovr110.C5.1., Ovr110.C5.3, Ovr110.C6.3, Ovr110.C7.1, Ovr110.C8, Ovr110.C9.1, Ovr110.C10.1, Ovr110.C11.1, Ovr110.C12.1, Ovr110.C13, Ovr110.C14, Ovr110.C15, Ovr110.C16.1 and Ovr110.C17.1. If the MAb has been cloned, it will get the nomenclature "X.1," e.g., the first clone of A7 will be referred to as A7.1, the second clone of A7 will be referred to as A7.2, etc. For the purposes of this invention, a reference to A7 will include all clones, e.g., A7.1, A7.2, etc.

Immunogens and Antigens Recombinant Proteins, HA & His Tags & Transfected Cells)

Ovr110A Sequence & Protein Production

A full length DNA encoding the entire immature Ovr110 protein sequence from Met1 to Lys282 (SEQ ID NO:1) was inserted into a modified vector comprising a nucleotide sequence encoding a 17 amino acid secretion signal sequence from human stanniocalcin (STC) and a sequence encoding a 6 His tag, to generate a vector encoding a recombinant Ovr110 fusion protein having the secretion signal fused to the N-terminus and the 6 His-tag fused to the C-terminus of the Ovr110 protein. The resulting vector was used produce the recombinant protein using standard methods. Briefly, cells transformed with the resulting vectors were cultured under conditions suitable for production of the recombinant Ovr110 protein. The transformed cells were washed with Dulbecco's phosphate buffered saline (DPBS) and lysed in 5 volumes (5 ml/g cells) of 50 mM sodium phosphate, pH 8.0, containing 0.8 M sodium chloride, 0.3% Zwittergent 3-14 and 0.1% octyl phosphoglucoside by sonication. Insoluble material was isolated as a precipitate and the extraction was repeated twice. The isolated precipitate was dissolved in 50 mM sodium phosphate buffer, pH 7.8, containing 6 M guanidine hydrochloride (3 ml/g cells) and circulated through a 10-ml-Ni-NTA (Qiagen, Alameda, Calif.) column equilibrated with the same buffer on an Akta-100 system (Amersham Biosciences, Piscataway, N.J.) for about 40 column volumes (CV) at the flow rate of 5 ml/min. The column was then washed with 2 CV of the same phosphate-guanidine buffer, 2 CV of the 20 mM imidazole, 2 CV of 50 mM imidazole, and 4 CV of 100 mM imidazole in the above phosphate-guanidine buffer.

Ovr110A was eluted with 4 CV of 500 mM imidazole in phosphate-guanidine buffer and the column was further washed with 4 CV of 50 mM sodium phosphate, pH 7.6, containing 1 M imidazole and 6 M guanidine hydrochloride. Samples from collected fractions were subjected to SDS-PAGE and Western blot analysis for assessing the purity of Ovr110A. Purified fractions were pooled and dialyzed against PBS. Precipitates were collected and re-suspended in smaller volume of PBS by brief sonication.

```
Ovr110A Amino Acid Sequence (SEQ ID NO: 1)
         1          11         21         31         41         51
         |          |          |          |          |          |
    1  MLQNSAVLLV LVISASATMA SLGQILFWSI ISIIIILAGA IALIIGFGIS GRHSITVTTV   60

61  ASAGNIGEDG IQSCTFEPDI KLSDIVIQWL KEGVLGLVHE FKEGKDELSE QDEMFRGRTA  120

121  VFADQVIVGN ASLRLKNVQL TDAGTYKCYI ITSKGKGNAN LEYKTGAFSM PEVNVDYNAS  180

181  SETLRCEAPR WFPQPTVVWA SQVDQGANFS EVSNTSFELN SENVTMKVVS VLYNVTINNT  240

241  YSCMIENDIA KATGDIKVTE SEIKRRSHLQ LLNSKASLCV SSFFAISWAL LPLSPYLMLK  300

HHHHHH
```

Ovr110B Sequence & Protein Production

For immunization of mice, a recombinant protein fragment of Ovr110 was generated, which constituted only the predicted extracellular portion of the molecule, in order to select for monoclonal antibodies (MAb) that would bind to the exterior cell surface. A DNA fragment encoding the Ovr110 sequence from Gly30 (underlined in the sequence below) to Lys282 (plus a Met at the start codon position) of the immature protein, including the signal peptide, was inserted into a modified vector, which contained a nucleotide sequence encoding a 17 amino acid secretion signal sequence from human stanniocalcin (STC) and a nucleotide sequence encoding a 6 His tag such that the vector encoded a recombinant Ovr110 fusion protein having the 17 amino acid secretion signal sequence from human stanniocalcin (STC) fused to the N-terminus and the 6 His-tag fused to the C-terminus of the Ovr110 protein (Ovr110B). The resulting vector was used to transform DH10Bac bacteria for generation of the infection vector by transposition. Recombinant baculovirus were then generated by transfection of Sf9 cells with the transposed vector. Recombinant Ovr110B was expressed by infection of Hi5 cell line with the amplified and harvested virus particles.

Culture media from the recombinant Hi5 cells were harvested at 48 hr post-infection. The media were concentrated 10 fold and diafiltrated with 30 volumes of PBS, pH 7.9. The diafiltrated material was then incubated with 10 ml of Ni-NTA fast-flow gel (Qiagen) overnight at 4° C. in the presence of protease-inhibitor-cocktail. The gels were poured into a SK column and washed with 2 CV of 50 mM sodium phosphate, pH7.8, containing 0.5 M sodium chloride. Ovr110B was eluted by step-increasing of imidazole in the same phosphate-sodium chloride buffer (4 CV of 20 mM, 4 CV of 50 mM, 4 CV of 100 mM, 4 CV of 500 mM and 2 CV of 1000 mM). Samples from collected fractions were subjected to SDS-PAGE and Western blot analysis for assessing the purity of Ovr110B. Purified fractions were pooled and concentrated. Final products were dialyzed in PBS.

length Ovr110 cDNA (pDONR201_Ovr110) by producing a PCR fragment using following oligonucleotide primers:

```
                                           (SEQ ID NO: 3)
ATN496:
5'-CCA ATG CAT GGT ATT TCA GGG AGA CAC TCC (SEQ ID NO: 4)
ATN552:
5'-CG GCT AGC TTT TAG CAT CAG GTA AGG GCT G.
```

The PCR fragment was digested with NsiI and NheI, and cloned in-frame into a modified mammalian expression pCMV5His2 vector comprising a nucleotide sequence encoding a human stanniocalcin 1 (STC-1) secretion signal and nucleotide sequence encoding a ten histidine tag to produce the recombinant plasmid pCMV5jos2_Ovr110 which encoded a recombinant Ovr110 protein having the human stanniocalcin 1 (STC-1) secretion signal fused to the NH2 terminus and a ten histidine tag fused to the COOH terminus, respectively. DNA sequence analysis was performed using an ABI Prism Big Dye terminator cycle sequencing ready reaction kit from PE Applied Biosystems (Foster City, Calif.).

The recombinant plasmid, pCMV5His2_Ovr110, was used to transfect 293T cells in suspension culture (one liter serum free medium) in a spinner flask.

Culture medium was harvested at 48 hours post-transfection. Medium was concentrated 10-fold, and diafiltered with 100 mM sodium phosphate, 400 mM NaCl, 10% glycerol, pH 8.0. Concentrated medium containing Ovr110 was passed over a 5-mL nickel metal chelating column (Ni-NTA fast flow, Qiagen Inc.), which had been previously equilibrated with 100 mM sodium phosphate, 400 mM NaCl, 10% glycerol, pH 8.0. Column was then washed with 6 column volume (CV) of 100 mM sodium phosphate, 400 mM NaCl, 2 mM imidazole, 10% glycerol, pH 8.0. Ovr110 was eluted from the column using 22CV of 100 mM sodium phosphate, 400 mM

```
Ovr110B Amino Acid Sequence (SEQ ID NO: 2)
         1         11        21        31        41        51
         |         |         |         |         |         |
    1    MLQNSAVLLV LVISASATMG ISGRHSITVT TVASAGNIGE DGIQSCTFEP DIKLSDIVIQ

61    WLKEGVLGLV HEFKEGKDEL SEQDEMFRGR TAVFADQVIV GNASLRLKNV QLTDAGTYKC

121    YIITSKGKGN ANLEYKTGAF SMPEVNVDYN ASSETLRCEA PRWFPQPTVV WASQVDQGAN

181    FSEVSNTSFE LNSENVTMKV VSVLYNVTIN NTYSCMIEND IAKATGDIKV TESEIKRRSH

241    LQLLNSKASL CVSSFFAISW ALLPLSPYLM LKHHHHHH
```

Sequence & Protein Production for Mammalian Cell Expressed Ovr110:

A nucleic acid molecule encoding Ovr110 from Gly30 to Lys282 was generated from a shuttle vector containing a full NaCl, 10% glycerol, pH 8.0 containing 5 mM imidazole and 500 mM imidazole, respectively. Fractions containing Ovr110 were pooled and dialyzed in 100 mM sodium phosphate, 400 mM NaCl, 5% glycerol, pH 7.5.

```
Ovr110 with STC-1 secretion signal (Ovr110 sequence is
underlined) (SEQ ID NO: 5)
MLQNSAVLLVLVISASATHEAEQSRMHGISGRHSITVTTVASAGNIGEDGILSCTFEPDIKLS

DIVIQWLKEGVLGLVHEFKEGKDELSEQDEMFRGRTAVFADQVIVGNASLRLKNVQLTDAGTY

KCYIITSKGKGNANLEYKTGAFSMPEVNVDYNASSETLRCEAPRWFPQPTVVWASQVDQGANF

SEVSNTSFELNSENVTMKVVSVLYNVTINNTYSCMIENDIAKATGDIKVTESEIKRRSHLQLL

NSKASLCVSSFFAISWALLPLSPYLMLKASHHHHHHHHHH
```

BTLA Sequence & Protein Production:

A nucleic acid molecule encoding a full length human BTA (hBTLA), from Met1 to Ser289, was cloned by PCR from the pituitary gland and lymph node cDNA libraries using the following oligonucleotide primers:

```
                                              (SEQ ID NO: 6)
ATN551:
5'-CTT TGT TTA AAC ATG AAG ACA TTG CCT GCC ATG
``` vested medium, and medium was adjusted to pH 8.0. BTLA-containing medium was then passed over a 5-m/L recombinant protein A column, which had been previously equilibrated with 10 column volume (CV) of 50 mM borate, 4M NaCl, pH 8.0. Protein A column was then washed with 30 CV of 50 mM borate, 4M NaCl, pH8.0. BTLA5NT_mFc eluted from protein A column using 10 CV of 100 mM citrate, pH 3.0. Fractions containing BTLA5NT-mFc was neutralized with 1M Tris-HCl, pH 9.0, and dialyzed in 3 L PBS, pH 7.5.

```
BTLA sequence, full length (SEQ ID NO: 9)
MKTLPAMLGTGKLFWVFFLIPYLDIWNIHGKESCDVQLYIKRQSEHSILAGDPFELECPVKYCANRPHVTWC
KLNGTTCVKLEDRQTSWKEEKNISFFILHFEPVLPNDNGSYRCSANFQSNLIESHSTTLYVTDVKSASERPS
KDEMASRPWLLYSLLPLGGLPLLITTCFCLFCCLRRHQGKQNELSDTAGREINLVDAHLKSEQTEASTRQNS
QVLLSETGIYDNDPDLCFRMQEGSEVYSNPCLEENKPGIVYASLNHSVIGLNSRLARNVKEAPTEYASICVR
S BTLA, secreted form (SEQ ID NO: 10)
MKTLPAMLGTGKLFWVFFLIPYLDIWNIHGKESCDVQLYIKRQSEHSILAGDPFELECPVKYCANRPHVTWC
KLNGTTCVKLEDRQTSWKEEKNISFFILHFEPVLPNDNGSYRCSANFQSNLIESHSTTLYVTGKQNELSDTA
GREINLVDAHLKSEQTEASTRQNSQVLLSETGIYDNDPDLCFRMQEGSEVYSNPCLEENKPGIVYASLNHSV
IGLNSRLARNVKEAPTEYASICVRS BTLA5NT_mFc (BTLA sequenced is underlined) (SEQ ID NO: 11)
MKTLPAMLGTGKLFWVFFLIPYLDIWNIHGKESCDVQLYIKRQSEHSILAGDPFELECPVKYCANRPHVTWC
KLNGTTCVKLEDRQTSWKEEKNISFFILHFEPVLPNDNGSYRCSANFQSNLIESHSTTLYVTDVKSASERPS
KDEMASRPASENLYFQGPRGPTIKPCPPCKCPAPNLLGGPSVFIFPPKIKDVLMISLSPIVTCVVVDVSEDP
DVQISWFVNNVEVHTAQTQTHREDYNSTLRVVSALPIQHQDWMSGKEFKCKVNNKDLPAPIERTISKPKGVR
APQVYVLPPPEEEMTKKQVTLTCMVTDFMPEDIYVEWTNNGKTELNYKNTEPVLDSDGSYFMYSKLRVEKNW
VERNSYSCSVVHEGLHNHHTTKSFSRTPGK
```

-continued and

```
                                              (SEQ ID NO: 7)
ATN552:
5'-CG GCT AGC ACT CCT CAC ACA TAT GGA TGC.
```

A truncated hBTLA gene encoding Met1-Pro152, encompassing the surface immunoglobulin (Ig) domain, was cloned by PCR from a Burkitt's lymphoma cDNA library using the following oligonucleotide primers:

```
                                              SEQ ID NO: 6
ATN551: (see sequence above)
and
                                              (SEQ ID NO: 8)
ATN554:
5'-CG GCT AGC GGG TCT GCT TGC CAC TTC GTC.
```

A nucleic acid molecule encoding a full length secreted form, lacking the transmembrane domain, of hBTLA, from Met1-Ser241, was cloned by PCR from a lymph node cDNA library using oligonucleotide primers ATN551 and ATN552. The PCR fragments were digested with PmeI and NheI and ligated either into pCMV5HIS2 or pCMVSFc 1, which had been cut with the same enzymes, to generate protein constructs that had a C-terminal extension AS-HHHHHHHHHH or AS-mouse Fc domain (mFc), respectively. DNA sequence analysis was performed using an ABI Prism BigDye terminator cycle sequencing ready reaction kit from PE Applied Biosystems (Foster City, Calif.).

The recombinant plasmid, pCMV5Fc1_BTLA5NT, which encoded only the surface Ig domain of hBTLA fused to mFc (BTLA5NT_mFc), was used to transfect 293T cells in suspension culture (one liter serum free medium) in a spinner flask. Culture medium was harvested at 48 hours post-transfection. Sodium chloride was added to 3M final to the har- Ovr107 Sequence & Protein Production A recombinant Ovr107 protein was used to screen out poly reactive hybridoma clones. Ovr107 is upregulated widely in multiple cancers and the recombinant Ovr107 used herein contains a potentially cross reactive hexahistidine tag. Thus the recombinant Ovr107 is useful for identifying polyreactive antibodies.

A full length cDNA encoding the Ovr107 sequence from Met1 to Ile596 (WO 01/37864 Human Ovr107 ovarian cancer marker) was cloned by PCR and inserted into a vector. The Ovr107 coding region was then transferred by recombination into a vector comprising a nucleotide sequence encoding a 6 His tag such that a Ovr107 fusion protein having a 6 His-tag fused to its C-terminal was generated. The resulting vector was used to transform DH10Bac bacteria for generation of the infection vector by transposition. Recombinant baculovirus was then generated by transfection of Sf9 cells with the transposed vector. Recombinant Ovr107 was expressed by infection of Sf9 or Hi5 cell lines with the amplified and harvested recombinant baculovirus particles.

Recombinant baculovirus infected Hi5 cells were harvested 48 hr post-infection. The cells were washed with DPBS and lysed in (5 ml/g cells) 100 mM sodium phosphate, pH 8.0, containing 0.4 M sodium chloride, 10% glycerol, 1% Triton X-100 and 10 mM imidazole by sonication. The extract was incubated with 10 mg of DNase at room temperature for 30 minutes and then centrifuged in a SS-34 rotor at 17,000 rpm for 30 minutes. The supernatant was further filtered through a 45 mm filter and loaded onto a 5-ml-Ni-NTA column (Qiagen) equilibrated with 0.1 M sodium phosphate, pH 8.1, containing 0.4 M sodium chloride and 10% glycerol at the flow rate of 3 ml/min. The column was washed with 15 column volumes (CV) of the same equilibrating buffer and Ovr107 was eluted by step-increasing of imidazole in the phosphate-sodium chloride buffer (10 CV of 20 mM, 10 CV of 50 mM, 10 CV of 100 mM, 5 CV of 500 mM and 5 CV of 1000 mM). Fractions were collected in 5 ml/tube and samples from collected fractions were subjected to SDS-PAGE and Western analysis for assessing the purity of Ovr107. Purified fractions were pooled and concentrated. Final products were dialyzed in PBS.

expression vector, PCDNA3.1, and the recombinant vector was used to transfect human 293F cells (Invitrogen). Fifty ml of 293F cells cultured in freestyle medium (GIBCO) at $10^6$ cells/ml were transfected using 293fectin transfection reagent (Invitrogen), according to the manufacturer's guidelines.

```
Ovr107 Amino Acid Sequence with HA Tag (SEQ ID NO: 12)
MNRTWPRRIWGSSQDEAELIREDIQGALHNYRSGRGERRAAALRATQEELQRDRSPAAETPPLQRRPSVRAV

ISTVERGAGRGRPQAKPIPEAEEAQRPEPVGTSSNADSASPDLGPRGPDLVVLQAEREVDILNHVFDDVESF

VSRLQKSAEAARVLEHRERGRRSRRRAAGEGLLTLRAKPPSEAEYTDVLQKIKYAFSLLARLRGNIADPSSP

ELLHFLFGPLQMIVNTSGGPEFASSVRRPHLTSDAVALLRDNVTPRENELWTSLGDSWTRPGLELSPEEGPP

YRPEFFSGWBPPVTDPQSRAWEDPVEKQLQHERRRRQQSAPQVAVNGHRDLEPESEPQLESETAGKWVLCNY

DFQARNSSELSVKQRDVLEVLDDSRKWWKVRDPAGQEGYVPYNILTPYPGPRLHHSQSPARSLNSTPPPPPA

PAPAPPPALARPRWDRPRWDSCDSLNGLDPSEKEKFSQMLIVNEELQARLAQGRSGPSRAVPGPRAPEPQLS

PGSDASEVRAWLQAKGFSSGTVDALGVLTGAQLFSLQKEELRAVSPEEGARVYSQVTVQRSLLEDKEKVSEL

EAVMEKQKKKVEGEVEMEVIDPAFLYKVVRWAHHHHHH
```

Generation of Stable LMTK Mouse Cell Lines

A mammalian vector encoding a HA-tagged Ovr110 was transfected into mouse LMTK cells. Stable transfectants were selected in Dulbecco's modified Eagle's medium (DMEM)/10% FBS, with blastocidin at 10 ug/mL, for 7-10 days, followed by single cell sorting (Coulter Elite, Beckmann Coulter, Sunnyvale, Calif.) based on fluorescence, at 1 cell/well in 96 well plates. Transfected LMTK cells were grown cells in 96 well plates (VWR, Brisbane, Calif.), expanded into 24 well plates and subsequently into 6 well plates. After one week in culture, individual clones were assayed for expression of Ovr110 by Western blot using anti-HA antibody (Covance, Richmond, Calif.). Two LMTK cell clones expressing the highest level of Ovr110-HA were expanded into 75 cm² flasks (VWR) for screening of hybridomas, cryopreserved in fetal bovine serum (FBS) with 10% DMSO and stored in Liquid Nitrogen at −196° C. to assure maintenance of viable clone cultures.

DNA, cells and 293fectin were mixed in OPTI-MEM medium (GIBCO). Cells were used for analysis 48 h after transfection.

Immunization

For the A-series MAb fusion, mice were immunized with soluble Ovr110B recombinant protein, which corresponds to the extracellular domain of the native protein, in order to generate MAbs of both in-vivo therapeutic and diagnostic utility. For the C-series MAb fusion, mice were immunized with the mammalian expressed extracellular domain. Groups of 8 BALB/c mice were immunized intradermally in both rear footpads. All injections were 25 uL per foot. The first injection (day 1) of 10 ug of antigen per mouse was in Dulbecco's phosphate buffered saline (DPBS) mixed in equal volume to volume ratio with Titermax gold adjuvant (Sigma, Saint Louis, Miss.). Subsequent injections of 10 ug of antigen per mouse occurred on days 5, 9, 12, 16, 19, 23, 26, 29, 30 and

```
Ovr110-HA Amino Acid Sequence (SEQ ID NO: 13)
         1          11         21         31         41         51
         |          |          |          |          |          |
  1   MLQNSAVLLV LVISASATMA SLGQILFWSI ISIIIILAGA IALIIGFGIS GRHSITVTTV   60

61   ASAGNIGEDG IQSCTFEPDI KLSDIVIQWL KEGVLGLVHE FKEGKDELSE QDEMFRGRTA  120

121   VFADQVIVGN ASLRLKNVQL TDAGTYKCYI ITSKGKGNAN LEYKTGAFSM PEVNVDYNAS  180

181   SETLRCEAPR WFPQPTVVWA SQVDQGANFS EVSNTSFELN SENVTMKVVS VLYNVTINNT  240

241   YSCMIENDIA KATGDIKVTE SEIKRRSHLQ LLNSKASLCV SSFFAISWAL LPLSPYLMLK  300

YPYDVPDYA*
*HA tag sequence
```

Generation of Transient 293F Transfected Cells

A nucleic acid molecule encoding Ovr110 (SEQ ID NO: 13), without the HA tag was cloned into the mammalian consisted of antigen in 20 uL of DPBS plus 5 uL of Adju-phos adjuvant (Accurate Chemical & Scientific Corp., Westbury, N.Y.) per mouse. The final boost injection on day 33 consisted of antigen diluted in DPBS alone. Fusion occurred on Day 37.

Hybridoma Fusion

Mice were sacrificed at the completion of the immunization protocol and draining lymph node (popliteal) tissue was collected by sterile dissection. Lymph node cells were dispersed by pressing through a sterile sieve into DMEM and removing T-cells via anti-CD90 (Thy1.2) coated magnetic beads (Miltenyl Biotech, Baraisch-Gladbach, Germany).

These primary B-cell enriched lymph node cells were then immortalized by electro-cell fusion (BTX, San Diego, Calif.) with the continuous myeloma cell line P3x63Ag8.653 (Kearney, J. F. et al., J. Immunology 123: 1548-1550, 1979). Successfully fused cells were selected by culturing in standard Hypoxanthine, Azaserine (HA) (Sigma) containing selection medium (DMEM/10% FBS). These fusion cultures were immediately distributed, 10 million cells per plate, into wells of 96 well culture plates. Distributing the culture in 96 well culture plates, immediately following fusion, facilitated selection of a larger diversity of hybridoma clones producing single, specific antibodies. Supernatants from wells were screened by ELISA, for reactivity against Ovr110B, Ovr110A and no cross-reactivity with an irrelevant protein (Ovr107).

Monoclonal cultures, consisting of the genetically uniform progeny from single cells, were established after the screening procedure above, by sorting of single viable cells into wells of two 96 well plates, using flow cytometry (Coulter Elite). The resulting murine B-cell hybridoma cultures were expanded using standard tissue culture techniques. Selected hybridomas were cryopreserved in fetal bovine serum (FBS) with 10% DMSO and stored in Liquid Nitrogen at −196° C. to assure maintenance of viable clone cultures.

Screening & Selection of Antibody Producing Hybridomas

Hybridoma cell lines were selected for production of Ovr110 specific antibody by enzyme linked solid phase immunoassay (ELISA). Ovr110B or Ovr107 proteins were nonspecifically adsorbed to wells of 96 well polystyrene EIA plates (VWR). Fifty uL of Ovr110B protein or peptide-BSA conjugate at 0.91 mg/mL in (DPBS) were incubated overnight at 4° C. in wells of 96 well polystyrene EIA plates. Plates were washed twice with Tris buffered saline with 0.05% Tween 20, pH 7.4 (TBST). The plate wells were then emptied and nonspecific binding capacity was blocked by completely filling the wells with TBST/0.5% bovine serum albumin (TBST/BSA) and incubating for 30 minutes at room temperature (RT). The plate wells were then emptied, 50 uL of hybridoma culture medium samples was added to the wells and incubated for 1 hour at RT. The wells were then washed 3 times with (TBST). One hundred uL of alkaline phosphatase conjugated goat anti-mouse IgG (Fc) (Pierce Chemical Co., Rockford, Ill.), diluted 1:5000 in TBST/BSA, was then added to each well and incubated for 1 hour at RT. The wells were then washed 3 times with TBST. One hundred uL of alkaline phosphatase substrate para-nitrophenylphosphate (pNPP) (Sigma) at 1 mg/mL in 1 M Diethanolamine buffer pH 8.9 (Sigma) was then added to each well and incubated for 20 min. at RT. Bound alkaline phosphatase activity was indicated by the development of a visible yellow color. The enzymatic reaction was quantitated by measuring the solution's absorbance at 405 nm wavelength. Cultures producing the highest absorbance values are chosen for expansion and further evaluation.

ELISA Screening of Ovr110 MAbs

After 2 weeks culture, hybridomas with supernatants producing ELISA absorbance values greater than 1.0 with Ovr110B and less than 0.2 with Ovr107, were re-arrayed from twenty-five 96 well culture plates, into new 96 well culture plates and cultured for a further week.

After a further week of culture, 12 hybridomas from the A-series and 15 from the C-series, with supernatants producing ELISA absorbance values greater than 1.0 with Ovr110B (Tables 1A & 1B) and less than 0.2 with Ovr107, were selected for single cell cloning into 96 well culture plates, by cell sorting (Coulter Elite).

TABLE 1A

RESULTS OF TESTING SINGLE CELL CLONES OF Ovr110 A-SERIES MAbs

| Clone # | ELISA OD (405 nm) Original Well # | Original Well # | Plate Density | Outgrowth (# clones/ 96 well plate) | Plating Method | Mab Clone ELISA OD (405 nm) |
|---|---|---|---|---|---|---|
| A7.1 | 2.3172 | 1 | 1 cell/well | 3 | Sorter | 3.5388 |
| A7.2 | 2.1940 | 3 | 1 cell/well | | Sorter | 3.7160 |
| A10.1 | 1.5391 | 1 | 1 cell/well | 2 | Sorter | 3.1965 |
| A10.2 | 3.9733 | G10 | 1 cell/well | | Sorter | 2.2502 |
| A13.1 | 2.0736 | 2 | 1 cell/well | 18 | Sorter | 3.3627 |
| A13.2 | 2.0000 | 3 | 1 cell/well | | Sorter | 3.5381 |
| A31.1 | 2.7208 | 1 | 1 cell/well | 8 | Sorter | 3.6109 |
| A31.2 | 2.4506 | 2 | 1 cell/well | | Sorter | 3.0818 |
| A57.1 | 2.8313 | 1 | 1 cell/well | 27 | Sorter | 3.6099 |
| A57.2 | 2.7821 | 3 | 1 cell/well | | Sorter | 3.9733 |
| A72.1 | 2.6737 | 1 | 1 cell/well | 13 | Sorter | 3.6999 |
| A72.2 | 2.6059 | 5 | 1 cell/well | | Sorter | 4.0000 |
| A77.1 | 1.6650 | 1 | 1 cell/well | 2 | Sorter | 1.5370 |
| A77.2 | 1.8328 | 4 | 1 cell/well | 3 | Sorter | 1.6186 |
| A102.1 | 2.1280 | 2 | 1 cell/well | 4 | Sorter | 1.1054 |
| A102.2 | 1.4710 | 3 | 1 cell/well | | Sorter | 1.0121 |
| A87.1 | 2.1396 | 3 | 1 cell/well | 13 | Sorter | 1.8355 |
| A87.2 | 1.9965 | 4 | 1 cell/well | | Sorter | 1.9795 |
| A89.1 | 3.0326 | 7 | 1 cell/well | 16 | Sorter | 1.9081 |
| A89.2 | 3.0013 | 8 | 1 cell/well | | Sorter | 1.9666 |
| A99.1 | 3.2165 | 2 | 1 cell/well | 4 | Sorter | 1.8815 |
| A99.2 | 3.4925 | 4 | 1 cell/well | | Sorter | 2.0927 |

TABLE 1B

RESULTS OF TESTING SINGLE CELL CLONES OF Ovr110 C-SERIES MAbs

| Clone # | Plating Method | Plate Density | ELISA OD |
|---|---|---|---|
| C1 | sorter | 1 cell/well | No positives |
| C3.2 | sorter | 1 cell/well | 1.9884 |
| C4 | sorter | 1 cell/well | No positives |
| C5.3 | sorter | 5 cell/well | 2.0032 |
| C6.3 | sorter | 1 cell/well | 1.9797 |
| C7.1 | sorter | 1 cell/well | 0.0218 |
| C8 | sorter | 1 cell/well | No positives |
| C9.1 | sorter | 1 cell/well | 2.5158 |
| C10.1 | sorter | 1 cell/well | 2.1172 |
| C11.1 | sorter | 5 cell/well | 2.3633 |
| C12.1 | sorter | 5 cell/well | 2.5522 |
| C13 | sorter | 1 cell/well | No positives |
| C14 | sorter | 1 cell/well | No outgrowth |
| C16.1 | sorter | 1 cell/well | 2.0682 |
| C17.1 | sorter | 1 & 5 cell/well | 1.7183 |

Results from ELISA Screening of Cloned Ovr110 MAbs

After 2 weeks of culture, supernatants from 2 hybridoma clones from each parent hybridoma were tested for production of ELISA absorbance values greater than 1.5 with Ovr110B (Tables 1A and B) or Ovr110 peptides and less than 0.2 with Ovr107. Clones Ovr110.A7.1, Ovr110.A10.1, Ovr110.A13.1, Ovr110.A31.1, Ovr110.A57.1, Ovr110.A72.1, Ovr110.A77.1, Ovr110.A87.1, Ovr110.A89.1, Ovr110.A 99.1, Ovr110.A102.1, Ovr110.A107.1, Ovr110.C1, Ovr110.C2, Ovr110.C3.2, Ovr110.C4, Ovr110.C5.3, Ovr110.C6.3, Ovr110.C7.1, Ovr110.C8, Ovr110.C9.1, Ovr110.C10.1, Ovr110.C11.1, Ovr110.C12.1, Ovr110.C13, Ovr110.C14, Ovr110.C15, Ovr110.C16.1 & Ovr110.C17.1 were all selected for scale up for immunohistochemical, immunofluorescence and functional testing.

FACS Screening for Cell Surface Binding of Ovr110 MAbs

LMTX-Ovr110-HA stable transfectants and Ovr110 mRNA positive (SKBR3) and mRNA negative (HT29) tumor cell lines were grown in DMEM/10% FBS+P/S. One day prior to staining, the LMTK-Ovr110-HA stable transfected cells were stimulated by adding sodium butylate to a 5 mM final concentration. For FACS analysis, LMTK-Ovr110-HA cells or tumor cell lines were washed once with 10 ml $Ca^{+2}$/$Mg^{+2}$ free DPBS and then 7 ml of warm (37° C.) Cellstripper (Mediatech, Herndon, Va.) was added per 150 $cm^2$ flask. The cells were then incubated for 5 minutes at 37° C. with tapping of the flask to remove tightly attached cells. The cells were removed and pipetted several times to break aggregates, then immediately placed in DMEM/10% FBS/5 mM sodium butyrate. The cells were then centrifuged down for 5 minutes at 1300 rpm and resuspended in DMEM/10% FBS/5 mM sodium butyrate. The cells were incubated at 37° C. for a 30 min. recovery period. Prior to staining, viability of the cells was measured using Guava Viacount (Guava Cytometers, City, Calif.) and if >90% viable they were distributed into 96-well v-bottom plates (VWR) for staining with MAbs.

Cells were aliquoted at 0.5-1.0×10⁶ cells/well in 96-well v-bottom plates and centrifuged for 2 minutes at 1500 rpm. Supernatants were aspirated and plates briefly shaken on a vortex mixer to resuspend the cells, then 200 ul of DPBS/3% FBS/0.01% Na Azide (FACS buffer) was added to each well. Centrifugation and aspiration was repeated, then 25 uL of sequential dilutions of hybridoma supernatant or purified MAb was added to the cells. Plates were stored on ice for 15 min., then washed and centrifuged as above, in 200 uL of FACS buffer. This washing procedure was repeated a twice and then 25 uL of phycoerythrin (PE) conjugated donkey anti-mouse IgG Fc antibody (Jackson Immunoresearch Laboratories Inc., West Grove, Pa.) were added to cells. After 15 minutes on ice the cells were washed twice, as above and then resuspended in 250 uL of FACS buffer for analysis on the cell sorter or flow cytometer. In certain cases, for storage overnight at 4° C. prior to analysis, 133 ul of FACS buffer and 67 uL of 1% paraformaldehyde/DPBS was added to each well, for fixation, then the volume was increased to 250 uL with DPBS. Stained cells were analyzed on an Elite fluorescent activated cell sorter (FACS) (Beckman-Coulter, Miami, Fla.).

Results of a representative experiment demonstrating cell surface expression by FACS analysis are depicted in FIG. 1. Binding of the Ovr110 MAb A7.1, followed by binding of the donkey anti-mouse Ig-PE conjugate (DAMPE) resulted in 49% of Ovr110 transfected mouse LMTK cells being positive, with a fluorescence intensity (mean fluorescence intensity, MFI) 7.5-fold higher than cells stained with DAMPE alone. Further FACS analysis data with human tumor cell lines are presented in Table 2 below. As can be seen from the results, Ovr110.C3.2, Ovr110.C5.3 and Ovr110.C6.3 each bound to greater than 80% of the fresh Ovr110 mRNA positive SKBR3 cells, whereas the control negative MAb Pro104.D9.1 bound to less than 2% of these same breast cancer derived cells. Ovr110.C3.2, Ovr110.C5.3 and Ovr110.C6.3, similarly bound to less than 2% of the Ovr110 mRNA negative cells of the colon cancer cell line HT29.

TABLE 2

Ovr110 MAb BINDING TO VIABLE SKBR3 BREAST CANCER CELL LINE

| MAb Clone | SKBR3 | | HT29 | |
|---|---|---|---|---|
| | % Cells Positive | MFI | % Cells Positive | MFI |
| None | 3.2 | 0.35 | 1.4 | 0.316 |
| Ovr10.A57.1 | 9.8 | 0.82 | 1.2 | 0.385 |
| Pro104.D9.1 | 1.9 | 0.395 | 1.3 | 0.354 |
| Ovr110.C1 | 1.9 | 0.413 | | |
| Ovr110.C3 | 83.8 | 4.08 | 2 | 0.373 |
| Ovr110.C4 | 17.8 | 0.971 | 0.8 | 0.331 |
| Ovr110.C5 | 86.5 | 4.34 | 1.5 | 0.356 |
| Ovr110.C6 | 89.1 | 4.73 | 1.7 | 0.37 |
| Ovr110.C7 | 5.2 | 0.641 | | |
| Ovr110.C8 | 1.6 | 0.394 | | |
| Ovr110.C9 | 22.3 | 0.936 | 1.5 | 0.342 |
| Ovr110.C10 | 4.9 | 0.605 | | |
| Ovr110.C11 | 2.3 | 0.442 | | |
| Ovr110.C12 | 9.4 | 0.778 | 4.7 | 0.4 |
| Ovr110.C13 | 1.6 | 0.399 | | |
| Ovr110.C14 | 70.3 | 2.77 | 0.9 | 0.358 |
| Ovr110.C16 | 3.4 | 0.479 | | |
| Ovr110.C17 | 63.6 | 2.4 | 1.3 | 0.342 |

Ovr110 MAb Isotypes

The isotypes of the MAbs were determined using commercially available mouse monoclonal antibody isotyping immunoassay test kits (IsoStrip, Roche Diagnostic Corp., Indianapolis, Ind.). Results of the isotyping are listed in Table 3. All MAbs were of the $IgG_1$/κ isotype, except Ovr110 MAb A10.1, which was of the $IgG_{2b}$/κ isotype.

TABLE 3

Ovr110 MAb ISOTYPES

| Clone | Isotype |
|---|---|
| A7.1 | IgG1: Kappa |
| A10.1 | IgG2$_b$: Kappa |
| A13.1 | IgG1: Kappa |
| A31.1 | IgG1: Kappa |
| A57.1 | IgG1: Kappa |
| A72.1 | IgG1: Kappa |
| A77.1 | IgG1: Kappa |
| A87.1 | IgG1: Kappa |
| A89.1 | IgG1: Kappa |
| A99.1 | IgG1: Kappa |
| A102.1 | IgG1: Kappa |
| A107.1 | IgG1: Kappa |
| C3.2 | IgG1: Kappa |
| C5.3 | IgG1: Kappa |
| C6.3 | IgG1: Kappa |
| C7.1 | IgG1: Kappa |
| C11.1 | IgG1: Kappa |
| C12.1 | IgG1: Kappa |
| C17.1 | IgG1: Kappa |

Ovr110 MAb Affinity Analysis

Binding kinetics and affinity constants were calculated from surface plasmon resonance measurements using a BIACORE 3000 instrument (Biacore, Piscataway, N.J.). Experiments were designed to simultaneously generate on rate, off rate, and affinity values for the Ovr110 MAbs.

Rabbit anti-mouse IgG Fc antibody (Biacore) was immobilized on flow cells 2, 3, and 4 of a CM5 sensor chip (Biacore) by standard amine coupling (Biacore). Flow cell one was used as a blank surface for reference subtractions, and was activated and then inactivated with ethanolamine. Ovr110 MAbs were captured on the rabbit anti-mouse-IgG Fc coated chip, followed by binding of the antigen. Therefore these measurements should represent real 1:1 affinities and not avidity effects that are observed with direct antigen immobilizations, due to the divalent nature of IgG antibodies. MAbs were diluted in HBS EP buffer (Biacore) to 15 ug/mL and were divided into multiple tubes to minimize evaporation between cycles. The MAbs were passed through the flow cells for 2 minutes at 20 uL/minute. The MAb capture level ranged between 200 and 300 response units (RU) per flow cell. Following MAb capture the surface was allowed to stabilize for 3 minutes. Ovr110B (1.56 mg/mL) antigen was then flowed over the captured MAbs at 20 uL/minute in flow cells and through the blank flow cell, for 4 minutes, at successive concentrations of 144, 72, 36, 18, 9, 4.5 ug/mL. Since the Ovr110B molecular weight is 35 kD these antigen concentrations correspond to 4.11, 2.06, 1.03, 0.514, 0.257, 0.129 uM. Two replicate cycles were performed for each antigen concentration or buffer. A dissociation time of 420 seconds was allowed between cycles and regeneration of the chip surfaces to anti-mouse IgG Fc antibody or blank surface, were performed by flowing 100 mM Glycine pH 1.75 through the flow cells for 30 seconds at 100 uL/minute.

The resulting data were analyzed by BiaEvaluation software (Biacore) using a global fit simultaneous ka/kd assuming Langmuir binding. The Rmax parameter of the software was set to local to allow compensation for minor variations in the anti-mouse IgG Fc capture step. The calculated affinities presented in Table 4, which are in the $10^{-9}$ to $10^{-13}$ M range, are sufficiently high to achieve a therapeutic dose in-vivo at less than or equal to 10 mg/kg.

TABLE 4

Ovr110 MAb AFFINITIES

| MAb | Affinity KD (M) | KA (MS) | kd (1/s) | ka (1/Ms) |
|---|---|---|---|---|
| A72.1 | 1.68E−09 | 8.17E+08 | 1.35E−05 | 1.36E+04 |
| A57.1 | 1.95E−09 | 5.5E+08 | 1.61E−05 | 8.86E+03 |
| A7.1 | 9.51E−13 | 1.14E+12 | 8.00E−09 | 9.12E+03 |

Western Blots

Protein extracts for western blot analysis were prepared in cell lysis buffer (1% NP-40, 10 mM Sodium Phosphate pH 7.2, 150 mM Sodium Chloride) from Ovr110-293T transfectants and mammalian adenocarcinoma cell lines. Proteins were separated by electrophoresis on NuPAGE 4-12% Bis-Tris gels (Invitrogen Life Technologies, Carlsbad, Calif.) under denaturing conditions in Novex-XCell II Minicell gel apparatus (Invitrogen, Life Tech) and subsequently transferred to PVDF membranes using an XCell II Blot Module (Invitrogen Life Technologies). Following the transfer of proteins, the membranes were blocked in 1% blocking reagent (Roche Diagnostic Corp., Indianapolis, Ind.) and incubated overnight at 4° C. with purified primary antibodies (Ovr110 monoclonal antibodies: A10.2, A13.1, A31.1, A57.1, A72.1, A77.1, A89, A107, C3.2, C5.1, C5.3, C6.3, C7.1, C9.1, C11.1, C12.1 or C17.1) and then with horseradish-peroxidase conjugated goat anti-mouse IgG secondary antibody (Jackson Immunoresearch Laboratories, Inc.) and finally visualized by chemiluminescence using an ECL advance western blotting detection kit (Amersham BioSciences, Piscataway, N.J.).

Deglycosylation experiments were performed on protein extracts from Ovr110-293T transfectants, Ovr110 mRNA positive (QPCR+) and Ovr110 mRNA negative (QPCR−) mammalian adenocarcinoma cell lines and ovarian tumors using Peptide N-Glycosidase F (New England Biolabs, Inc., Beverly, Mass.) as per the directions provided by the manufacturer. The deglycosylated samples were then analyzed by western blots as described above. Briefly, 100 ug of protein extract was denatured in Glycoprotein denaturing buffer (0.5% SDS+reducing agent) at 100° C. for 10 min. This was followed by the addition of kit reaction buffers at a final concentration of 1% NP-40 and 50 mM sodium phosphate before the addition of 100 units of PNGase F and incubated at 37° C. for 4 hours.

TABLE 5A

RESULTS FROM WESTERN BLOTS USING OVR110 MABS WITH EXTRACTS FROM TRANSFECTED 293T CELLS & BREAST, OVARIAN & COLON CANCER CELL LINES

| | A10.1 | A13.1 | A72.1 | A31.1 | A57.1 | A77.1 | A89 | A107 |
|---|---|---|---|---|---|---|---|---|
| Ovr110-HA-293T | + multiple bands major band at 49-60 kDa & minor band at ~30 kDa | + multiple bands major band at 49-60 kDa & minor band at ~30 kDa | + multiple bands major band at 49-60 kDa & minor band at ~30 kDa | + multiple bands major band at 49-60 kDa & minor band at ~30 kDa | + multiple bands major band at 49-60 kDa & minor band at ~30 kDa | + multiple bands major band at 49-60 kDa & minor band at ~30 kDa | + multiple bands major band at 49-60 kDa & minor band at ~30 kDa | + multiple bands major band at 49-60 kDa & minor band at ~30 kDa |
| Deglycosylated Ovr110-HA-293T | | | | | Major band at ~30 kDa minor band at ~16 kDa | | | |
| MCF7 & SKBR3 (QPCR+) | Weak 50-60 kDa | ++ 50-60 kDa | ++++ 50-60 kDa | +++ 50-60 kDa | ++++ 50-60 kDa | Weak 50-60 kDa | ++ 50-60 kDa | + 50-60 kDa |
| Deglycosylated MCF7 & SKBR3 (QPCR+) | | | | | ~30 kDa | | | |
| CaOV3 & HT29 (QPCR−) | − | − | − | − | − | − | − | − |

Results of the western blot experiments are summarized in Tables 5A & 5B. As can be observed, the Ovr110 MAbs A10.1, A13.1, A31.1, A57.1, A72.1, A77.1, A89, A107, C3.2, C5.1, C5.3, C6.3, C7.1, C9.1, C11.1, C12.1 and C17.1 identified minor bands of the predicted size for the non-glycosylated Ovr110 protein (30 kDa) and major bands at 49-60 kDa, in lysates of Ovr110 transfected human 293T cells. The larger bands were consistent with the presence of several glycosylation sites on the Ovr110 protein. Major bands of 50-60 kDa were also detected by the same Ovr110 MAbs, in lysates from the QPCR+ human breast cancer cell lines SKBR3 and MCF7 (ATCC, Manassas, Va.), but were not detected in lysates from the QPCR− cell lines CaOV3 and HT29 (ATCC). Deglycosylation with PNGase reduced the size of the bands detected by Ovr110 MAb A57.1 from ~60 kDa (glycosylated) to ~30 kDa (predicted non-glycosylated size), in lysates from Ovr110 transfected human 293T cells, and in lysates from SKBR3 and MCF7 (ATCC) breast cancer cell lines. Deglycosylation of lysates from 3 ovarian tumor samples, with PNGase F, also reduced the size of the bands detected by Ovr110 MAb 57.1 from ~60 kDa (glycosylated) to ~30 kDa.

Fluorescence Microscope Axiophot equipped with the appropriate fluorescent filters. Micrographs were obtained with a CCD camera.

Results

Of the eleven MAbs tested (Ovr110.A7.1, Ovr110.A13.1, Ovr110.A72.1, Ovr110.A31.1, Ovr110.A57.1, Ovr110.A77.1, Ovr110.A87.1, Ovr110.A89.1, Ovr110.A99.1, Ovr110.A102.1 and Ovr110.A107.1), ten antibodies were able to bind at least a portion of Ovr110 expressing cells. FIG. 2 shows the binding of Ovr110.A57.1 to the cell membrane of OvCAR-3 ovarian cancer cells (arrows in A) and SKBR-3 breast cancer cells (arrows in B). The cell membrane of CaOV-3 cells, a control cell line that does not express Ovr110, was not labeled when the cells were incubated with the same antibody (FIG. 2C).

Binding and Internalization in Live Cancer Cells

This study was performed using fluorescent antibodies. By labeling antibodies with the fluorescent dye Cy3, antibody binding and internalization can be visualized by fluorescence

TABLE 5B

RESULTS FROM WESTERN BLOTS USING OVR110 MABS WITH EXTRACTS FROM BREAST & COLON CANCER CELL LINES

| | C3.2 | C5.1 | C5.3 | C6.3 | C7.1 | C9.1 | C11.1 | C12.1 | C17.1 | A57.1 |
|---|---|---|---|---|---|---|---|---|---|---|
| SKBR3 (QPCR+) | + 50 kDa & weak 30 & 60 kDa | + 50 kDa & weak 30 & 60 kDa | + 50 kDa & weak bands at 30 & 60 kDa | + 50 & 62 kDa & weak band at 30 kDa | + 50 kDa & weak bands at 30 & 60 kDa | ++ 50 kDa & weak bands at 30 & 60 kDa | ++ 50 kDa & weak bands at 30 & 60 kDa | ++ 50 kDa & weak bands at 30 & 60 kDa | + 50 kDa & weak bands at 30 & 60 kDa | ++ 50-60 kDa & minor band at ~30 kDa |
| HT29 (QPCR−) | − | − | − | − | − | − | − | − | − | − |

Example 2

Cell Surface Binding of Ovr110 MAbs in Live Cancer Cells Demonstrated by Immunofluorescence The following cancer cell lines were used in this study: Ovarian OvCar-3, ovarian CaOV-3 and breast SKBr-3. OvCAR-3 and SKBR-3 cells but not the control CaOV-3 cells express Ovr110.

Cells were seeded on 18 mm glass coverslips and cultured at 37° C. in DMEM containing 10% fetal bovine serum and penicillin and streptomycin for 48 hr prior to treatment with the anti-Ovr110 MAbs.

Eleven Ovr110 MAbs (Ovr110.A7.1, Ovr110.A13.1, Ovr110.A72.1, Ovr110.A31.1, Ovr110.A57.1, Ovr110.A77.1, Ovr110.A87.1, Ovr110.A89.1, Ovr110.A99.1, Ovr110.A102.1 and Ovr110.A107.1) were tested to determine which antibody binds to the cell surface of Ovr110 expressing cancer cells. Primary MAbs were added to the medium at a final concentration of 10 ug/ml and incubated for one hour at 37° C. Following fixation with 3% formaldehyde in Phosphate Buffered Saline (PBS), the cells were incubated with a secondary Cy3-labeled donkey anti-mouse (Jackson Immunoresearch Laboratories, West Grove, Pa.) at a concentration of 10 ug/ml for 30 min. Following washing, the cells were mounted in a medium containing DAPI (Vectastain, Vector, Burlingame, Calif.) to visualize the cell nuclei and provide a counterstain, and observed in a Zeiss microscopy. The technology is well established. OvCAR-3 cells that do not express Ovr110 were used as negative controls.

Cy3 Conjugation

Ovr110.A7.1, Ovr110.A13.1, Ovr110.A72.1, Ovr110.A57.1, and Ovr110.A87.1 were labeled with Cy-3. Cy3 conjugation was carried out according to standard procedures and the manufacturer's guidelines. Briefly, 1 mg of antibody was dialyzed against 0.1M bicarbonate buffer (pH 9.3) for 60 min, mixed with Cy3 dye and incubated at RT for 2 hr, and then transferred in a Pierce Slide-A Lyzer Dialysis cassette for dialysis in 2 liters of PBS for 6 hr at 4 C. The operation was repeated 6 times. The Cy3 conjugated antibodies were recovered and concentration was measured in a spectrometer at 280 nm.

Ovr110.A7.1, Ovr110.A13.1, Ovr110.A72.1, Ovr110.A57.1 and Ovr110.A87.1 MAbs were then incubated at a concentration of 10 ug/ml with the cells at 37° C. in a water chamber for 60 min, washed in PBS and fix with 3% formaldehyde in PBS for 10 min. Following fixation, the coverslips with the cells were mounted in a medium containing DAPI (Vectastain) to visualize cell nuclei, and observed in a Zeiss fluorescence Microscope Axiophot equipped with the appropriate fluorescent filters. Micrographs were obtained with a color CCD camera.

Results

Figure 3:
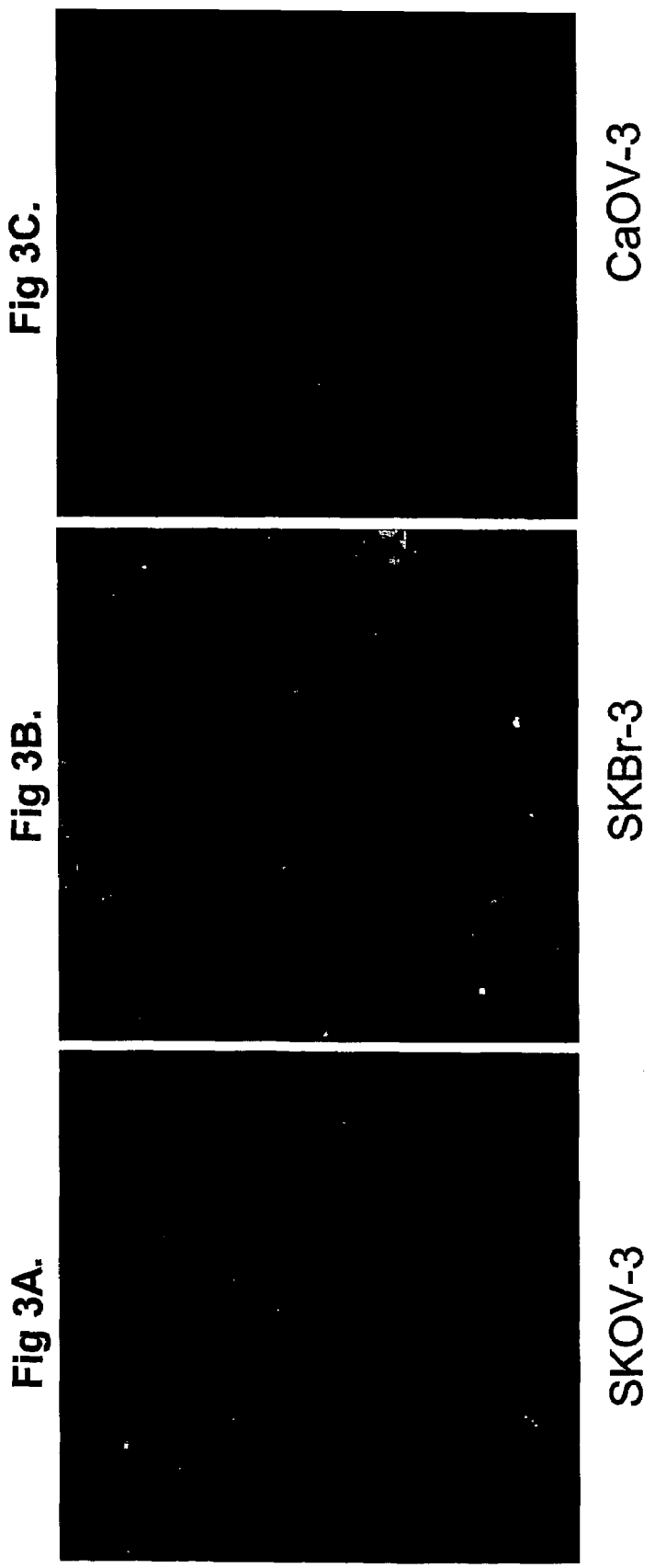
Figure 7A:
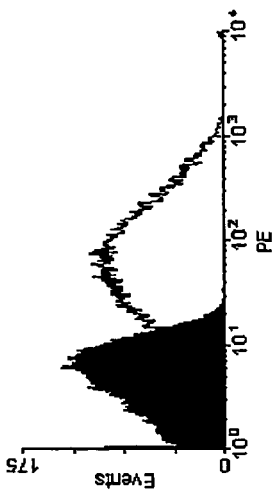
Figure 7B:
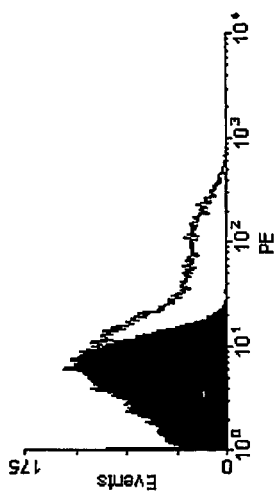
Figure 7C:
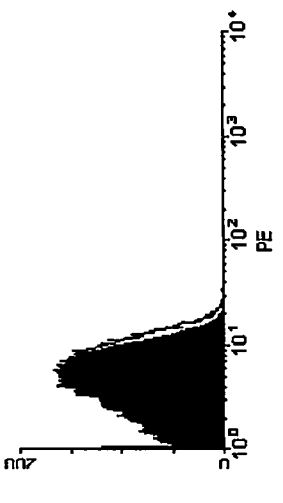
Figure 7D:
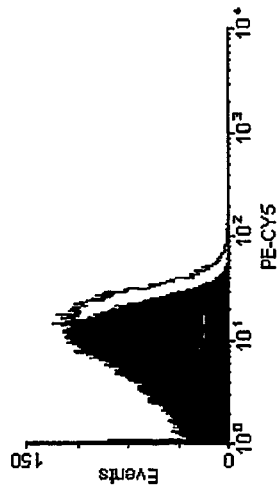
Figure 7E:
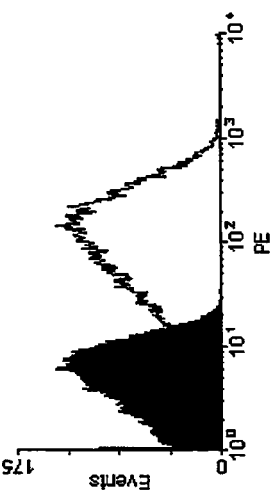
Figure 7F:
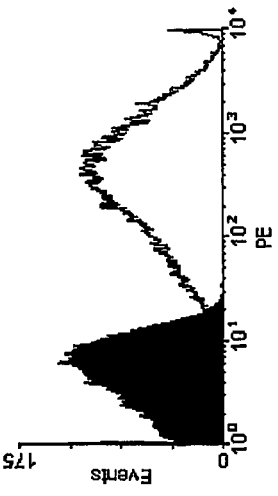
Figure 9:
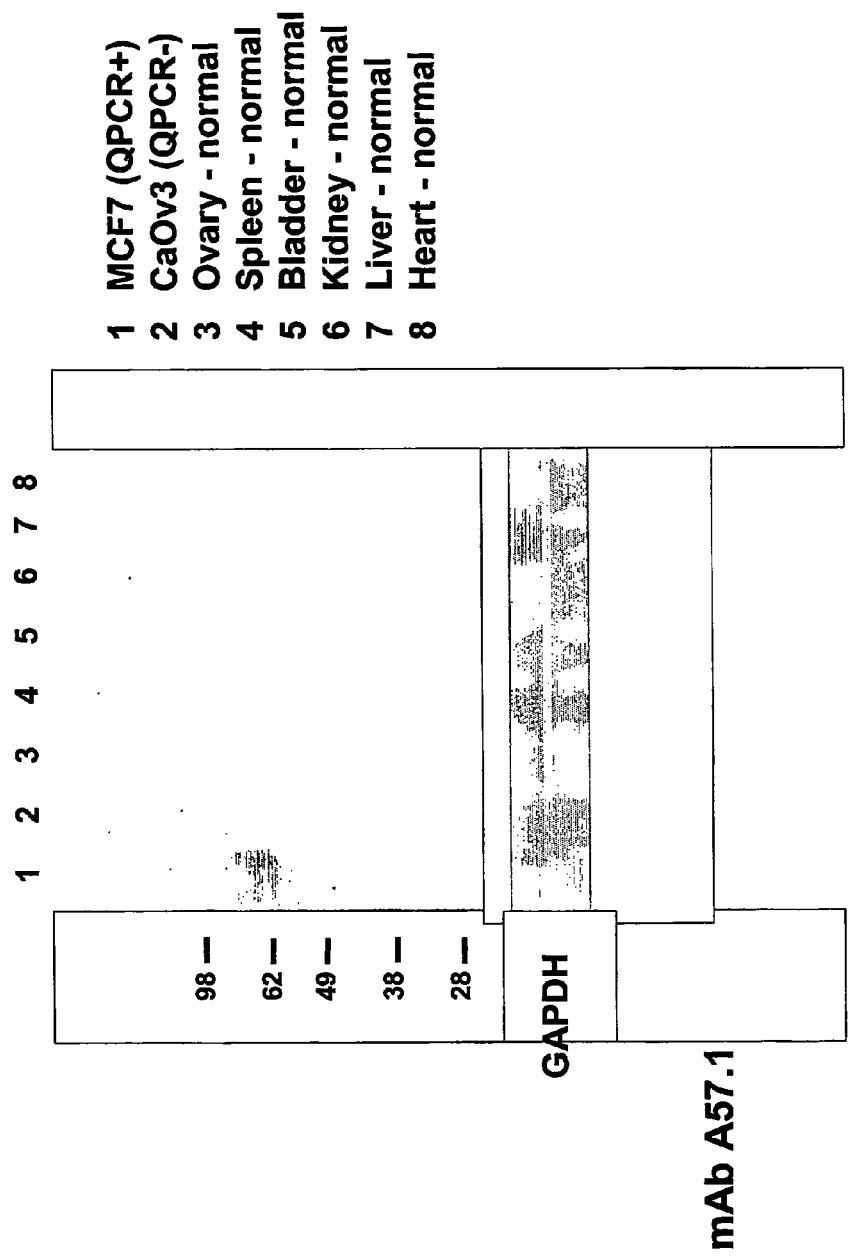
FIG. 9 shows Ovr110 protein is not detected in extracts of major organs.
Figure 10B:
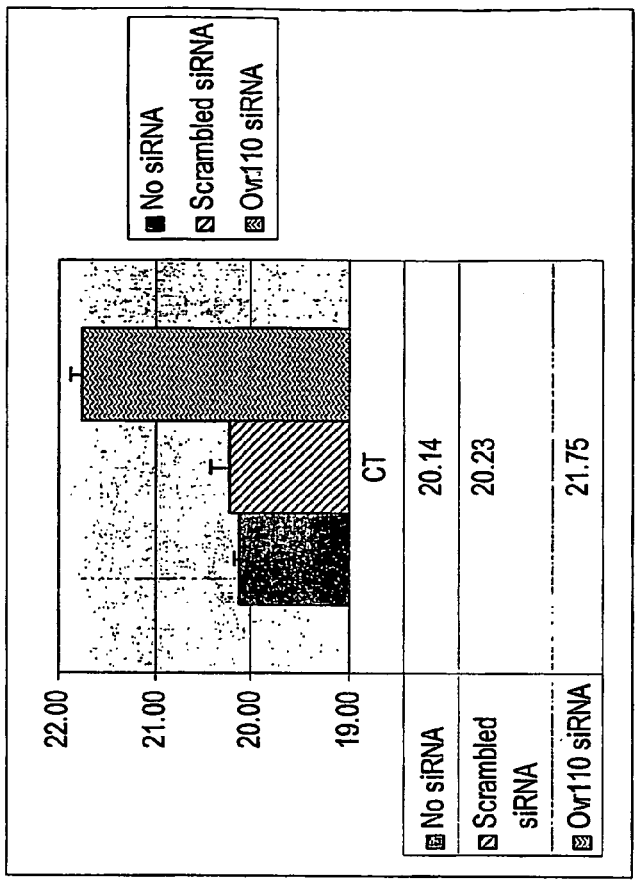
FIGS. 10A and 10B show specific knockdown of Ovr110 mRNA in SKBR3 breast cancer cells.
Figure 10A:
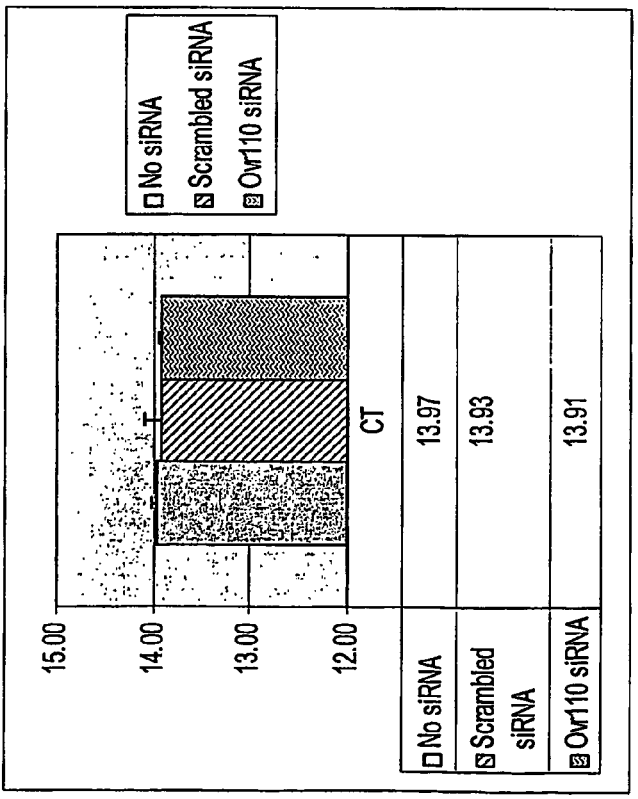

Immunofluorescence microscopy of cancer cells treated with Cy3-Ovr110.A7.1, Ovr110.A13.1, Ovr110.A72.1, Ovr110.A57.1, and Ovr110.A87.1 indicated that the cancer cells expressing Ovr110 bind and internalize the fluorescent antibodies to varying extent FIG. 3 A (arrows) shows that following binding Cy3-Ovr110.A57.1 is internalized by SKOV-3 cells and to a lesser degree by SKBr-3 cells (FIG. 3B). No or low binding of Cy3-Ovr110.A57.1 was observed in the CaOV-3 control cells (FIG. 3C). The internalization pattern staining in the SKOV-3 cells was characterized by the presence of perinuclear vesicles likely to correspond to endosomes located in the proximity of the Golgi apparatus (FIGS. 3A and B).

Conclusions

Ovr110 MAbs are internalized in vitro upon binding to Ovr110 on the cell surface of Ovr110 expressing cancer cells.

Ovr110 Distribution in Tumors and Normal Tissues Assessed by Immunohistochemistry Tissues Formalin fixed paraffin embedded blocks of breast, ovarian cancer and normal adjacent tissues were obtained from National Disease Research Interchange (Philadelphia, Pa.). OCT embedded blocks of normal organs were obtained from Zoion (Hawthorne, N.Y.).

Immunohistochemical Staining for Formalin Fixed Paraffin Embedded Sections

Six-μm-thick sections cut from formalin fixed paraffin embedded blocks were baked at 45° C., deparaffinized in Histoclear and rehydrated through a series of ethanol until PBS. Antigen retrieval was performed by boiling the section slides in 10 mM sodium citrate buffer (pH 6.0) at 120° C., 15~17 PSI in decloaking chamber (Biocare, Walnut Creek, Calif.) for 10 min. Endogenous peroxidase activity was quenched by treating with 3% hydrogen peroxide solution for 15 min. Slides were incubated with 1% BSA to block non-specific antibody binding and then reacted with 6 different primary Ovr110 MAbs used at a concentration of 1 ug/ml for 1 hour in room temperature in a DAKO autostainer (Dako Co., Carpinteria, Calif.). After washing in Tris-Buffered Saline (TBS) with 0.5% Tween −20, slides were incubated with anti-mouse IgG as the secondary antibody conjugated to horse radish peroxidase (HRP). After washing in TBS with 0.5% Tween −20, sections were visualized by 3,3'-diaminobenzidine chromogen for 2~5 minutes (Immunovision Technologies, Co. Daly City, Calif.) and counterstained with hematoxylin before mounting in Permount medium after dehydration. Normal mouse IgG at the same concentration as the primary antibody served as negative controls.

Immunohistochemical Staining for OCT Embedded Frozen Unfixed Sections

Slides were cut in the cryochamber at 5-8 um at an appropriate temperature, air dried for a minimum of ½ hour at room temperature. IHC was performed using the Immunovision Powervision Kit (Immunovision Technologies Co. Daly City, Calif.). Briefly, slides were rinsed in TBS to remove off OCT and incubated with the primary antibody Ovr110.A13.1 and Ovr110.A57.1 for 1 hour at room temperature. They were then post-fixed in 4% paraformaldehyde fixative for 10 minutes and treated as described above.

Results

Ovr110.A7.1, Ovr110.A10.1, Ovr110.A13.1, Ovr110.A57.1 and Ovr110.A87.1 were used to immunolabel sections of clinical samples of ovarian serous adenocarcinoma. FIG. 4 shows the distribution of Ovr110 in ovarian tumors as evaluated by IHC using Ovr110.A57.1.

Thirteen out of fifteen clinical samples (87%) showed positive immunolabeling using Ovr110.A57.1. while fourteen out of fifteen (93%) were positive using Ovr110.A13.1 (Table 6A). Specific immunostaining was restricted to the epithelial cells in the tumors and the number of positive cells varied between 50% to almost all of the tumor cells. FIG. 4A and FIG. 4B show that the epithelial cells of the tumor displayed a strong membranous staining (arrows) with less intense cytoplasmic staining and no background staining in the stroma. FIG. 4C shows lack of specific labeling in a control experiment in which the primary antibody was replaced with a mouse IgG fraction.

Eight out of ten (80%) breast cancer clinical samples were positive when Ovr110.A57.1 was used while five out of ten (50%) were positive using Ovr110.A13.1 (Table 6A). FIG. 5 shows the pattern of expression in clinical samples of breast infiltratrating ductal carcinoma. The labeling was restricted to the cell surface of the epithelial cells of the tumors (FIGS. 5A and B, arrows). FIG. 5C shows the absence of specific labeling in a control experiment in which the primary antibody was replaced with a mouse IgG fraction. As judged by the intensity of the immunolabeling, the level of expression for Ovr110 in the neoplastic ovarian and breast tissues was high. A limited number of pancreatic cancer samples were investigated for Ovr110 expression. Two out of four clinical samples (50%) showed expression of Ovr110 with Ovr110.A57.1 and three out of five with Ovr110.A13.1 (Table 6A). FIGS. 6 A and B shows the immunolabeling pattern obtained using Ovr110.A57.1 in clinical samples of pancreatic adenocarcinoma. The labeling is restricted to the cell surface of epithelial cells (arrows). No specific labeling was observed when normal mouse IgG was used instead of Ovr110.A57.1. Lung cancer tissues were also found to be positive for immunolabeling with A7.1, A13.1 and A31.1 (2/2, 2/3 & 1/2 cases respectively).

Ovr110 expression was also analyzed in normal tissues and generally found to be negative in the following organs: liver, stomach, bladder, testis, colon, ovary, prostate and lung (1/7 positive only with A13.1). The cells of the normal heart showed moderate cytoplasmic but no cell surface staining. The kidney showed moderate membranous staining of some distal convoluted tubules and the ascending loop. The apical membrane of the normal breast and pancreatic ducts was also labeled.

TABLE 6A

Summary of immunohistochemistry results showing the number of positive cases in normal human tissue samples and ovarian, breast and pancreatic cancer clinical samples.

| MAb | O C | O N | B C | B NAT* | B N | P C | P N | L C | L N |
|---|---|---|---|---|---|---|---|---|---|
| A7.1 | 12/15 | 0/3 | 2/2 | NA | 2/5 | 2/2 | 2/3 | 2/2 | 0/5 |
| A13.1 | 14/15 | 0/3 | 5/10 | 2/2 | 3/8 | 3/5 | 0/3 | 2/3 | 1/7 |
| A31.1 | 1/2 | 0/2 | 1/2 | NA | 1/5 | 0/2 | 0/3 | 1/2 | 0/5 |
| A57.1 | 13/15 | 0/3 | 8/10 | 2/2 | 2/3 | 2/4 | NA | NA | NA |

*NAT = Normal adjacent tissue
O C = ovarian cancer;
O N = ovary normal;
B C = breast cancer;
B NAT = breast NAT;
B N = breast normal;
P C = pancreatric cancer;
P N = pancreatic normal;
L C = lung cancer;
L N = lung normal

TABLE 6B

Binding of Ovr110 MAbs to normal adult mouse mammary tissue

|  | Conc. | Mammary gland | | | Lymph node in the Pad Lymphocytes |
|---|---|---|---|---|---|
|  |  | Ductal Epithelium | Stroma | Smooth Muscle |  |
| MAb |  |  |  |  |  |
| A57.1 | 1 ug/ml | 3+ C/M* | — | — | Lymphatic vessel 2+ C |
| C3.2 | 1 ug/ml | 3+ C | — | — | Some 1+ C |
| C6.3 | 1 ug/ml | 3+ C | — | — | 2+ C |
| C12.1 | 1 ug/ml | 3+ apical M | — | — | — |
| Controls |  |  |  |  |  |
| Pro104 D133.1 | 2 ug/ml | — | — | — | — |
| E-cadherin | 0.25 ug/ml | 3+ M | — | — | — |
| IgG1 | 10 ug/ml | — | — | — | — |

*Grading 1-3+ using Carr's scale, C = cytoplasmic & M = membrane

Because binding to the rodent homolog of Ovr110 would facilitate preclinical safety testing for the binding of the anti-Ovr110 MAbs, several anti-Ovr110 Mabs was tested in normal mouse mammary tissue that was prepared, sectioned and stained in the same manner as the normal human tissues. Results of this testing are presented in Table 6B. Ovr110.A57.1, Ovr110.C3.2, Ovr110.C6.3 and Ovr110.C12.1 all reacted with the ductal epithelial cells in mouse mammary glands, in a similar pattern to that in normal human mammary tissues.

Summary

The results demonstrate that Ovr110 expression can be used as a highly sensitive and specific indicator for serous carcinomas of the ovary and breast infiltrating ductal carcinoma, even though, Ovr110 was also expressed in some pancreatic and lung cancers and several anti-Ovr110 MAbs apparently also reacted with a related molecule in mouse mammary tissue. The cell membrane staining pattern indicates that Ovr110 should be an ideal therapeutic target.

Example 3

Killing of Ovr110 Transfected CHO Cells by Incubation with MAbs and Anti-Mouse MAb Saporin Conjugate Experiments were performed by incubating Ovr110 transfected CHO cells (Ovr110-CHO) with Ovr110 Mabs premixed with Mab-zap goat anti-mouse Ig saporin conjugate (Advanced Targeting Systems, San Diego, Calif.) and measuring cell viability at 72 and 96 h, to detect potential killing effects on these Ovr110 expressing cells. On day 1, Ovr110-CHO cells were placed into 96 well, flat bottom, sterile cell culture plates (Corning), in triplicate wells, at 2000 cells/75 uL/well, in F12 medium with 10% FBS, P/S. Plates were incubated at 37° C., in 5% CO2, overnight. Duplicate plates were set up to allow readings at 72 h and 96 h. On Day 2 (0 h), 25 uL of 4× final MAb concentrations alone, or 25 uL of 4×MAb premixed with 25 uL of 4×Mab Zap, or 25 uL of 4×Mab Zap alone, or 25 uL of medium alone were added to wells of the 96 well plates, in triplicate, to a final volume of 100 uL. Final MAb concentrations were 2 ug/mL, 0.4 ug/mL, 0.08 ug/mL and 0 ug/mL and the final concentration of MAb Zap was 1 ug/mL. Triplicate wells with medium alone, MAb alone (2 ug/mL only) and MAb Zap alone were used as negative controls. The anti-transferrin receptor MAb 5E9 (ATCC, Manassus, Va.) was used as a positive control MAb for killing. Plates were shaken gently for five minutes to mix the reagents and then incubated at 37° C., in 5% CO2. On day 5 (72 h), 10 uL of a of Alamar Blue stock solution (Biosource International, Camarillo, Calif.) was added to wells of the first set of plates and they were incubated at 37° C., in 5% CO2 for 2-7 h. Plates were then analyzed on a SpectraMAx GeminiEM spectraphotometer (Molecular Devices, Sunnyvale, Calif.) (emission=590 nm, excitation=560 nm and Autocutoff=570 nm) and viability was expressed as a percentage the control wells with medium alone.

TABLE 7

Ovr110-CHO killing by Ovr110 MAb & MAb Zap Saporin Conjugate

| | % | Percent Growth Compared to Wells with Medium Alone | | | | | |
|---|---|---|---|---|---|---|---|
| | Ovr110-CHO Positive with | Ovr110-CHO MAb (2 ug/mL) + | | | MAb + MAb Zap | | |
| MAb Clone | MAb (IF)* | MAb Zap | MAb Zap | Mab (2 ug/mL) | MAb (0.08 ug/mL) | MAb (0.4 ug/mL) | MAb (2 ug/mL) |
| 5E9 | — | 93.5 | 78.0 | 96.7 | 66.1 | 75.8 | 87.1 |
| A10.1 | 70 | 91.9 | 61.3 | 101.6 | 48.4 | 50.0 | 45.2 |
| A31.1 | 40 | 91.2 | 59.6 | 96.2 | 43.1 | 44.2 | 43.7 |

TABLE 7-continued

Ovr110-CHO killing by Ovr110 MAb & MAb Zap Saporin Conjugate

| | % | Percent Growth Compared to Wells with Medium Alone | | | | | |
|---|---|---|---|---|---|---|---|
| | Ovr110-CHO Positive with | Ovr110-CHO MAb (2 ug/mL) + | | | MAb + MAb Zap | | |
| MAb Clone | MAb (IF)* | MAb Zap | MAb Zap | Mab (2 ug/mL) | MAb (0.08 ug/mL) | MAb (0.4 ug/mL) | MAb (2 ug/mL) |
| A57.1 | 40 | 100.0 | 57.7 | 101.9 | 36.6 | 36.5 | 42.3 |
| A87.1 | 70 | 92.2 | 58.8 | 98.0 | 45.8 | 39.2 | 43.1 |
| C3.2 | 60 | 97.0 | 71.7 | 98.9 | 50.9 | 55.5 | 56.6 |
| C5.1 | 40 | 98.1 | 73.1 | 100.0 | 52.0 | 50.0 | 46.9 |
| C5.3 | 40 | 96.2 | 75.0 | 103.8 | 57.7 | 53.8 | 59.6 |
| C6.3 | 40 | 96.2 | 73.1 | 100.1 | 51.9 | 43.1 | 50.0 |
| C9.1 | 20 | 98.1 | 78.1 | 102.6 | 58.5 | 80.0 | 67.9 |
| C11.1 | 1 | 98.0 | 78.4 | 101.9 | 58.8 | 70.6 | 80.4 |
| C12.1 | 20 | 100.0 | 80.4 | 103.9 | 66.7 | 72.5 | 78.4 |

*Immunofluorescence microscopy as detailed in Example 2.

Results of testing Ovr110.A10.1, Ovr110.A31.1, Ovr110.A57.1, Ovr110.A87.1, Ovr110.C3.2, Ovr110.C5.1, Ovr110.C5.3, Ovr110.C6.3, Ovr110.C9.1, Ovr110.C11.1 and Ovr110.C12.1 are presented in Table 8. As can be seen, the MAb Zap alone resulted in a high background and inhibited growth of the Ovr110-CHO cells from 0-41.4%. This was not the case for the negative control wells with Pro104-CHO cells and MAb Zap alone, which resulted in 0-10% growth inhibition (data not shown). However, none of the Ovr110 MAbs alone, produced more than 3.8% growth inhibition of Ovr110-CHO cells. Whereas, when added with MAb Zap saporin conjugate, all of the Ovr110 MAbs tested produced greater than 10% more growth inhibition than with MAb Zap alone. Ovr110.A57.1 in particular, at concentrations of 0.08, 0.4 and 2.0 ug/mL together with MAb Zap resulted in 15.4-21.1% greater Ovr110-CHO cell growth inhibition, than MAb Zap alone and 57.7-63.4% growth inhibition compared to wells with medium alone. In conclusion, growth inhibition of Ovr110 expressing CHO cells, was obtained at concentrations of MAb which are easily achievable in-vivo, for therapeutic purpose. These in-vitro data suggest that the Ovr110 MAbs above would be suitable for targeting of drug or isotopes to tumor cells, in-vivo.

Example 4

Binding of Ovr110 MAbs and Soluble BTLA-Fc to Activated T-Cells and Tumor Cells

Anti-human B7x/B7H4 and anti-mouse B7S1 MAbs were previously shown to bind to activated T-cells (Prasad et al., Immunity 18:863-73 (2003); Sica et al., Immunity 18:849-61 (2003); Zang et al., Proc. Nat.l Acad. Sc.i USA. 100:10388-92 (2003)). In order to verify binding of the Ovr110 MAbs of this invention to activated cells, fresh human T-cells were purified and stimulated with different compounds, as discussed infra. The binding of the Ovr110 MAbs to activated CD3 positive T-cells expressing CD25 (IL-2R) and CD71 (TFR) was analyzed by FACS. Because BTLA has been identified as the putative receptor for Ovr110 (B7x/B7H4) (Watanabe et al., Nat. Immunol. 2003 4:670-9; Carreno & Collins Trends Immunol. 2003 24:524-7), we also examined the binding of the human BTLA-mouse IgG2a Fc fusion disclosed herein to these activated T-cells and tumor cells.

Preparation of Human Peripheral Blood Leukocytes (PBL)

Human peripheral blood from normal, male donors was obtained from volunteer donors at Stanford Blood Center (Palo Alto, Calif.). Mononuclear cells were isolated using standard Ficoll/Hypaque single step density gradient centrifugation (1.077 g/nL) methods.

Activation of T-Cells

Mononuclear cells at a final concentration of $10^6$/mL were cultured for 3 days, at 37° C., in RPMI-1640 (CellGro), supplemented with 10% FCS (Hyclone, Utah), with phytohemagglutinin (PHA-M) (Sigma, St. Louis, Mo.) at 10 ug/mL, or lipopolysaccharide (LPS) (Sigma) at 10 ug/mL, or a combination of phorbol myristic acetate (PMA) (Sigma) at 10 ng/mL and ionomycin (Sigma) at 1 uM, in standard 25 cm$^2$ tissue culture flasks in 10% $CO_2$.

Immunofluorescence and Flow Cytometry

The cells were collected after 3 days of PHA stimulation and washed extensively. The mononuclear cells were distributed into a 96 well V-bottom plate and incubated in autologous serum to block Fc receptors. Anti-CD3 FITC antibody (Serotec, Raleigh, N.C.) was added to each well and either CD80PE, CD86PE, CD25PE, or biotinylated anti-CD71 (Serotec), Ovr110.A57.1 or Ovr110.C3.2 were added as a second MAbs, at 20 ug/mL, for dual color analysis. The cells were washed twice and Phycoerythrin-Streptavidin (PESA) was added to the wells preincubated with biotinylated MAbs. The cells were washed twice and resuspended in FACS buffer. Cells were preincubated in autologous serum and stained with Ovr110-Ig or BTLA-Ig fusion proteins, at 20 ug/mL. The cells were washed twice, donkey anti-mouse PE (1 ug/mL) was added to the samples and the cells were then washed twice and incubated in mouse serum to block free binding sites on the donkey anti-mouse antibody. Anti-CD3 FITC antibody was then added as a last step to identify T-cells. After washing twice, the cells were resuspended in FACS buffer and analyzed by flow cytometry. The human tumor cell line SKBR3 was incubated with MAbs or BTLA-Fc as previously described above.

All samples were analyzed on an EPICS Elite Flow Cytometer. All histograms were generated using the Winmdi program. CD3 positive T cells were used as a gate to analyze the expression of the B7 family and activation markers (CD71 and CD25).

TABLE 8A

Binding of anti-Ovr110 MAbs to tumor cells and activated T-cells

| | HT29 (QPCR−) | | SKBR3 (QPCR+) | | Resting (0 h) T-Cells | | PHA 72 h Activated T-Cells | |
|---|---|---|---|---|---|---|---|---|
| | % Cells | MFI* | % Cells | MFI | % Cells | MFI | % Cells | MFI |
| Neg. Control (Pro104 D9.1) | 2 | 0.5 | 2 | 0.6 | 4 | 6.4 | 1 | 8 |
| CD25 | | | | | 0 | 7.6 | 77 | 19 |
| CD71 | 100 | 50 | 99 | 217 | 8 | 7.6 | 95 | 219 |
| A7.1 | 2 | 0.5 | 71 | 4.2 | | | | |
| A57.1 | 2 | 0.6 | 4 | 1 | 6 | 10 | 82 | 246 |
| A72.1 | 21 | 1.0 | 6 | 1.2 | | | | |
| C3.2 | 1 | 0.5 | 60 | 3.6 | 6 | 10 | 2 | 5 |

*Mean of fluorescence intensity

TABLE 8B

Binding of Anti-Ovr110 MAbs to PHA Activated T-cells from Normal Male Donors

| | N | Day 0% Cells Positive (Average ± St Dev) | N | Day 3% Cells Positive (Average ± St Dev) |
|---|---|---|---|---|
| Neg. control | 5 | 1.8 ± 1.4 | 6 | 1.9 ± 0.4 |
| Total CD3+ | 5 | 82.6 ± 14.1 | 6 | 92.4 ± 6.4 |
| | | Percentage of CD3 Gated Cells Positive | | |
| Ovr110.A57.1+ | 5 | 2.8 ± 1.7 | 6 | 57 ± 34.0 |
| Ovr110.C3.2+ | 3 | 3.2 ± 2.6 | 5 | 8.8 ± 12.4 |
| CD80+ | 5 | 1.2 ± 0.8 | 6 | 3.6 ± 3.1 |
| CD86+ | 5 | 1.4 ± 0.8 | 6 | 12.8 ± 11.4 |
| CD25+ | 5 | 1.9 ± 1.1 | 6 | 86.3 ± 8.1 |
| CD71+ | 5 | 7.2 ± 1.0 | 6 | 95.9 ± 3.5 |
| Ovr110-Fc | 1 | 0.9 | 4 | 82.8 ± 15.9 |
| BTLA-Fc | 1 | 1.4 | 4 | 20.2 ± 32.5 |

TABLE 8C

Binding of anti-Ovr110 MAbs to Activated B Cells, Dendritic Cells and Monocytes

Percent Cells Positive by FACS

| | B Cells (CD19+) | | Dendritic Cells (CD1c+) | | Monocytes (CD14+) | |
|---|---|---|---|---|---|---|
| MAb | 0 h | 72 h | 0 h | 72 h | 0 h | 72 h |
| Negative Control | 1 | 2 | 1 | 1 | 1 | 1 |
| Positive Control | 31 | 22 | 11 | 15 | 94 | 96 |
| Ovr110.A57.1 | 12 | 13 | 26 | 72 | 8 | 22 |
| CD80 | 16 | 16 | 14 | 2 | 4 | 4 |
| CD86 | 5 | 27 | 50 | 94 | 70 | 20 |
| CD25 | 3 | 14 | 2 | 1 | 1 | 2 |
| CD71 | 61 | 64# | 89 | 100* | 32 | 72 |

Fluorescence intensity increased ~2-fold over 0 h
*Fluorescence intensity increased 4-fold over 0 h As can be observed in FIG. 7, where the filled curves represent the binding of MAbs to non-stimulated T-cells, and in Tables 8A, 8B and 8C, an increase in the expression of CD25 and CD71 (i.e. increase in PE mean fluorescence) was achieved on the PHA activated T-cells (gated on CD3), compared to non-stimulated T-cells. An increase in the expression of CD71 (i.e. increase in positive cells or fluorescence intensity) was achieved on the activated dendritic cells (gated on CD1c) and activated monocytes. These data demonstrate positive activation of T-cells, dendritic cells and monocytes. The fluorescence profiles in FIG. 7 and Tables 8A, 8B and 8C demonstrate that expression of CD86 (B7.2) and Ovr110 (MAb A57.1) were increased in the activated T-cells and activated dendritic cells and Ovr110 was increased somewhat in activated monocytes.

As a further proof that BTLA is the ligand for Ovr110 we tested the binding of the BTLA-Fc (mouse IgG2a) fusion protein to Ovr110 transfected 293F cells (Ovr110-293F). From FIGS. 7G, 7H and 7I, it may be observed that the BTLA-Fc fusion protein bound significantly to the Ovr110-293F cells (17% cells positive, MFI 24.57), but not to the control 293F cells (2% cells positive, MFI 3.44). Furthermore no appreciable binding of the mouse IgG2a to Ovr110-293F cells via the Fc fragment was observed (3% cells positive, MFI 4.32). From the data presented in Table 8B, the binding of BTLA-Fc and Ovr110-Fc to activated cells, and FIGS. 7G, 7H and 7I, the binding of BTLA-Fc to Ovr110-293F cells, it is apparent that these two recombinant proteins may be useful as diagnostic or therapeutic agents, by blocking tumor function. In addition, modified versions of BTLA-Fc and Ovr110-Fc conjugated to, e.g., a cytotoxic or cytostatic component, or other functionality, could be also used as a therapeutic agent.

The data presented in Tables 8A and 8B, demonstrate that the MAb A57.1 apparently binds preferentially to the activated T-cells, and MAb C3.2 binds preferentially to the tumor cell line SKBR3. These data suggest differences between the epitopes that these two MAbs bind to, which may be important in decreasing the immune suppressing effects of tumor-expressed or shed Ovr110, but which also may be important in minimizing any immunosuppressive effect due to the use of Mab C3.2 as a therapeutic anti-tumor antibody.

Example 5

Functional Validation of Ovr110

Materials and Methods

Cells and Cell Culture

RK3E, 293T, IEC-18, SKOV3, HeLa, CaOV3, HT29, MCF7 and SKBR3 cell lines were purchased from American Type Culture Collection (Manassas, Va.). Cells were grown in DMEM (Invitrogen) with L-glutamine plus 4.5 g/L glucose and supplemented with 10% FBS and 100 U/mL Penicillin/Streptomycin (Cellgro). All cells were maintained in a humidified 37° C. incubator with 5% CO2.

siRNA Oligonucleotide Design and Preparation

To design siRNA molecules, sequences were selected from the open reading frame of the Ovr110 mRNA based on methods previously described (Elbashir et al., 2001). A random "scrambled" siRNA sequence which should not generate knockdown of any known cellular mRNA was used as a negative control. As an additional negative control, a siRNA targeting Emerin was used to demonstrate that knockdown of a non-essential mRNA did not affect Ovr110 levels nor any of the biological endpoints studied (data not shown). As a positive control for knockdown of an mRNA leading to apoptosis induction, a siRNA targeting DAXX was used, based on published data (Michaelson et al., J Cell Sci. 2003 Jan. 15; 116(Pt 2):345-52). A BLAST search against the human genome was performed with each selected siRNA sequence to ensure that the siRNA was target-specific and would not function to knockdown other sequences. All siRNA molecules (HPP purified grade) were chemically synthesized by Xeragon Inc. (Germantown, Md.). siRNA's were dissolved in sterile buffer, heated at 90° C. for 1 minute and then incubated at 37° C. for 1 hour prior to use. siRNA oligonucleotides with two thymidine residues (dTdT) at the 3' end of the sequence consisted of the following specific RNA sequences:

```
Ovr110 #37:
sense 5'-GGUGUUUUAGGCUUGGUCC-3'    (SEQ ID NO: 14)
(BEST)

Ovr110 #39:
sense 5'-CUCACAGAUGCUGGCACCU-3'   (SEQ ID NO: 15)

Ovr110 #41:
sense 5'-GGUUGUGUCUGUGCUCUAC-3'   (SEQ ID NO: 16)

Emerin:
sense 5'-CCGUGCUCGUGGGGCUGGG-3'   (SEQ ID NO: 17)

Scrambled:
sense 5'-UUCUCCGAACGUGUCACGU-3'   (SEQ ID NO: 18)

DAXX:
sense 5'-GGAGUUGGAUGUGUCAGAA-3'   (SEQ ID NO: 19)
```

Transfection with siRNA Oligonucleotides $6 \times 10^4$ SKBR3 cells were seeded in 12-well plates for 18-24 hours prior to transfection. Transient transfection was carried out using Oligofectamine reagent (Invitrogen) according to the manufacturer's protocol. A final concentration of 100 nM siRNA (except DAXX siRNA which was 200 nM) and 1.5 ul Oligofectamine were used per well of cells. siRNA's were transfected in triplicate for all experiments. Parallel wells of cells were evaluated 72 hours after transfection for changes in mRNA levels by quantitative real-time RT-PCR (QPCR), changes in protein levels by Western immunoblot and changes in apoptosis by two different assay systems (see below). The results demonstrating down regulation of the Ovr110 protein are shown in FIG. 11. The siRNA #37 against Ovr110 was also tested with cells that did not express Ovr110 and there was no effect on apoptosis (data not shown). All findings were confirmed with at least 2 additional experiments.

Quantitative Real Time RT-PCR (QPCR)

A QuantiTech SYBR Green RT-PCR kit from Qiagen Inc. was used for QPCR evaluation. Between 20 and 40 ng of template RNA was used per reaction. QPCR was performed using a Taqman 7700 Sequence Detection system (Applied Biosystem Inc).

Apoptosis Assays

Figure 13B:
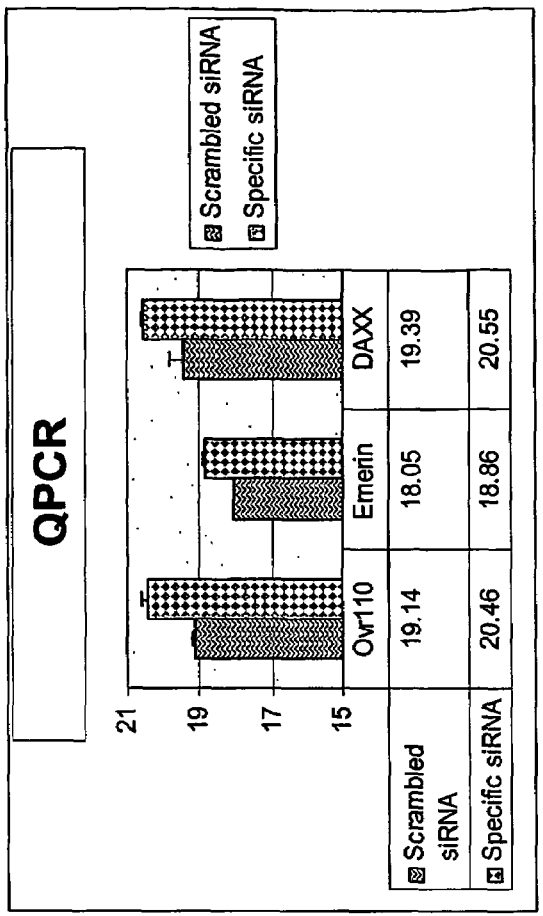
FIGS. 13A and 13B show that knockdown of Ovr110 mRNA induces caspase activity in SKBR3 cells.
Figure 13A:
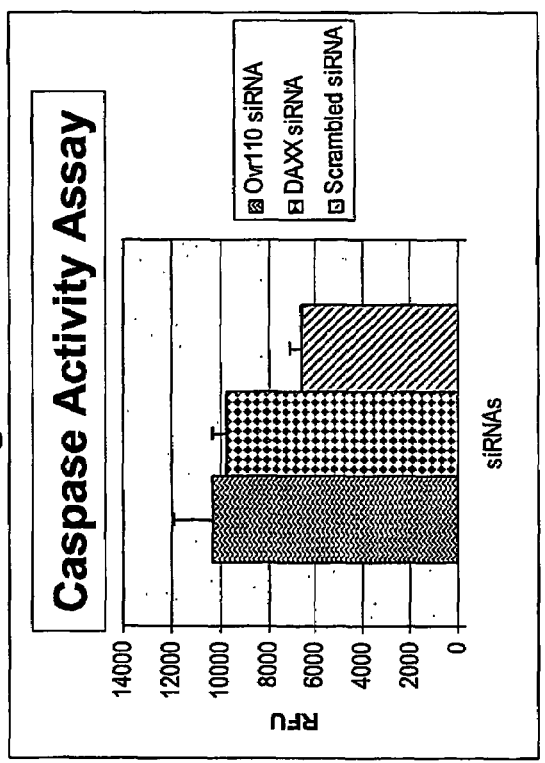

Two different assay kits were used to evaluate the effects of siRNA on apoptosis. With the "Apo-ONE Homogeneous Caspase-3/7 Assay" kit (Promega Inc.) the test cells were solubilized directly in the culture plate and caspase activity, reflected as a fluorescent readout, was measured according to supplier's instructions. With the second kit, "Guava Nexin V-PE Kit" (Guava Technologies Inc.), treated cells were harvested by trypsinization and washing and approximately $10^5$ cells were resuspended in 40 ul provided buffer and 5 ul each Annexin V (+) and 7-AAD (−) were added. Following 20 minutes incubation on ice, cells were analyzed using the Guava PCA Flowcytometer according to manufacturer's instructions. The results demonstrating that Ovr110 knockdown induces apoptosis are shown in FIG. 12 and FIG. 13.

For the anoikis assays IEC-18 and RK3E cells expressing the genes indicated were trypsinized and re-suspended in FBS free media at a density of 150,000 and 200,000 cells/ml, respectively. A 1 ml aliquot of the mix was plated into each well of a 12-well plate and the samples incubated at 37° C. for 24 hrs. Cells were then collected and evaluated using the Guave-Nexin V-PE kit as above. Ras, a potent oncogene, served as a positive control and AP as a negative control for the anoikis assay. The results are shown in FIG. 15.

SDS-PAGE and Western Immunoblot Analysis 72 hrs after transfection with siRNA, cell extracts were prepared on ice using solubilization buffer (1% NP40, 10 mM Na2PO4, 0.15M NaCl) plus a protease inhibitor cocktail (Roche Inc.). Extracts for other experiments with virus infected or untransfected cells were prepared in a similar fashion. Protein extracts from harvested tumors were prepared by homogenization of snap-frozen, minced tumor tissue in extraction buffer (50 mM Tris-HCl, pH=7.2, 150 mM NaCl, 5 mM EDTA, 0.5% IG-Pal plus protease inhibitors) followed by sonication and then centrifugation in a microfuge to clarify the extracts. Between 20 and 50 ug of protein extract were used for each gel lane; protein equivalent concentrations were evaluated for protein level comparisons on the same gel. Clarified extracts were mixed with an equal volume of 2× concentrated Laemmli sample buffer (Invitrogen), heated to 70° C. for 10 minutes and then analyzed using pre-cast 4-12% SDS-polyacrylamide minigels (Nupage, Invitrogen) with MES rnning buffer (Nupage; Invitrogen). Gels were transferred to Immobilon-P PVDF membranes (0.45 µm pore size, Invitrogen) using 1×Nupage transfer buffer plus 10% Methanol. The membranes were rinsed and blocked for 1 hour at room temperature using 5% nonfat dry milk in PBS with 0.05% Tween-20. Membranes were incubated with primary antibody overnight in 5% nonfat dry milk in PBS with 0.05% Tween-20. A mouse monoclonal antibody directed against Ovr110 was produced using recombinant Ovr110 protein. The monoclonal antibody against Ovr110 was used at a final concentration of 1 ug/ml and a mouse monoclonal antibody against GAPDH (Chemicon Inc.) at a final concentration of 2 ug/ml. Following primary antibody incubation, membranes were washed four times at room temperature for 10 min. each in 1×PBS with 0.05% Tween-20. Horseradish peroxidase linked goat anti-mouse immunoglobulin (Jackson Lab Inc.) was used (1:10,000 dilution) in 5% nonfat dry milk in PBS plus 0.05% Tween-20 for 1 hour at room temperature to detect the primary monoclonal antibody. Membranes were finally washed four times for 10 min. in 1×PBS plus 0.05% Tween-20 followed by detection using enhanced chemiluminescence (ECL) reagent per manufacturer's directions (Amersham).

Expression Vector Construction

For expression of Ovr110 protein in mammalian cells, Ovr110 cDNA was sub-cloned into the pLXSN vector (BD Bioscience/Clontech) and sequence verified. The pLXSN retrovirus vector utilizes the MLV LTR to drive expression of cDNA's cloned into the multiple cloning site and an SV40 promoter driving expression of a Neo gene encoding G418 resistance. pLAPSN, a retroviral expression vector encoding alkaline phosphatase (AP), was purchased from BD Bioscience/Clontech (pLXSN-AP).

Virus Production

Ecotropic virus was used to infect RK3E and IEC-18 cells and amphotropic virus to infect SKOV3 cells. For ecotropic virus packaging, one day prior to transfection, 293T cells were seeded at a density of $8 \times 10^5$ cells per well of a 6 well dish onto Biocoat collagen coated plates (BD). Cells were transfected with purified plasmid DNA's using Lipofectamine with the addition of PLUS reagent (Invitrogen). Per well of cells 0.8 µg of virus plasmid DNA: pLXSN-Ovr110, pLXSN-Ovr110HA or pLXSN-AP plus 0.8 µg pVpack-ECO and 0.8 µg pVpackGP (Stratagene) were added to a stock of 125 µL DMEM without serum and 10 µL of PLUS reagent followed by incubation for 15 minutes at room temperature. Subsequently, 8 µL of lipofectamine diluted into 125 µL of DMEM medium were added to the DNA/PLUS reagent mixture and incubated for 15 minutes as room temperature. One ml of DMEM was added to the final lipofectamine/DNA mixture and applied to the cell monolayer, already containing 1 ml DMEM without serum, followed by incubation at 37° C. for 3 hours. The transfection mix was replaced with DMEM containing 20% FBS and cells grown overnight. Finally, the media was changed to DMEM supplemented with 10% FBS+100 U/mL Pen/Strep for virus collection. Virus-containing media were harvested 24 hours later and filtered through a 0.45 μm polysulfonic filter. For ampho-tropic virus packaging the same procedure was followed except that the pVpack Ampho plasmid (Stratagene) was used instead of the pVpack Eco plasmid.

Virus Infection and Selection

Polybrene (Hexadimethine Bromide; Sigma) was added to fresh virus-containing medium at a final concentration of 4 μg/ml. RK3E, IEC-18 or SKOV3 cells, plated the day before at a density of $3 \times 10^5$ cells per 100 mm2 dish, were washed once with phosphate-buffered saline including Ca2+ and Mg2+ (cellgro). The virus solution (6 ml per 100 mm2 dish) was applied directly to the cells and then incubated for 3 hours in a humidified 37° C. incubator with 5% CO2 with occasional swirling. The virus-containing medium was replaced by fresh growth medium and the cells incubated at 37° C. for 60-72 hours at which point a final concentration of 350 ug/mL of G418 sulfate (Cellgro) was included in the growth medium to select for virus-infected cells. Cells were maintained between 70-80% confluence and G418-containing media was changed every 2 days. Following G418 selection, pools of cells were used for subsequent experiments including verification of Ovr110 protein expression by Western immunoblot analysis where cells were extracted and analyzed as described above. Expression of AP by infected cell monolayers was monitored by staining whereby monolayers of cells were fixed for 10 minutes at room temperature with a solution of 0.5% glutaraldehyde, rinsed with PBS, heated to 65° C. for 30 minutes and AP was visualized by incubation with BCIP/NBT liquid substrate (Sigma) for 2-3 hours.

Tumor Xenograft Experiments

Figure 14:
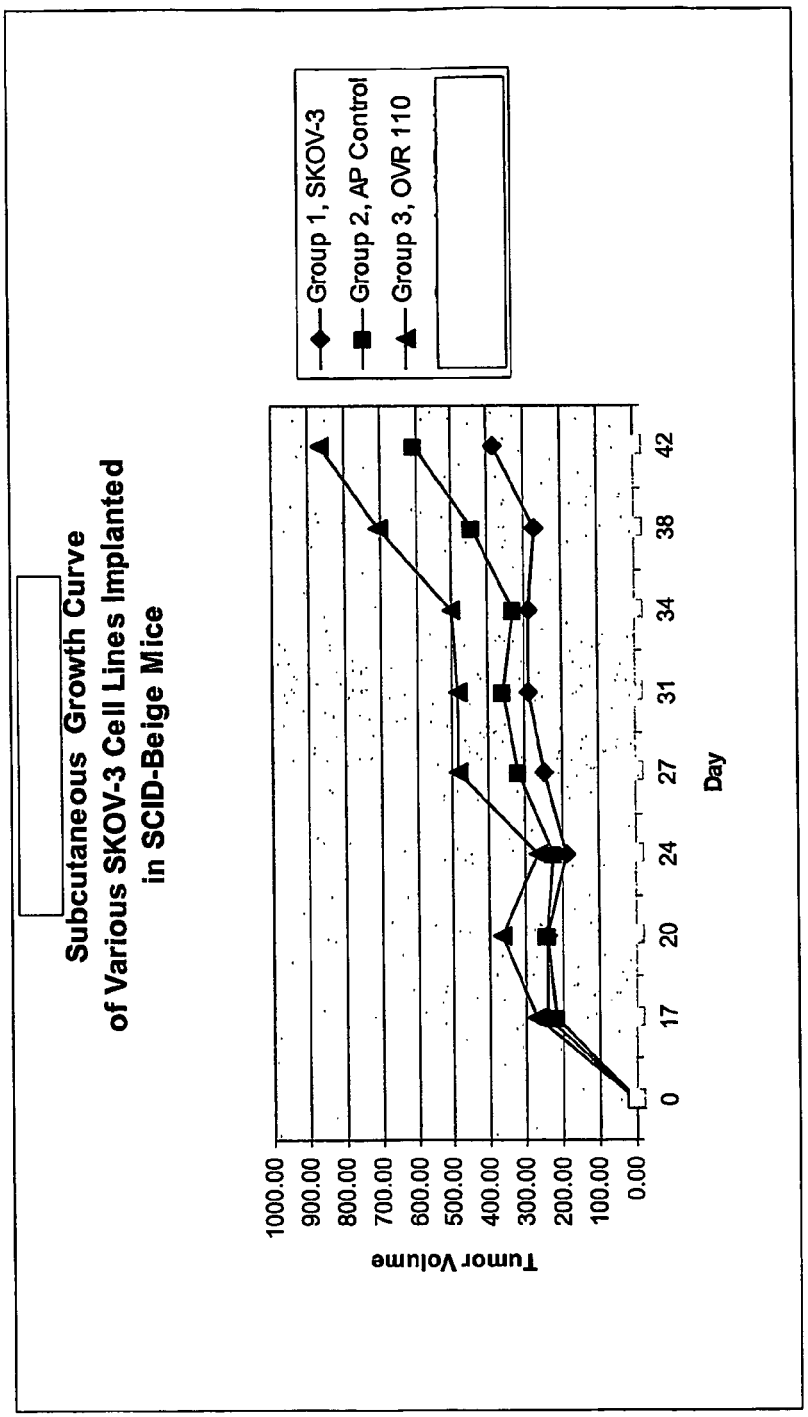
FIG. 14 shows that overexpression of Ovr110 enhances tumor xenograft growth.

Retrovirus-infected, G418-selected pools of SKOV3 cells expressing either AP or Ovr110 were injected subcutaneously into nude mice. Parental SKOV3 cells were also used for comparison. $10^7$ of each cell type were implanted with matrigel into each of 6 mice. 100% of mice injected with tumor cells developed tumors and tumor formation was monitored by palpation and caliper measurement when possible every 4 days for the duration of the study. The results are shown in FIG. 14. Data is expressed as mean group tumor volume over time.

Example 6

Monoclonal Sandwich ELISA Detection of Ovr110

High binding polystyrene plates (Corning Life Sciences (MA)) were coated overnight at 4° C. with 0.8 μg/well of anti-Ovr110 MAb. The coating solution was aspirated off and free binding sites were blocked with 300 μl/well Superblock-TBS (Pierce Biotechnology, Illinois) plus 100% calf serum for 1 hour at room temperature (RT). After washing 4× with TBS+0.1% Tween20, 50 μl of Assay Buffer (TBS, 1% BSA, 1% mouse Serum, 1% Calf Serum, 0.1% Tween20) was added to each well and then 50 μl of antigen was added for 90 minutes incubation. For the checkerboard experiment, each pair was tested on 50 ng/ml and 0 ng/ml of recombinant mammalian Ovr110 (extracellular portion). For each sandwich ELISA, standards of 10, 2.5, 0.5, 0.25, 0.1 and 0 ng/ml Ovr110 were run in parallel with the test samples. Standards and test samples were diluted in Assay Buffer. For the detection, 100 μl of biotinylated MAb (1 μg/ml) were added to each well and incubated for 1 hour at room temperature, while shaking. After washing, 100 μl of horseradish peroxidase conjugated streptavidin (1 mg/ml, Jackson ImmunoResearch Laboratories, PA) at a 1:20.000 dilution was added to each well and incubated for 30 minutes at RT while shaking. After washing, the plate was then developed using DAKO TMB Plus substrate (DAKO, Denmark) for 30 minutes at RT. The reaction was stopped using 100 μl/well 1N HCL, and the plates were read at 450 nm using a Spectramax 190 plate reader (Molecular Devices, CA).

For the checkerboard ELISA, all possible combination of antibodies, were tested for efficiency as coating or detecting reagents. The pairs A72.1/A7.1, A77.1/A57.1, A57.1/A7.1 and A57.1/C3.2 gave the best signal/noise ratio and were further evaluated in sandwich ELISA assays to analyze the efficiency of detection of endogenous Ovr110 in lysates from cancer cell lines and body fluids. The pair A72.1/A7.1 was used to test the 2700 serum samples listed below.

Results

The results of the checkerboard ELISA on 10 MAb of the A-series and 8 MAb of the C-series are shown in Tables 9A and 9B. Each antibody was tested as both a coating and detecting antibody, in all possible combination. All pairs were tested in duplicates with 100 ng of recombinant Ovr110B protein in buffer, with buffer alone as a blank. The results are shown as specific signal/noise ratio. The MAbs detect two distinct epitopes, based on these pairing data. The Ovr110 A7, A77, A87 and A10 MAbs react with one epitope or epitopes which are close enough to sterically hinder the binding of the other three MAbs. All C-series antibodies detect this epitope (or overlapping epitopes) as well. The other distinct epitope or epitopes is detected by Ovr110 A89, A57, A31, A72, A107 MAbs. Several pairs with the highest signal/noise ratio were used to test sensitivity for recombinant protein, reactivity towards native protein in cell lines and some initial serum samples.

Epitope Specificities—Binning of MAb & Epitope Mapping

TABLE 9A

Pairing of Ovr110 A-series MAb by Sandwich ELISA

| Coating MAb | Detecting MAb | | | | | | | | | |
|---|---|---|---|---|---|---|---|---|---|---|
| | A7 | A10 | A13 | A22 | A31 | A57 | A77 | A87 | A89 | A107 |
| A7 | 1.8 | 2.9 | 1.1 | 9.7 | 7.24 | 10 | 2.4 | 1.7 | 7.9 | 9.7 |
| A10 | 3.5 | 3.2 | 3.5 | 19.9 | 14.4 | 19.9 | 4.5 | 3.5 | 16.6 | 18.5 |
| A13 | 1.5 | 4.8 | 1.1 | 7.9 | 5.9 | 8.1 | 2.1 | 1.4 | 6.2 | 8.1 |
| A22 | 21 | 25 | 6.5 | 5.8 | 3.6 | 7.13 | 12.6 | 15.5 | 4.7 | 5.8 |
| A31 | 11.6 | 18.77 | 4.8 | 7.9 | 4.7 | 8.5 | 6.8 | 11.1 | 6.1 | 7.7 |
| A57 | 7.1 | 26 | 7 | 8.5 | 5.7 | 9.7 | 13.3 | 14.5 | 7.1 | 8.7 |
| A77 | 7.7 | 12 | 2.9 | 17.3 | 16 | 19.6 | 2 | 7.3 | 16.6 | 18.8 |
| A87 | 1.7 | 2.7 | 1.1 | 7.1 | 5.6 | 8 | 2 | 1.6 | 6.2 | 7.8 |
| A89 | 18 | 22.5 | 6.9 | 8.2 | 5.7 | 8.9 | 12.2 | 14.2 | 6.9 | 8.7 |
| A107 | 21.5 | 25.5 | 6.7 | 7.3 | 4.7 | 7.9 | 12.7 | 15.4 | 5.7 | 7.3 |

TABLE 9B

Pairing of Ovr110 C-series MAb by Sandwich ELISA

| Coat MAb | Det MAb | | | | | | | | | | | |
|---|---|---|---|---|---|---|---|---|---|---|---|---|
|  | C3.2 | C5.1 | C5.3 | C7 | C9 | C11 | C12 | C17 | A72 | A7.1 | A57.1 | A77.1 |
| C3 | 1 | 1 | 1 | 7 | 2 | 3 | 4 | 1 | 8 | 1 | 8 | 2 |
| C5.1 | 1 | 1 | 1 | 5 | 1 | 2 | 3 | 1 | 6 | 1 | 6 | 1 |
| C5.3 | 1 | 1 | 1 | 6 | 2 | 2 | 3 | 1 | 7 | 1 | 7 | 2 |
| C7 | 12 | 8 | 9 | 1 | 4 | 11 | 14 | 3 | 34 | 14 | 45 | 2 |
| C9 | 1 | 1 | 1 | 2 | 1 | 1 | 2 | 1 | 2 | 1 | 3 | 1 |
| C11 | 4 | 3 | 3 | 14 | 2 | 1 | 7 | 1 | 2 | 5 | 2 | 2 |
| C12 | 2 | 2 | 2 | 4 | 1 | 2 | 1 | 1 | 7 | 3 | 8 | 1 |
| C17 | 1 | 1 | 1 | 3 | 1 | 1 | 2 | 1 | 4 | 1 | 4 | 1 |
| A72 | 11 | 8 | 9 | 3/3 | 5 | 1 | 24 | 3 | 1 | 18 | 1 | 3 |
| A57 | 12 | 8 | 10 | 3/3 | 6 | 1 | 24 | 3 | 1 | 18 | 1 | 8 |
| A77 | 6 | 4 | 4 | 2 | 2 | 5 | 5 | 2 | 19 | 8 | 21 | 1 |
| Control MAb | 1 | 1 | 1 | 1 | 1 | 1 | 1 | 1 | 1 | 1 | 1 | 1 |

Figure 16:
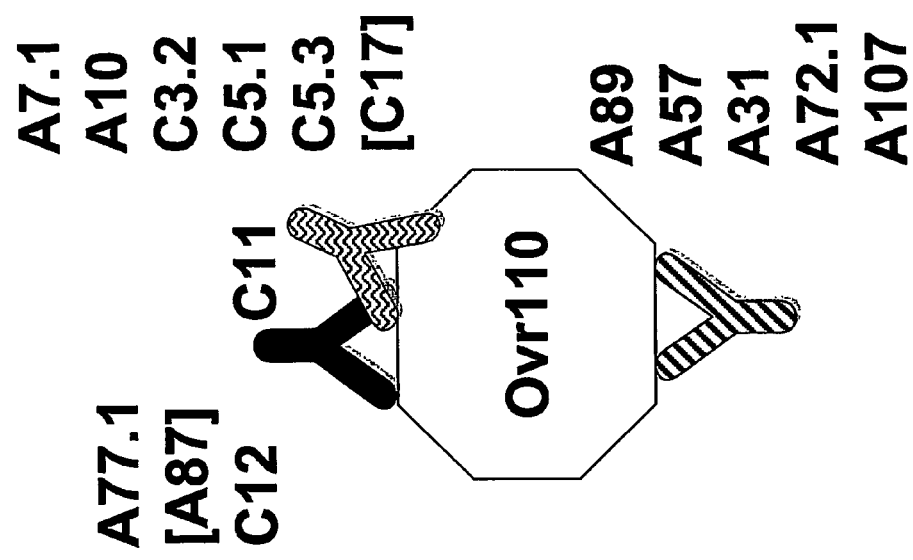
FIG. 16 shows the Ovr110 epitope map for the different antibodies.

The epitope map of the Ovr110 MAbs derived from the results in these tables is shown in FIG. 16.

Human Serum Samples

The human cancer and benign serum samples were obtained from IMPATH-BCP, Inc and DSS (Diagnostic Support Service). The serum samples from healthy women were obtained from ProMedex, LCC. All samples were aliquoted upon arrival and stored at −80C until use.

Results

As described above, for the detection of Ovr110 in serum samples, a sensitive detection system based on the use of horse radish peroxidase (HRP) and a high sensitivity TMB substrate (DAKO), was used. The minimal detectable dose (MDD) for Ovr110 in this ELISA format is 100 pg/ml. For calculation of median values, samples with values below the MDD were defined as 100 pg/ml Ovr110. The minimum detectable dose is defined as two standard abbreviations above the background signal. Most of the serum samples from healthy patients showed low Ovr110 concentrations in the sandwich ELISA while sera from ovarian cancer patients have elevated levels of Ovr110.

We tested the Ovr110 concentration in more than 2700 serum samples from patients with lung, breast, colon, prostate or ovarian cancer or with non-cancerous, benign diseases. For a complete list of all tested samples, see Table 10 below.

TABLE 10

Serum Samples Tested by Sandwich ELISA

| Sample Type | No. of Samples |
|---|---|
| Normal | 555 (281-M, 274-F) |
| Breast Cancer | 260 |
| Breast Benign | 180 |
| Colon Cancer | 150 (71-M, 79-F) |
| Colon Benign | 296 (151-M, 145-F) |
| Lung Cancer | 323 (235-M, 93-F) |
| Lung Benign | 250 (130-M, 120-F) |
| Ovarian Cancer | 236 |
| Ovarian Benign | 150 |
| Prostate Cancer | 138 |
| Prostate Benign | 147 |

Figure 17:
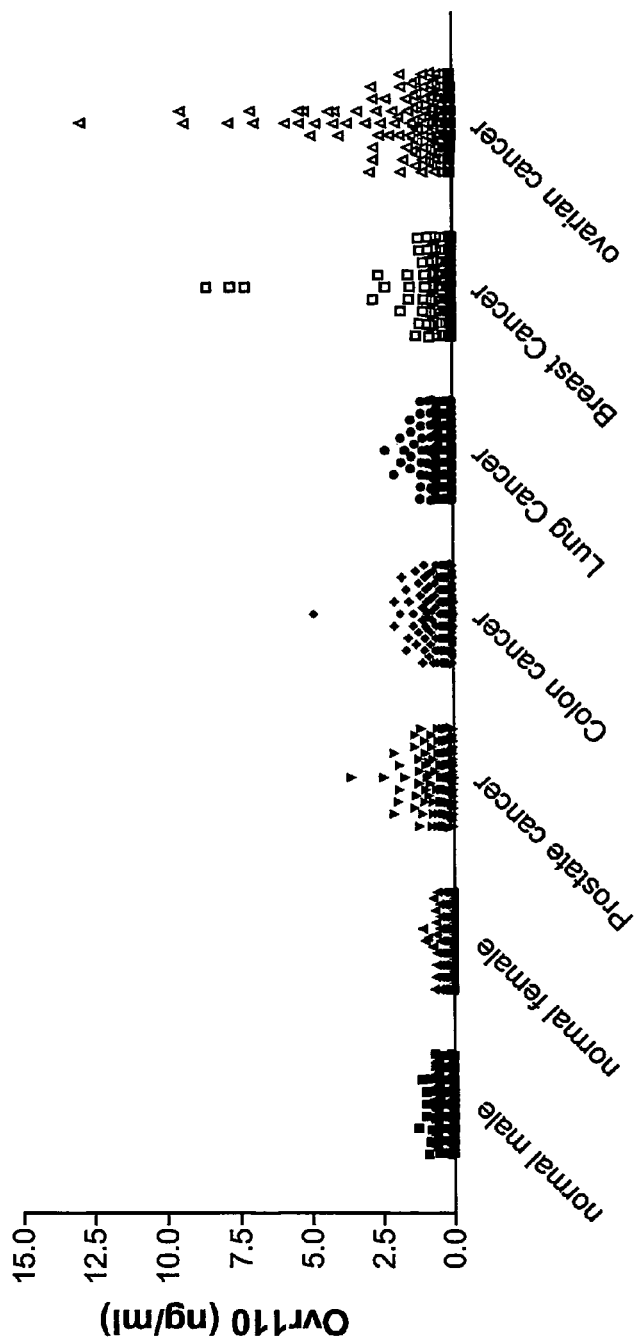
FIG. 17 shows Ovr110 detection in serum of healthy donors and cancer patients.

FIG. 17 shows the Ovr110 concentration in serum from 540 healthy donors and more than 1200 patients with cancer. Elevated levels of Ovr110 are observed in some patients of all cancer types but patients with ovarian cancer have the highest median Ovr110 concentration.

Figure 18:
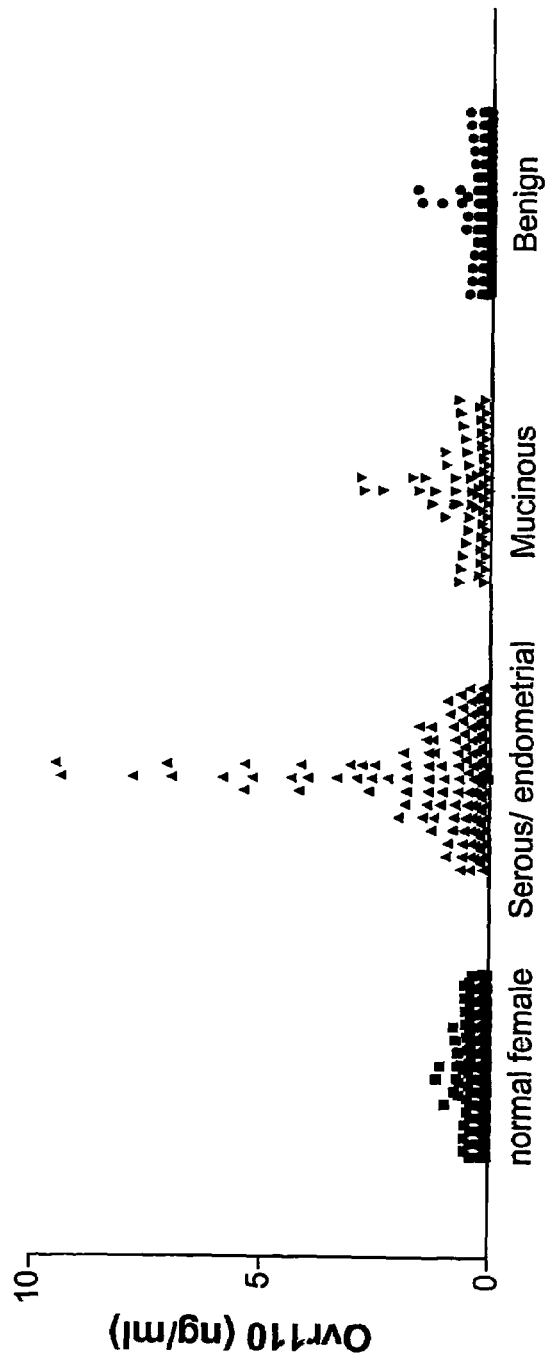
FIG. 18 shows Ovr110 detection of different types of ovarian cancer and benign disease samples.
Figure 19A:
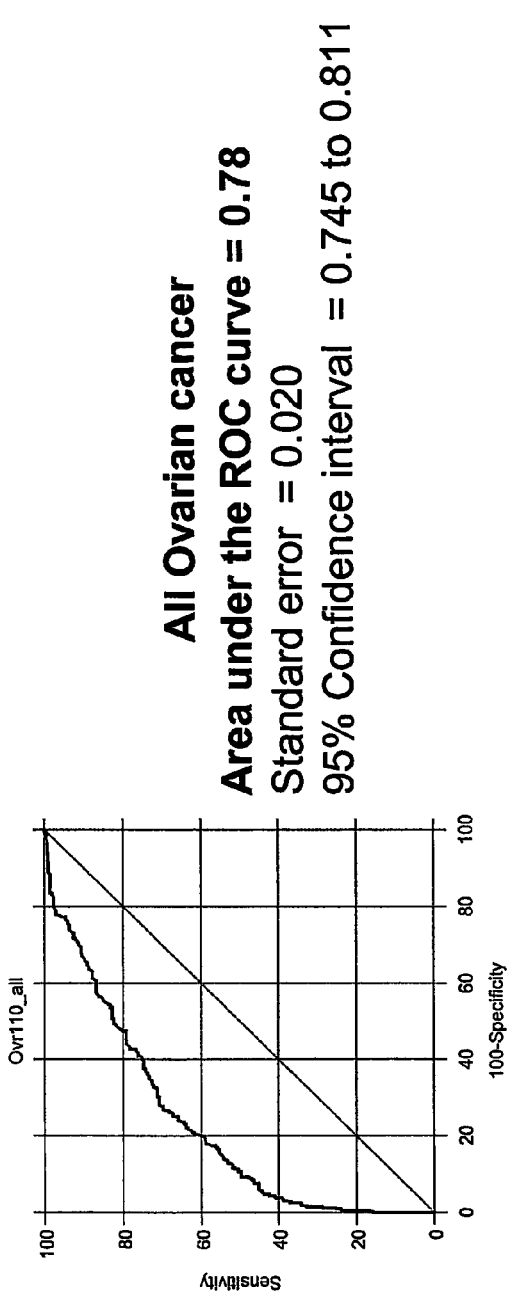
FIGS. 19A and 19B show the Receiver Operator Characteristic (ROC) curves for detecting Ovr110 in all ovarian cancers (FIG. 19A) and serous ovarian cancer (FIG. 19B).
Figure 19B:
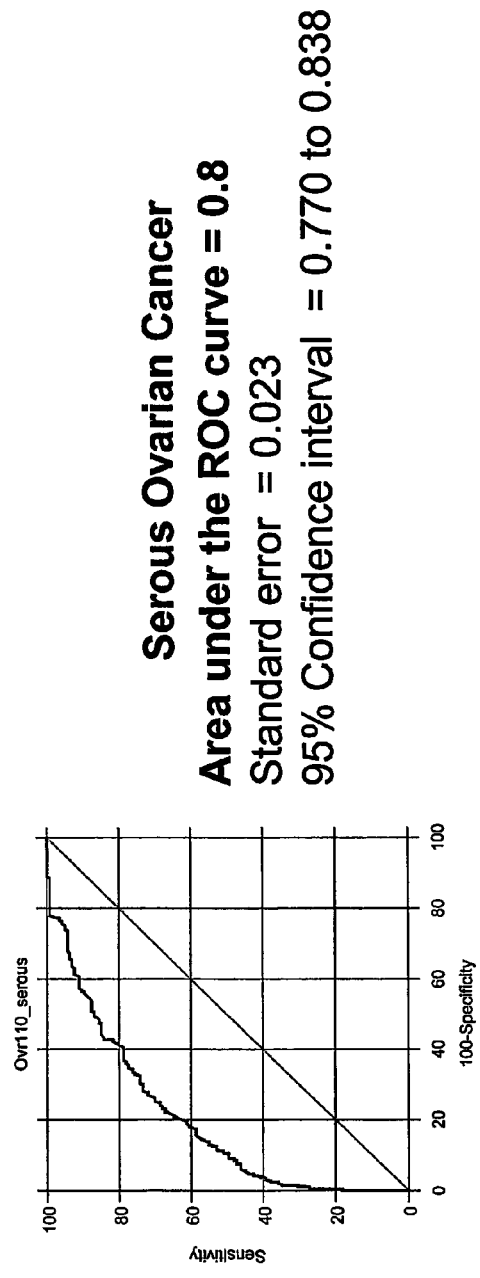

We tested the concentration of Ovr110 in sera of one hundred forty seven women with serous or endometrial ovarian cancer and sixty seven sera of women with mucinous cancer, using sera which represent all four stages of tumor progression. As shown in FIG. 18, the first two ovarian cancer types are positive for Ovr110 by IHC while mucinous cancer is not. In good agreement with these data, the median Ovr110 concentration in serum of patients with endometrial and serous cancer is higher than in mucinous cancer patients.

When compared with healthy women, the median concentration of Ovr110 in serous and endometrial cancer is more than 2-fold higher. Most of the women in this group of 260 healthy women are above 50 years of age to mirror the age distribution of women with ovarian cancer. We can not see differences in Ovr110 detection in healthy women of pre-menopause and post-menopause age. More important, we also do not detect an elevated level of Ovr110 in sera of one hundred fifty women with benign ovarian diseases (50 sera of patients with endometriosis, enlarged ovaries and polycystic ovaries, respectively)

In agreement with our findings that Ovr110 is expressed as a cell surface membrane protein, the overall concentration of Ovr110 in serum is very low even in women with serous cancer. Hence, the Ovr110 concentration detected in sera from women with serous cancer is below 20 ng/ml.

Example 7

Deposits

Deposit of Cell Lines and DNA

The following hybridoma cell lines were deposited with the American Type Culture Collection (ATCC), located at 10801 University Boulevard, Manassas, Va. 20110-2209, U.S.A., and accorded accession numbers.

Ovr110.A57.1 (PTA-5180) was deposited May 8, 2003. Ovr110.A7.1 (PTA-5855) and Ovr110.A72.1 (PTA-5856) were deposited Mar. 11, 2004. Ovr110.C3.2 (PTA-5884) was deposited Mar. 23, 2004. The names of the deposited hybridoma cell lines above may be shortened for convenience of reference. E.g. A57.1 corresponds to Ovr110.A57.1. These hybridomas correspond to the clones (with their full names) listed in Table 11.

TABLE 11

ATCC deposits

| Hybridoma | ATCC Accession No. | Deposit Date |
|---|---|---|
| Ovr110.A57.1 | PTA-5180 | May 8, 2003 |
| Ovr110.A7.1 | PTA-5855 | Mar. 11, 2004 |
| Ovr110.A72.1 | PTA-5856 | Mar. 11, 2004 |
| Ovr110.C3.2 | PTA-5884 | Mar. 23, 2004 |

These deposits were made under the provisions of the Budapest Treaty on the International Recognition of the Deposit of Microorganisms for the Purpose of Patent Procedure and the Regulations there under (Budapest Treaty). This assures maintenance of viable cultures for 30 years from the date of deposit. The organisms will be made available by ATCC under the terms of the Budapest Treaty, and subject to an agreement between diaDexus, Inc. and ATCC, which assures permanent and unrestricted availability of the progeny of the cultures to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 3 7 CFR §1.14 with particular reference to 8860 OG 638).

The assignee of the present application has agreed that if the cultures on deposit should die or be lost or destroyed when cultivated under suitable conditions, they will be promptly replaced on notification with a viable specimen of the same culture. Availability of the deposited strains are not to be construed as a license to practice the invention in contravention of the rights granted under the authority of any government in accordance with its patent laws. The making of these deposits is by no means an admission that deposits are required to enable the invention

---

We claim:

1. An isolated antibody that binds to Ovr110 with a binding affinity of $10^{-9}$ to $10^{-13}$ M, wherein the antibody competes for binding to the same epitope as the epitope bound by the monoclonal antibody produced by a hybridoma selected from the group consisting of American Type Culture Collection accession number PTA-5180, PTA-5855, PTA-5856 and PTA-5884.

2. The antibody of claim 1, wherein said antibody internalizes upon binding to Ovr110 on a mammalian cell.

3. The antibody of claim 1 which is a monoclonal, chimeric, human or a humanized antibody.

4. The antibody of claim 1, wherein said antibody is a monoclonal antibody produced by a hybridoma selected from the group consisting of American Type Culture Collection accession number PTA-5180, PTA-5855, PTA-5856 and PTA-5884.

5. The antibody of claim 1 which is conjugated to a growth inhibitory agent or a cytotoxic agent.

6. The antibody of claim 5 wherein the cytotoxic agent is selected from the group consisting of toxins, antibiotics, radioactive isotopes and nucleolytic enzymes.

7. The antibody of claim 6, wherein the cytotoxic agent is a toxin selected from the group consisting of ricin, saponin, maytansinoid and calicheamicin.

8. The antibody of claim 1, wherein said antibody inhibits the growth of Ovr110-expressing cancer cells.

9. The antibody of claim 1 which is a monoclonal, chimeric, humanized or human antibody.

10. The antibody of claim 9 which is produced in bacteria.

11. The antibody of claim 8, wherein the cancer cells are from a cancer selected from the group consisting of ovarian, pancreatic, lung and breast cancer.

12. An isolated cell that produces the antibody of claim 1.

13. A composition comprising the antibody of claim 1 and a carrier.

14. The composition of claim 13, wherein the antibody is conjugated to a cytotoxic agent.

15. The composition of claim 13, wherein the antibody is a monoclonal, chimeric, human or humanized antibody and the carrier is a pharmaceutical carrier.

16. A method of killing an Ovr110-expressing cancer cell, comprising contacting the cancer cell with the antibody of claim 1, thereby killing the cancer cell.

17. The method of claim 16, wherein the cancer cell is selected from the group consisting of ovarian, pancreatic, lung and breast cancer cell.

18. The method of claim 16, wherein the antibody is conjugated to a cytotoxic agent.

19. The method of claim 18, wherein the cytotoxic agent is a toxin selected from the group consisting of maytansinoid, ricin, saporin and calicheamicin or a radioisotope.

20. The method of claim 16, wherein the antibody is administered in conjunction with at least one chemotherapeutic agent.

21. The method of claim 20 wherein the chemotherapeutic agent is paclitaxel or derivatives thereof.

22. A method for determining if cells in a sample express Ovr110 comprising
   (a) contacting a sample of cells with an Ovr110 antibody of claim 1 under conditions suitable for specific binding of the Ovr110 antibody to Ovr110, and
   (b) determining the level of binding of the antibody to cells in the sample, or the level of Ovr110 antibody internalization by cells in said sample,
   wherein Ovr110 antibody binding to cells in the sample or internalization of the Ovr110 antibody by cells in the sample indicate cells in the sample express Ovr110.

23. A method for detecting Ovr110 overexpression in a subject in need thereof comprising,
   (a) combining a serum sample of a subject with an Ovr110 antibody of claim 1 under conditions suitable for specific binding of the Ovr110 antibody to Ovr110 in said serum sample,
   (b) determining the level of Ovr110 in the serum sample, and
   (c) comparing the level of Ovr110 determined in step b to the level of Ovr110 in a control,
   wherein an increase in the level of Ovr110 in the serum sample from the subject as compared to the control is indicative of Ovr110 overexpression in the subject.

24. The method of claim 23 wherein the subject has cancer.

25. The method of claim 24 wherein the subject has breast or ovarian cancer.

26. The antibody of claim 1 which is detectably labeled.

27. The antibody of claim 26 wherein the label is selected from the group comprising radiolabels, fluorescent labels, gold particles, and enzymatic labels.

28. An isolated antibody that competes for binding to the same epitope as the epitope bound by the monoclonal antibody produced by a hybridoma selected from the group consisting of American Type Culture Collection accession number PTA-5180, PTA-5855, PTA-5856 and PTA-5884.

29. The antibody of claim 28 which is a monoclonal antibody produced by a hybridoma selected from the group consisting of American Type Culture Collection accession number PTA-5180, PTA-5855, PTA-5856 and PTA-5884.

30. The antibody of claim 28 which is conjugated to a growth inhibitory agent or a cytotoxic agent.

31. The antibody of claim 30 wherein the cytotoxic agent is selected from the group consisting of toxins, antibiotics, radioactive isotopes and nucleolytic enzymes.

32. The antibody of claim 31, wherein the cytotoxic agent is a toxin selected from the group consisting of ricin, saponin, maytansinoid and calicheamicin.

33. The antibody of claim 28 which is detectably labeled.

34. The antibody of claim 33 wherein the label is selected from the group comprising radiolabels, fluorescent labels, gold particles, and enzymatic labels.

35. An isolated cell that produces the antibody of claim 28.

36. A composition comprising the antibody of claim 28 and a carrier.

37. The composition of claim 36, wherein the antibody is conjugated to a cytotoxic agent.

38. The composition of claim 36, wherein the antibody is a chimeric, human or humanized antibody and the carrier is a pharmaceutical carrier.

39. The antibody of claim 1 which is a monoclonal antibody produced by the hybridoma of American Type Culture Collection accession number PTA-5180.

40. The antibody of claim 1 which is a monoclonal antibody produced by the hybridoma of American Type Culture Collection accession number PTA-5855.

41. The antibody of claim 1 which is a monoclonal antibody produced by the hybridoma of American Type Culture Collection accession number PTA-5856.

42. The antibody of claim 1 which is a monoclonal antibody produced by the hybridoma of American Type Culture Collection accession number PTA-5884.

43. The antibody of claim 1, wherein the antibody competes for binding to the same epitope as the epitope bound by the monoclonal antibody produced by the hybridoma of American Type Culture Collection accession number PTA-5180.

44. The antibody of claim 1, wherein the antibody competes for binding to the same epitope as the epitope bound by the monoclonal antibody produced by the hybridoma of American Type Culture Collection accession number PTA-5855.

45. The antibody of claim 1, wherein the antibody competes for binding to the same epitope as the epitope bound by the monoclonal antibody produced by the hybridoma of American Type Culture Collection accession number PTA-5856.

46. The antibody of claim 1, wherein the antibody competes for binding to the same epitope as the epitope bound by the monoclonal antibody produced by the hybridoma of American Type Culture Collection accession number PTA-5884.

47. An article of manufacture comprising a container and the antibody of claim 1.

48. The article of manufacture of claim 47 which further comprises a carrier.

49. The article of manufacture of claim 47 which further comprises a label or package insert.

50. The antibody of claim 3 which is produced in bacteria.

51. An isolated antibody that inhibits the growth of Ovr110-expressing cancer cells, wherein the antibody competes for binding to the same epitope as the epitope bound by the monoclonal antibody produced by a hybridoma selected from the group consisting of American Type Culture Collection accession number PTA-5180, PTA-5855, PTA-5856 and PTA-5884.

52. The antibody of claim 51 which is a monoclonal antibody produced by a hybridoma selected from the group consisting of American Type Culture Collection accession number PTA-5180, PTA-5855, PTA-5856 and PTA-5884.

53. The antibody of claim 51 which is a monoclonal antibody produced by the hybridoma of American Type Culture Collection accession number PTA-5180.

54. The antibody of claim 51 which is a monoclonal antibody produced by the hybridoma of American Type Culture Collection accession number PTA-5855.

55. The antibody of claim 51 which is a monoclonal antibody produced by the hybridoma of American Type Culture Collection accession number PTA-5856.

56. The antibody of claim 51 which is a monoclonal antibody produced by the hybridoma of American Type Culture Collection accession number PTA-5884.

57. The antibody of claim 51, wherein the antibody competes for binding to the same epitope as the epitope bound by the monoclonal antibody produced by the hybridoma of American Type Culture Collection accession number PTA-5180.

58. The antibody of claim 51, wherein the antibody competes for binding to the same epitope as the epitope bound by the monoclonal antibody produced by the hybridoma of American Type Culture Collection accession number PTA-5855.

59. The antibody of claim 51, wherein the antibody competes for binding to the same epitope as the epitope bound by the monoclonal antibody produced by the hybridoma of American Type Culture Collection accession number PTA-5856.

60. The antibody of claim 51, wherein the antibody competes for binding to the same epitope as the epitope bound by the monoclonal antibody produced by the hybridoma of American Type Culture Collection accession number PTA-5884.

61. An article of manufacture comprising a container and the antibody of claim 51.

62. The article of manufacture of claim 61 which further comprises a carrier.

63. The article of manufacture of claim 61 which further comprises a label or package insert.

64. A method of killing an Ovr110-expressing cancer cell, comprising contacting the cancer cell with the antibody of claim 51, thereby killing the cancer cell.

65. The method of claim 64, wherein the cancer cell is selected from the group consisting of ovarian, pancreatic, lung and breast cancer cell.

66. The method of claim 64, wherein the antibody is conjugated to a cytotoxic agent.

67. The method of claim 66, wherein the cytotoxic agent is a toxin selected from the group consisting of maytansinoid, ricin, saporin and calicheamicin or a radioisotope.

68. The method of claim 64, wherein the antibody is administered in conjunction with at least one chemotherapeutic agent.

69. The method of claim 68 wherein the chemotherapeutic agent is paclitaxel or derivatives thereof.

70. A method for determining if cells in a sample express Ovr110 comprising
    (a) contacting a sample of cells with an Ovr110 antibody of claim 51 under conditions suitable for specific binding of the Ovr110 antibody to Ovr110, and
    (b) determining the level of binding of the antibody to cells in the sample, or the level of Ovr110 antibody internalization by cells in said sample,
    wherein Ovr110 antibody binding to cells in the sample or internalization of the Ovr110 antibody by cells in the sample indicate cells in the sample express Ovr110.

71. A method for detecting Ovr110 overexpression in a subject in need thereof comprising,
    (a) combining a serum sample of a subject with an Ovr110 antibody of claim 51 under conditions suitable for specific binding of the Ovr110 antibody to Ovr110 in said serum sample
    (b) determining the level of Ovr110 in the serum sample, and
    (c) comparing the level of Ovr110 determined in step b to the level of Ovr110 in a control,
    wherein an increase in the level of Ovr110 in the serum sample from the subject as compared to the control is indicative of Ovr110 overexpression in the subject.

72. The method of claim 71 wherein the subject has cancer.

73. The method of claim 72 wherein the subject has breast or ovarian cancer.

74. The antibody of claim 28 which is a monoclonal, chimeric, human or humanized antibody.

75. The antibody of claim 74 which is produced in bacteria.

76. The antibody of claim 28 which competes for binding to the same epitope as the epitope bound by the monoclonal antibody produced by the hybridoma of American Type Culture Collection accession number PTA-5180.

77. The antibody of claim 28 which competes for binding to the same epitope as the epitope bound by the monoclonal antibody produced by the hybridoma of American Type Culture Collection accession number PTA-5855.

78. The antibody of claim 28 which competes for binding to the same epitope as the epitope bound by the monoclonal antibody produced by the hybridoma of American Type Culture Collection accession number PTA-5856.

79. The antibody of claim 28 which competes for binding to the same epitope as the epitope bound by the monoclonal antibody produced by the hybridoma of American Type Culture Collection accession number PTA-5884.

80. The antibody of claim 28 which is a monoclonal antibody produced by the hybridoma of American Type Culture Collection accession number PTA-5180.

81. The antibody of claim 28 which is a monoclonal antibody produced by the hybridoma of American Type Culture Collection accession number PTA-5855.

82. The antibody of claim 28 which is a monoclonal antibody produced by the hybridoma of American Type Culture Collection accession number PTA-5856.

83. The antibody of claim 28 which is a monoclonal antibody produced by the hybridoma of American Type Culture Collection accession number PTA-5884.

84. An article of manufacture comprising a container and the antibody of claim 28.

85. The article of manufacture of claim 84 which further comprises a carrier.

86. The article of manufacture of claim 84 which further comprises a label or package insert.

87. A method of killing an Ovr110-expressing cancer cell, comprising contacting the cancer cell with the antibody of claim 28, thereby killing the cancer cell.

88. The method of claim 87, wherein the cancer cell is selected from the group consisting of ovarian, pancreatic, lung and breast cancer cell.

89. The method of claim 87, wherein the antibody is conjugated to a cytotoxic agent.

90. The method of claim 89, wherein the cytotoxic agent is a toxin selected from the group consisting of maytansinoid, ricin, saporin and calicheamicin or a radioisotope.

91. The method of claim 87, wherein the antibody is administered in conjunction with at least one chemotherapeutic agent.

92. The method of claim 91 wherein the chemotherapeutic agent is paclitaxel or derivatives thereof.

93. A method for determining if cells in a sample express Ovr110 comprising
   (a) contacting a sample of cells with an Ovr110 antibody of claim 28 under conditions suitable for specific binding of the Ovr110 antibody to Ovr110, and
   (b) determining the level of binding of the antibody to cells in the sample, or the level of Ovr110 antibody internalization by cells in said sample,
   wherein Ovr110 antibody binding to cells in the sample or internalization of the Ovr110 antibody by cells in the sample indicate cells in the sample express Ovr110.

94. A method for detecting Ovr110 overexpression in a subject in need thereof comprising,
   (a) combining a serum sample of a subject with an Ovr110 antibody of claim 28 under conditions suitable for specific binding of the Ovr110 antibody to Ovr110 in said serum sample,
   (b) determining the level of Ovr110 in the serum sample, and
   (c) comparing the level of Ovr110 determined in step b to the level of Ovr110 in a control,
   wherein an increase in the level of Ovr110 in the serum sample from the subject as compared to the control is indicative of Ovr110 overexpression in the subject.

95. The method of claim 94 wherein the subject has cancer.

96. The method of claim 95 wherein the subject has breast or ovarian cancer.

97. An isolated monoclonal antibody produced by a hybridoma selected from the group consisting of American Type Culture Collection accession number PTA-5180, PTA-5855, PTA-5856 and PTA-5884.

98. The antibody of claim 97 which is a monoclonal antibody produced by the hybridoma of American Type Culture Collection accession number PTA-5180.

99. The antibody of claim 97 which is a monoclonal antibody produced by the hybridoma of American Type Culture Collection accession number PTA-5855.

100. The antibody of claim 97 which is a monoclonal antibody produced by the hybridoma of American Type Culture Collection accession number PTA-5856.

101. The antibody of claim 97 which is a monoclonal antibody produced by the hybridoma of American Type Culture Collection accession number PTA-5884.

102. The antibody of claim 97 which is a chimeric, human or humanized antibody variant thereof.

103. The antibody of claim 102 which is produced in bacteria.

104. The antibody of claim 97 which is conjugated to a growth inhibitory agent or a cytotoxic agent.

105. The antibody of claim 104 wherein the cytotoxic agent is selected from the group consisting of toxins, antibiotics, radioactive isotopes and nucleolytic enzymes.

106. The antibody of claim 105, wherein the toxin is selected from the group consisting of ricin, saponin, maytansinoid and calicheamicin.

107. The antibody of claim 97 which is detectably labeled.

108. The antibody of claim 107 wherein the label is selected from the group comprising radiolabels, fluorescent labels, gold particles, and enzymatic labels.

109. An isolated cell that produces the antibody of claim 97.

110. A composition comprising the antibody of claim 97 and a carrier.

111. The composition of claim 110, wherein the antibody is conjugated to a cytotoxic agent.

112. The composition of claim 110, wherein the antibody is a chimeric, human or humanized antibody and the carrier is a pharmaceutical carrier.

113. An article of manufacture comprising a container and the antibody of claim 97.

114. The article of manufacture of claim 113 which further comprises a carrier.

115. The article of manufacture of claim 113 which further comprises a label or package insert.

116. A method of killing an Ovr110-expressing cancer cell, comprising contacting the cancer cell with the antibody of claim 97, thereby killing the cancer cell.

117. The method of claim 116, wherein the cancer cell is selected from the group consisting of ovarian, pancreatic, lung and breast cancer cell.

118. The method of claim 116, wherein the antibody is conjugated to a cytotoxic agent.

119. The method of claim 118, wherein the cytotoxic agent is a toxin selected from the group consisting of maytansinoid, ricin, saporin and calicheamicin or a radioisotope.

120. The method of claim 116, wherein the antibody is administered in conjunction with at least one chemotherapeutic agent.

121. The method of claim 120 wherein the chemotherapeutic agent is paclitaxel or derivatives thereof.

122. A method for determining if cells in a sample express Ovr110 comprising
   (a) contacting a sample of cells with an Ovr110 antibody of claim 97 under conditions suitable for specific binding of the Ovr110 antibody to Ovr110, and
   (b) determining the level of binding of the antibody to cells in the sample, or the level of Ovr110 antibody internalization by cells in said sample,
   wherein Ovr110 antibody binding to cells in the sample or internalization of the Ovr110 antibody by cells in the sample indicate cells in the sample express Ovr110.

123. A method for detecting Ovr110 overexpression in a subject in need thereof comprising,
   (a) combining a serum sample of a subject with an Ovr110 antibody of claim 97 under conditions suitable for specific binding of the Ovr110 antibody to Ovr110 in said serum sample,
   (b) determining the level of Ovr110 in the serum sample, and
   (c) comparing the level of Ovr110 determined in step b to the level of Ovr110 in a control,
   wherein an increase in the level of Ovr110 in the serum sample from the subject as compared to the control is indicative of Ovr110 overexpression in the subject.

124. The method of claim 123 wherein the subject has cancer.

125. The method of claim 124 wherein the subject has breast or ovarian cancer.

126. An isolated antibody that internalizes upon binding to Ovr110 on a mammalian cell, wherein the antibody competes for binding to the same epitope as the epitope bound by the monoclonal antibody produced by a hybridoma selected from the group consisting of American Type Culture Collection accession number PTA-5180, PTA-5855, PTA-5856 and PTA-5884.

127. The antibody of claim 126 which is a monoclonal antibody produced by a hybridoma selected from the group consisting of American Type Culture Collection accession number PTA-5180, PTA-5855, PTA-5856 and PTA-5884.

128. The antibody of claim 126 which is a monoclonal antibody produced by the hybridoma of American Type Culture Collection accession number PTA-5180.

129. The antibody of claim 126 which is a monoclonal antibody produced by the hybridoma of American Type Culture Collection accession number PTA-5855.

130. The antibody of claim 126 which is a monoclonal antibody produced by the hybridoma of American Type Culture Collection accession number PTA-5856.

131. The antibody of claim 126 which is a monoclonal antibody produced by the hybridoma of American Type Culture Collection accession number PTA-5884.

132. The antibody of claim 126, wherein the antibody competes for binding to the same epitope as the epitope bound by the monoclonal antibody produced by the hybridoma of American Type Culture Collection accession number PTA-5180.

133. The antibody of claim 126, wherein the antibody competes for binding to the same epitope as the epitope bound by the monoclonal antibody produced by the hybridoma of American Type Culture Collection accession number PTA-5855.

134. The antibody of claim 126, wherein the antibody competes for binding to the same epitope as the epitope bound by the monoclonal antibody produced by the hybridoma of American Type Culture Collection accession number PTA-5856.

135. The antibody of claim 126, wherein the antibody competes for binding to the same epitope as the epitope bound by the monoclonal antibody produced by the hybridoma of American Type Culture Collection accession number PTA-5884.

136. An article of manufacture comprising a container and the antibody of claim 126.

137. The article of manufacture of claim 136 which further comprises a carrier.

138. The article of manufacture of claim 136 which further comprises a label or package insert.

139. A method of killing an Ovr110-expressing cancer cell, comprising contacting the cancer cell with the antibody of claim 126, thereby killing the cancer cell.

140. The method of claim 139, wherein the cancer cell is selected from the group consisting of ovarian, pancreatic, lung and breast cancer cell.

141. The method of claim 139, wherein the antibody is conjugated to a cytotoxic agent.

142. The method of claim 141, wherein the cytotoxic agent is a toxin selected from the group consisting of maytansinoid, ricin, saporin and calicheamicin or a radioisotope.

143. The method of claim 139, wherein the antibody is administered in conjunction with at least one chemotherapeutic agent.

144. The method of claim 143 wherein the chemotherapeutic agent is paclitaxel or derivatives thereof.

145. A method for determining if cells in a sample express Ovr110 comprising
  (a) contacting a sample of cells with an Ovr110 antibody of claim 126 under conditions suitable for specific binding of the Ovr110 antibody to Ovr110, and
  (b) determining the level of binding of the antibody to cells in the sample, or the level of Ovr110 antibody internalization by cells in said sample,
  wherein Ovr110 antibody binding to cells in the sample or internalization of the Ovr110 antibody by cells in the sample indicate cells in the sample express Ovr110.

146. A method for detecting Ovr110 overexpression in a subject in need thereof comprising,
  (a) combining a serum sample of a subject with an Ovr110 antibody of claim 126 under conditions suitable for specific binding of the Ovr110 antibody to Ovr110 in said serum sample,
  (b) determining the level of Ovr110 in the serum sample, and
  (c) comparing the level of Ovr110 determined in step b to the level of Ovr110 in a control,
  wherein an increase in the level of Ovr110 in the serum sample from the subject as compared to the control is indicative of Ovr110 overexpression in the subject.

147. The method of claim 146 wherein the subject has cancer.

148. The method of claim 147 wherein the subject has breast or ovarian cancer.

* * * * *